(12) United States Patent
Bruhn et al.

(10) Patent No.: US 12,310,830 B2
(45) Date of Patent: May 27, 2025

(54) BIOCOMPATIBLE MEMBRANE COMPOSITE

(71) Applicants: W. L. Gore & Associates, Inc., Newark, DE (US); ViaCyte, Inc., San Diego, CA (US)

(72) Inventors: Timothy M. Bruhn, Newark, DE (US); Kevin D'Amour, San Diego, CA (US); Christopher Folk, San Diego, CA (US); Craig McGreevy, San Diego, CA (US); Laura Martinson, San Diego, CA (US); Scott A. Ritrovato, Newark, DE (US); Greg Rusch, Newark, DE (US); Michael Scott, San Diego, CA (US); Lauren R. Zambotti, Newark, DE (US); Qiang (John) Zhang, San Diego, CA (US); Joseph Kakkassery, San Diego, CA (US)

(73) Assignees: W. L. Gore & Associates, Inc., Newark, DE (US); ViaCyte, Inc., San Diego, CA (US)

( * ) Notice: Subject to any disclaimer, the term of this patent is extended or adjusted under 35 U.S.C. 154(b) by 694 days.

(21) Appl. No.: 17/595,906

(22) PCT Filed: May 30, 2020

(86) PCT No.: PCT/US2020/035449
§ 371 (c)(1),
(2) Date: Nov. 29, 2021

(87) PCT Pub. No.: WO2020/243665
PCT Pub. Date: Dec. 3, 2020

(65) Prior Publication Data
US 2022/0370184 A1      Nov. 24, 2022

Related U.S. Application Data

(60) Provisional application No. 62/897,636, filed on Sep. 9, 2019, provisional application No. 62/855,540, filed on May 31, 2019.

(51) Int. Cl.
*A61L 27/56* (2006.01)
*A61F 2/00* (2006.01)
(Continued)

(52) U.S. Cl.
CPC ............ *A61F 2/0077* (2013.01); *A61F 2/022* (2013.01); *A61L 27/34* (2013.01); *A61L 27/3804* (2013.01);
(Continued)

(58) Field of Classification Search
CPC ...... A61L 27/34; A61L 27/3804; A61L 27/54; A61L 27/56; A61F 2/0077; A61F 2/022; A61F 2210/0076; A61F 2002/0086
See application file for complete search history.

(56) References Cited

U.S. PATENT DOCUMENTS

| 5,713,888 A | 2/1998 | Neuenfeldt |
| 6,060,640 A | 5/2000 | Pauley |

(Continued)

FOREIGN PATENT DOCUMENTS

| WO | WO-2000/043052 | 7/2000 |
| WO | WO-2003/011354 | 2/2003 |

(Continued)

OTHER PUBLICATIONS

International Search Report and Written Opinion issued in PCT/US2020/035449, mailed Oct. 2, 2020, 16 pages.

*Primary Examiner* — Dinah Baria
(74) *Attorney, Agent, or Firm* — Wolf, Greenfield & Sacks, P.C.

(57) ABSTRACT

A biocompatible membrane composite including a cell impermeable layer and a mitigation layer is provided. The cell impermeable layer is impervious to vascular ingrowth and prevents cellular contact from the host. Additionally, the mitigation layer includes solid features. In at least one (Continued)

embodiment, mitigation layer has therein bonded solid features. In some embodiments, the cell impermeable layer and the mitigation layer are intimately bonded or otherwise connected to each other to form a composite layer having a tight/open structure. A reinforcing component may optionally be positioned external to or within the biocompatible membrane composite to provide support to and prevent distortion. The biocompatible membrane composite may be used in or to form a device for encapsulating biological entities, including, but not limited to, pancreatic lineage type cells such as pancreatic progenitors.

28 Claims, 44 Drawing Sheets

(51) Int. Cl.
  *A61F 2/02*  (2006.01)
  *A61L 27/34*  (2006.01)
  *A61L 27/38*  (2006.01)
  *A61L 27/54*  (2006.01)

(52) U.S. Cl.
  CPC ............... *A61L 27/54* (2013.01); *A61L 27/56* (2013.01); *A61F 2002/0086* (2013.01); *A61F 2210/0076* (2013.01)

(56) References Cited

U.S. PATENT DOCUMENTS

| | | |
|---|---|---|
| 8,118,877 B2 | 2/2012 | Brauker |
| 2017/0240864 A1 | 8/2017 | Zavazava |
| 2018/0125632 A1* | 5/2018 | Cully ..................... A61F 2/022 |
| 2018/0333679 A1 | 11/2018 | Puglia |

FOREIGN PATENT DOCUMENTS

| | | |
|---|---|---|
| WO | WO-2014/073441 | 5/2014 |
| WO | 2014/173441 A1 | 10/2014 |
| WO | WO-2018/089011 | 5/2018 |
| WO | WO-2018/089399 | 5/2018 |

* cited by examiner

BIOCOMPATIBLE MEMBRANE COMPOSITE

FIELD

The present invention relates to the field of implantable medical devices and, in particular, to a biocompatible membrane composite.

BACKGROUND

Biological therapies are increasingly viable methods for treating peripheral artery disease, aneurysm, heart disease, Alzheimer's and Parkinson's diseases, autism, blindness, diabetes, and other pathologies.

With respect to biological therapies in general, cells, viruses, viral vectors, bacteria, proteins, antibodies, and other bioactive entities may be introduced into a patient by surgical or interventional methods that place the bioactive moiety into a tissue bed of a patient. Often the bioactive entities are first placed in a device that is then inserted into the patient. Alternatively, the device may be inserted into the patient first with the bioactive entity added later. The device is formed of one or more biocompatible membranes or other biocompatible materials that permit the passage of nutrients through but prevent the passage of the cells encapsulated therethrough.

To maintain a viable and productive population of bioactive entities (e.g., cells), the bioactive entities must maintain access to nutrients, such as oxygen, which are delivered through the blood vessels of the host. To maximize the viability and productivity of the implanted, encapsulated cells, it is necessary to maximize access to the source of oxygen and nutrients by ensuring that the formation of blood vessels be as close as possible to the cells such that the diffusion distance and time needed for transport of the oxygen and nutrients to the implanted, encapsulated cells is minimized.

The implantation of external devices, such as, for example, cell encapsulation devices, into a body triggers an immune response in which foreign body giant cells form and at least partially encapsulate the implanted device. The presence of foreign body giant cells at or near the cell impermeable interface makes it difficult, if not impossible for blood vessels to form in close proximity to the encapsulated cells, thereby restricting access to the oxygen and nutrients needed to maintain the viability and health of the encapsulated cells.

Thus, there remains a need in the art for a material that provides the encapsulated cells sufficient immune isolation from the host's immune cells while providing an environment that is able to mitigate or tailor the foreign body response such that sufficient blood vessels are able to form at a cell impermeable interface, thereby permitting the implanted cells to survive and secrete a therapeutically useful substance.

SUMMARY

In one Aspect ("Aspect 1"), a biocompatible membrane composite includes (1) a first layer having an MPS (maximum pore size) less than about 1 micron and (2) a second layer having a majority of bonded solid features having a solid feature spacing less than about 50 microns, where at least a portion of the bonded features are intimately bonded to the first layer.

According to another Aspect, ("Aspect 2") further to Aspect 1, the first layer has a mass per area (MpA) less than about 5 g/m$^2$.

According to another Aspect, ("Aspect 3") further to any one of Aspects 1 and 2, first layer has a thickness less than about 10 microns.

According to another Aspect, ("Aspect 4") further to any one of Aspects 1 to 3, the biocompatible membrane composite has a maximum tensile load in the weakest axis greater than about 40 N/m.

According to another Aspect, ("Aspect 5") further to any one Aspects 1 to 4, the first layer has a first porosity greater than about 50%.

According to another Aspect, ("Aspect 6") further to Aspects 1 to 5, the second layer has a second porosity greater than about 60%.

According to another Aspect, ("Aspect 7") Aspects 1 to 6, the second layer has a thickness less than about 200 microns.

According to another Aspect, ("Aspect 8") further to any one of Aspects 1 to 7, the bonded solid features each include a representative minor axis, a representative major axis, and a solid feature depth, where a majority of at least two of the representative minor axis, the representative major axis, and the solid feature depth is greater than about 5 microns.

According to another Aspect, ("Aspect 9") further to any one Aspects 1 to 8, the second layer has a pore size from about 1 micron to about 9 microns in effective diameter.

According to another Aspect, ("Aspect 10") further to any one of Aspects 1 to 9, the solid features are connected by fibrils and said fibrils are deformable.

According to another Aspect, ("Aspect 11") further to any one of Aspects 1 to 10, the majority of the bonded solid features have a representative minor axis from about 3 microns to about 20 microns.

According to another Aspect, ("Aspect 12") further to any one of Aspects 1 to 11, the first layer and the second layer are intimately bonded.

According to another Aspect, ("Aspect 13") further to any one of Aspects 1 to 12, at least one of the first layer and the second layer includes a polymer, fluoropolymer membranes, a non-fluoropolymer membrane, a woven textile, a non-woven textile, woven or non-woven collections of fibers or yarns, fibrous matrices, and combinations thereof.

According to another Aspect, ("Aspect 14") further to any one of Aspects 1 to 13, at least one of the first layer and the second layer is a polymer.

According to another Aspect, ("Aspect 15") further to Aspect 13 or Aspect 14, the polymer includes an expanded polytetrafluoroethylene (ePTFE) membrane, a fluorinated ethylene propylene (FEP) membrane and a modified ePTFE membrane.

According to another Aspect, ("Aspect 16") further to any one of Aspects 1 to 15, at least one of the first layer and the second layer is an expanded polytetrafluoroethylene membrane.

According to another Aspect, ("Aspect 17") further to any one of Aspects 1 to 16, the second layer includes at least one of a textile and a non-fluoropolymer material.

According to another Aspect, ("Aspect 18") further to Aspect 17, the textile may be woven textiles, non-woven textiles, spunbound textiles, melt blown fibrous materials, or electrospun nanofibers.

According to another Aspect, ("Aspect 19") further to Aspect 17, the non-fluoropolymer material is selected from polyvinylidene difluoride, nanofibers, polysulfones, polyethersulfones, polyarlysulfones, polyether ether ketone, polyethylenes, polypropylenes, polyimides and combinations thereof.

According to another Aspect, ("Aspect 20") further to any one of Aspects 1 to 19, including a reinforcing component.

According to another Aspect, ("Aspect 21") further to any one of Aspects 1 to 20, the reinforcing component is a woven or non-woven textile.

According to another Aspect, ("Aspect 22") further to any one of Aspects 1 to 21, the bonded solid features include a member selected from a thermoplastic polymer, polyurethanes, silicones, rubbers, epoxies and combinations thereof.

According to another Aspect, ("Aspect 23") further to any one of Aspects 1 to 22, the biocompatible membrane composite has thereon a surface coating that is one or more of a member selected from antimicrobial agents, antibodies, pharmaceuticals, and other biologically active molecules.

According to another Aspect, ("Aspect 24") further to any one of Aspects 1 to 23, the biocompatible membrane composite has a hydrophilic coating thereon.

According to another Aspect, ("Aspect 25") further to any one of Aspects 1 to 24, the biocompatible membrane composite is in the form of a cell encapsulation device.

In one Aspect, ("Aspect 26") a biocompatible membrane composite includes (1) a first layer having an MPS (maximum pore size) less than about 1 micron, and (2) a second layer having a majority of solid features with a solid feature spacing less than about 50 microns, where the solid features each include a representative minor axis, a representative major axis, and a solid feature depth, and where a majority of at least two of the representative minor axis, the representative major axis, and the solid feature depth is greater than about 5 microns.

According to another Aspect, ("Aspect 27") further to Aspect 26, a majority of the representative minor axis is from about 3 microns to about 20 microns.

According to another Aspect, ("Aspect 28") further to Aspect 26 or Aspect 27, the first layer has a mass per area (MpA) less than about 5 g/m².

According to another Aspect, ("Aspect 29") further to any one of Aspects 26 to 29, the first layer has a first thickness less than about 10 microns.

According to another Aspect, ("Aspect 30") further to any one of Aspects 26 to 29, the second layer has a second thickness less than about 200 microns.

According to another Aspect, ("Aspect 31") further any one of Aspects 26 to 30, the biocompatible membrane composite has a maximum tensile load in the weakest axis greater than about 40 N/m.

According to another Aspect, ("Aspect 32") further to any one of Aspects 26 to 31, the first layer has a first porosity greater than about 50%.

According to another Aspect, ("Aspect 33") further to any one of Aspects 26 to 32, the second layer has a second porosity greater than about 60%.

According to another Aspect, ("Aspect 34") further to any one of Aspects 26 to 33 the biocompatible membrane composite has a geometric mean tensile strength greater than 20 MPa.

According to another Aspect, ("Aspect 35") further to any one of Aspects 26 to 34, at least a portion of the solid features in contact with the first layer are bonded solid features.

According to another Aspect, ("Aspect 36") further to any one of Aspects 26 to 35 the solid features are connected by fibrils and said fibrils are deformable.

According to another Aspect, ("Aspect 37") further to any one of Aspects 26 to 36, the second layer includes a woven or a non-woven textile.

According to another Aspect, ("Aspect 38") further to any one of Aspects 26 to 37, the first layer and the second layer are intimately bonded.

According to another Aspect, ("Aspect 39") further to any one of Aspects 26 to 38, at least one of the first layer and the second layer includes a member selected from a polymer, a fluoropolymer membrane, a non-fluoropolymer membrane, a woven textile, a non-woven textile, woven or non-woven collections of fibers or yarns, fibrous matrices, and combinations thereof.

According to another Aspect, ("Aspect 40") further to any one of Aspects 26 to 39, at least one of the first layer and the second layer is a polymer.

According to another Aspect, ("Aspect 41") further to Aspect 40, the polymer is selected from an expanded polytetrafluoroethylene membrane, a fluorinated ethylene propylene membrane, and a modified expanded polytetrafluoroethylene membrane.

According to another Aspect, ("Aspect 42") further to any one of Aspects 26 to 41, at least one of the first layer and the second layer is an expanded polytetrafluoroethylene membrane.

According to another Aspect, ("Aspect 43") further to any one of Aspects 26 to 42, the second layer includes at least one of a textile and a non-fluoropolymer membrane.

According to another Aspect, ("Aspect 44") further to Aspect 43, the textile is selected from woven textiles, non-woven textiles, spunbound textiles, melt blown fibrous materials and electrospun nanofibers.

According to another Aspect, ("Aspect 45") further to Aspect 43, the non-fluoropolymer membrane is selected from polyvinylidene difluoride, nanofibers, polysulfones, polyethersulfones, polyarlysulfones, polyether ether ketone, polyethylenes, polypropylenes, polyimides, and combinations thereof.

According to another Aspect, ("Aspect 46") further to any one of Aspects 26 to 45, the second layer is a spunbound non-woven polyester material.

According to another Aspect, ("Aspect 47") further to any one of Aspects 26 to 46, including a reinforcing component.

According to another Aspect, ("Aspect 48") further to Aspect 47, the reinforcing component is a woven or non-woven textile.

According to another Aspect, ("Aspect 49") further to any one of Aspects 26 to 48, the solid features of the second layer include a member selected from thermoplastic polymers, polyurethanes, silicones, rubbers, epoxies, and combinations thereof.

According to another Aspect, ("Aspect 50") further to any one of Aspects 26 to 49, the biocompatible membrane composite has thereon a surface coating that includes one or more members selected from antimicrobial agents, antibodies, pharmaceuticals, and biologically active molecules.

According to another Aspect, ("Aspect 51") further to any one of Aspects 26 to 50, the biocompatible membrane composite has a hydrophilic coating thereon.

According to another Aspect, ("Aspect 52") further to any one of Aspects 26 to 51, the biocompatible membrane composite is in the form of a cell encapsulation device.

In one Aspect, ("Aspect 53") a biocompatible membrane composite includes (1) a first layer with an MPS (maximum pore size) less than about 1 micron, a porosity greater than about 50%, a first thickness less than about 10 microns and (2) a second layer including a majority of solid features with a solid feature spacing less than about 50 microns.

In another Aspect, ("Aspect 54") further to Aspect 53, the biocompatible membrane composite has a maximum tensile load in the weakest axis greater than about 40 N/m.

According to another Aspect, ("Aspect 55") further to any one of Aspect 53 or Aspect 54, the first layer has a mass per area (MpA) less than about 5 g/m$^2$.

According to another Aspect, ("Aspect 56") further to any one of Aspects 53 to 55, the second layer has a second thickness less than about 200 microns.

According to another Aspect, ("Aspect 57") further to any one of Aspects 54 to 56, the second layer has a pore size from about 1 micron to about 9 microns in effective diameter.

According to another Aspect, ("Aspect 58") further to any one of Aspects 54 to 57, the solid features each includes a representative minor axis, a representative major axis, and a solid feature depth where a majority of at least two of the representative minor axis, the representative major axis, and the solid feature depth is greater than about 5 microns.

According to another Aspect, ("Aspect 59") further to Aspect 58, the solid feature depth is less than the second thickness of the second layer.

According to another Aspect, ("Aspect 60") further to any one of Aspects 54 to 59, the solid features are connected by fibrils and said fibrils are deformable.

According to another Aspect, ("Aspect 61") further to any one of Aspects 54 to 60, the second layer has a first porosity greater than about 60%.

According to another Aspect, ("Aspect 62") further to any one of Aspects 54 to 61, the biocompatible membrane composite has a geometric mean tensile strength greater than about 20 MPa.

According to another Aspect, ("Aspect 63") further to any one of Aspects 54 to 62, at least a portion of the first solid features in contact with the first layer are bonded solid features.

According to another Aspect, ("Aspect 64") further to any one of Aspects 54 to 63, the first layer and the second layer are intimately bonded.

According to another Aspect, ("Aspect 65") further to any one of Aspects 54 to 64, at least one of the first layer and the second layer includes a member selected from a polymer, a fluoropolymer membrane, a non-fluoropolymer membrane, a woven, a non-woven textile, woven or non-woven collections of fibers or yarns, fibrous matrices, and combinations thereof.

According to another Aspect, ("Aspect 66") further to any one of Aspects 54 to 65, at least one of the first layer and the second layer is a polymer.

According to another Aspect, ("Aspect 67") further to Aspect 66, the polymer is selected from an expanded polytetrafluoroethylene membrane, a fluorinated ethylene propylene membrane and a modified expanded polytetrafluoroethylene membrane.

According to another Aspect, ("Aspect 68") further to any one of Aspects 54 to 67, at least one of the first layer and the second layer is an expanded polytetrafluoroethylene membrane.

According to another Aspect, ("Aspect 69") further to any one of Aspects 54 to 68, the second layer includes at least one of a textile and a non-fluoropolymer membrane.

According to another Aspect, ("Aspect 70") further to Aspect 69, the textile is selected from woven textiles, non-woven textiles, spunbound textiles, melt blown fibrous materials, and electrospun nanofibers.

According to another Aspect, ("Aspect 71") further to Aspect 69, the non-fluoropolymer membrane is selected from polyvinylidene difluoride, nanofibers, polysulfones, polyethersulfones, polyarlysulfones, polyether ether ketone, polyethylenes, polypropylenes, polyimides, and combinations thereof.

According to another Aspect, ("Aspect 72") further to any one of Aspects 54 to 71, including a reinforcing component.

According to another Aspect, ("Aspect 73") further to Aspect 72, the reinforcing component is a woven or non-woven textile.

According to another Aspect, ("Aspect 74") further to any one of Aspects 54 to 73, the solid features of the second layer include a member selected from thermoplastic polymers, polyurethanes, silicones, rubbers, epoxies and combinations thereof.

According to another Aspect, ("Aspect 75") further to any one of Aspects 54 to 74, the biocompatible membrane composite has thereon a surface coating that includes one or more members selected from antimicrobial agents, antibodies, pharmaceuticals, and biologically active molecules.

According to another Aspect, ("Aspect 76") further to any one of Aspects 54 to 75, the biocompatible membrane composite has a hydrophilic coating thereon.

According to another Aspect, ("Aspect 77") further to any one of Aspects 54 to 76, the biocompatible membrane composite is in the form of a cell encapsulation device.

In one Aspect, ("Aspect 78") a cell encapsulation device includes (1) a first biocompatible membrane composite sealed along at least a portion of its periphery to a second biocompatible membrane composite sealed along at least a portion of its periphery to define lumen therebetween, and (2) at least one port in fluid communication with the lumen where at least one of the first and second biocompatible membrane composites include a first layer having an MPS (maximum pore size) less than about 1 micron and a second layer having a majority of bonded solid features with a solid feature spacing less than about 50 microns, where the bonded features are intimately bonded to the first layer.

According to another Aspect, ("Aspect 79") further to Aspect 77 or Aspect 78, the first layer has a mass per area (MpA) less than about 5 g/m$^2$.

According to another Aspect, ("Aspect 80") further to Aspect 78 or Aspect 79 the first layer has a first thickness less than about 10 microns.

According to another Aspect, ("Aspect 81") further to any one of Aspects 77 to 80, at least one of the first biocompatible membrane composite and the second biocompatible membrane composite has a maximum tensile load in the weakest axis greater than about 40 N/m.

According to another Aspect, ("Aspect 82") further to any one of Aspects 77 to 81, the first layer has a first porosity greater than about 50%.

According to another Aspect, ("Aspect 83") further to any one of Aspects 77 to 82, the second layer has a second porosity greater than about 60%.

According to another Aspect, ("Aspect 84") further to any one of Aspects 77 to 83, the second layer has a second thickness less than about 200 microns.

According to another Aspect, ("Aspect 85") further to any one of Aspects 77 to 84, the bonded solid features each include a representative minor axis, a representative major axis, and a solid feature depth and where a majority at least two of the representative minor axis, the representative major axis, the solid feature depth is greater than about 5 microns.

According to another Aspect, ("Aspect 86") further to any one of Aspects 77 to 85, the second layer has a pore size from about 1 micron to about 9 microns in effective diameter.

According to another Aspect, ("Aspect 87") further to any one of Aspects 77 to 86, the solid features are connected by fibrils and said fibrils are deformable.

According to another Aspect, ("Aspect 88") further to any one of Aspects 77 to 87, a majority of the bonded solid features has a representative minor axis from about 3 microns to about 20 microns.

According to another Aspect, ("Aspect 89") further to any one of Aspects 77 to 88, the first layer and the second layer are intimately bonded.

According to another Aspect, ("Aspect 90") further to any one of Aspects 77 to 89, at least one of the first layer and the second layer includes a polymer, a fluoropolymer membrane, a non-fluoropolymer membrane, a woven textile, a non-woven textile, woven or non-woven collections of fibers or yarns, fibrous matrices, and combinations thereof.

According to another Aspect, ("Aspect 91") further to any one of Aspects 77 to 90, at least one of the first layer and the second layer is a polymer.

According to another Aspect, ("Aspect 92") further to Aspect 91, the polymer is a fluoropolymer membrane selected from an expanded polytetrafluoroethylene membrane, a fluorinated ethylene propylene membrane and a modified expanded polytetrafluoroethylene membrane.

According to another Aspect, ("Aspect 93") further to any one of Aspects 77 to 92, at least one of the first layer and the second layer is an expanded polytetrafluoroethylene membrane.

According to another Aspect, ("Aspect 94") further to any one of Aspects 77 to 94, the second layer includes at least one of a textile and a non-fluoropolymer membrane.

According to another Aspect, ("Aspect 95") further to Aspect 94, the textile is selected from woven textiles, non-woven textiles, spunbound textiles, melt blown fibrous materials and electrospun nanofibers.

According to another Aspect, ("Aspect 96") further to Aspect 94, the non-fluoropolymer membrane is selected from polyvinylidene difluoride, nanofibers, polysulfones, polyethersulfones, polyarlysulfones, polyether ether ketone, polyethylenes, polypropylenes, polyimides, and combinations thereof.

According to another Aspect, ("Aspect 97") further to any one of Aspects 77 to 96, including a reinforcing component.

According to another Aspect, ("Aspect 98") further to Aspect 97, the reinforcing component is a woven or non-woven textile.

According to another Aspect, ("Aspect 99") further to any one of Aspects 77 to 98, including a reinforcing component external to at least one of the first biocompatible membrane composite and the second biocompatible membrane composite.

According to another Aspect, (Aspect 100) further to any one of Aspects 77 to 99, including an internal reinforcing component.

According to another Aspect, ("Aspect 101") further any one of Aspects 77 to 100, including an internal reinforcing component and a reinforcing component external to at least one of the first biocompatible membrane composite and the second biocompatible membrane composite.

According to another Aspect, ("Aspect 102") further to any one of Aspects further to any one of Aspects 79 to 101, including a filling tube.

According to another Aspect ("Aspect 103") further to any one of Aspects 79 to 102, the bonded solid features include a member selected from a thermoplastic polymer, polyurethanes, silicones, rubbers, epoxies and combinations thereof.

According to another Aspect, ("Aspect 104") further to any one of Aspects further to any one of Aspects 79 to 103, the biocompatible membrane composite has thereon a surface coating and the surface coating includes one or more members selected from antimicrobial agents, antibodies, pharmaceuticals and biologically active molecules.

According to another Aspect, ("Aspect 105") further to any one of Aspects 79 to 104, the biocompatible membrane composite has a hydrophilic coating thereon.

According to another Aspect, ("Aspect 106") further to any one of Aspects 79 to 105, including a first weld film positioned at least between the first biocompatible membrane composite and a first reinforcing component and a second weld film positioned at least between the second biocompatible membrane composite and a second reinforcing component.

According to another example ("Example 107") further to any one of the preceding Examples, a method for lowering blood glucose levels in a mammal includes transplanting a cell encapsulated device including a biocompatible membrane composite of any one of the previous claims, where cells encapsulated therein include a population of PDX1-positive pancreatic endoderm cells, and where the pancreatic endoderm cells mature into insulin secreting cells, thereby lowering blood glucose.

According to another example ("Example 108") further to any one of the preceding Examples, the PDX1-positive pancreatic endoderm cells include a mixture of cells further including endocrine and/or endocrine precursor cells, where the endocrine and/or endocrine precursor cells express chromogranin A (CHGA).

According to another example ("Example 109") further to any one of the preceding Examples, a method for lowering blood glucose levels in a mammal includes transplanting a cell encapsulation device as in claim 1, where cells encapsulated therein include a population of PDX1-positive pancreatic endoderm cells, and where the pancreatic endoderm cells mature into insulin secreting cells, thereby lowering blood glucose.

According to another example ("Example 110") further to any one of the preceding Examples, the PDX1-positive pancreatic endoderm cells include a mixture of cells further including endocrine and/or endocrine precursor cells, where the endocrine and/or endocrine precursor cells express chromogranin A (CHGA).

According to another example ("Example 111") further to any one of the preceding Examples, a method for lowering blood glucose levels in a mammal includes transplanting a cell encapsulation device including a first layer having an MPS (maximum pore size) less than about 1 micron in diameter and a second layer having a majority of bonded solid features having a solid feature spacing less than about 50 microns, where at least a portion of the bonded features are intimately bonded to the first layer, and a cell population including PDX1-positive pancreatic endoderm cells, and where the pancreatic endoderm cells mature into insulin secreting cells, thereby lowering blood glucose.

According to another example ("Example 112") further to any one of the preceding Examples, the PDX1-positive pancreatic endoderm cells include a mixture of cells further including endocrine and/or endocrine precursor cells, where the endocrine and/or endocrine precursor cells express chromogranin A (CHGA).

According to another example ("Example 113") further to any one of the preceding Examples, a method for lowering blood glucose levels in a mammal includes transplanting a biocompatible membrane composite that includes a first layer having an MPS (maximum pore size) less than about 1 micron in diameter and a second layer having a majority of bonded solid features having a solid feature spacing less than about 50 microns, where at least a portion of the bonded features are intimately bonded to the first layer, and a cell population including PDX1-positive pancreatic endoderm cells, and where the pancreatic endoderm cells mature into insulin secreting cells, thereby lowering blood glucose.

According to another example ("Example 114") further to any one of the preceding Examples, the PDX1-positive pancreatic endoderm cells include a mixture of cells further including endocrine and/or endocrine precursor cells, where the endocrine and/or endocrine precursor cells express chromogranin A (CHGA).

According to another example ("Example 115") further to any one of the preceding Examples, an encapsulated in vitro PDX1-positive pancreatic endoderm cells include a mixture of cell sub-populations including at least a pancreatic progenitor population co-expressing PDX-1/NKX6.1.

According to another example ("Example 116") further to any one of the preceding Examples, an encapsulated in vitro PDX1-positive pancreatic endoderm cells includes a mixture of cell sub-populations including at least a pancreatic progenitor population co-expressing PDX-1/NKX6.1 and a pancreatic endocrine and/or endocrine precursor population expressing PDX-1/NKX6.1 and CHGA.

According to another example ("Example 117") further to any one of the preceding Examples, at least 30% of the population includes pancreatic progenitor population co-expressing PDX-1/NKX6.1.

According to another example ("Example 118") further to any one of the preceding Examples, at least 40% of the population includes pancreatic progenitor population co-expressing PDX-1/NKX6.1.

According to another example ("Example 119") further to any one of the preceding Examples, at least 50% of the population includes pancreatic progenitor population co-expressing PDX-1/NKX6.1.

According to another example ("Example 120") further to any one of the preceding Examples, at least 20% of the population endocrine and/or endocrine precursor population express PDX-1/NKX6.1/CHGA.

According to another example ("Example 121") further to any one of the preceding Examples, at least 30% of the population endocrine and/or endocrine precursor population express PDX-1/NKX6.1/CHGA.

According to another example ("Example 122") further to any one of the preceding Examples, at least 40% of the population endocrine and/or endocrine precursor population express PDX-1/NKX6.1/CHGA.

According to another example ("Example 123") further to any one of the preceding Examples, the pancreatic progenitor cells and/or endocrine or endocrine precursor cells are capable of maturing into insulin secreting cells in vivo.

According to another example ("Example 124") further to any one of the preceding Examples, a method for producing insulin in vivo includes transplanting a cell encapsulated device including a biocompatible membrane composite of any one of the previous claims and a population of PDX-1 pancreatic endoderm cells mature into insulin secreting cells, where the insulin secreting cells secrete insulin in response to glucose stimulation.

According to another example ("Example 125") further to any one of the preceding Examples, the PDX1-positive pancreatic endoderm cells include a mixture of cells further including endocrine and/or endocrine precursor cells, where the endocrine and/or endocrine precursor cells express chromogranin A (CHGA).

According to another example ("Example 126") further to any one of the preceding Examples, at least about 30% of the population are endocrine and/or endocrine precursor population expressing PDX-1/NKX6.1/CHGA.

According to another example ("Example 127") further to any one of the preceding Examples, an in vitro human PDX1-positive pancreatic endoderm cell culture includes a mixture of PDX-1 positive pancreatic endoderm cells and at least a transforming growth factor beta (TGF-beta) receptor kinase inhibitor.

According to another example ("Example 128") further to any one of the preceding Examples, further including a bone morphogenetic protein (BMP) inhibitor.

According to another example ("Example 129") further to any one of the preceding Examples, the TGF-beta receptor kinase inhibitor is TGF-beta receptor type 1 kinase inhibitor.

According to another example ("Example 130") further to any one of the preceding Examples, the TGF-beta receptor kinase inhibitor is ALK5i.

According to another example ("Example 131") further to any one of the preceding Examples, the BMP inhibitor is noggin.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1A:
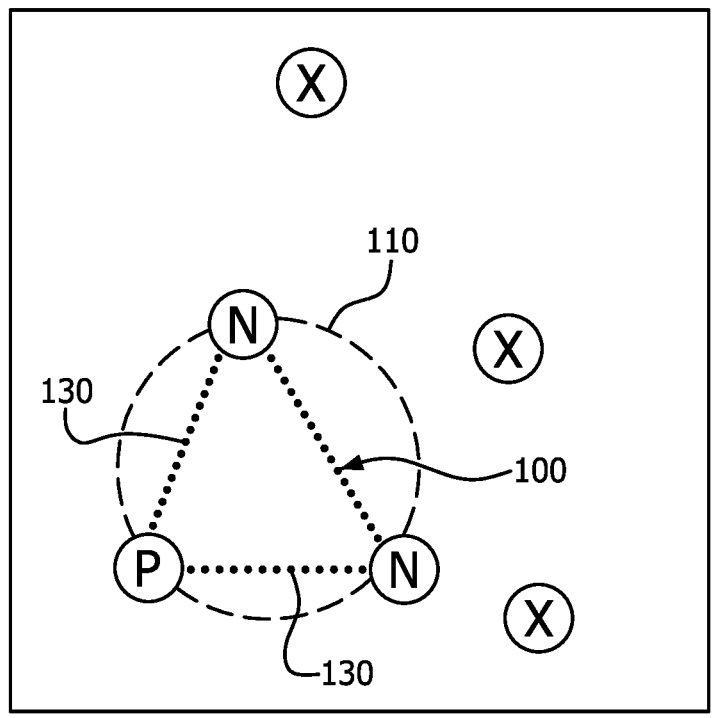
FIG. 1A is a schematic illustration depicting the determination of solid feature spacing where three neighboring solid features represent the corners of a triangle whose circumcircle has an interior devoid of additional solid features and the solid feature spacing is the straight distance between two of the solid features forming the triangle in accordance with embodiments described herein.

Persons skilled in the art will readily appreciate that various aspects of the present disclosure can be realized by any number of methods and apparatus configured to perform the intended functions. It should also be noted that the accompanying figures referred to herein are not necessarily drawn to scale, and may be exaggerated to illustrate various aspects of the present disclosure, and in that regard, the figures should not be construed as limiting. Directional references such as "up," "down," "top," "left," "right," "front," and "back," among others are intended to refer to the orientation as illustrated and described in the figure (or figures) to which the components and directions are referencing. It is to be appreciated that the terms "biocompatible membrane composite" and "membrane composite" are used interchangeably herein. It is to be noted that all ranges described herein are exemplary in nature and include any and all values in between. In addition, all references cited herein are incorporated by reference in their entireties.

The present disclosure is directed to a biocompatible membrane composite. The biocompatible membrane composite contains a first layer and a second layer. Each layer is distinct and serves a function that supports the survival of encapsulated cells. In certain embodiments, the first layer functions as a cell impermeable layer and the second layer functions as a mitigation layer. Herein, the term "first layer" is used interchangeably with "cell impermeable layer" and the term "second layer" is used interchangeably with "mitigation layer for ease of convenience. The mitigation layer reduces the formation of foreign body giant cells on a surface of the cell impermeable layer. In at least one embodiment, the mitigation layer includes solid features (e.g., nodes) that are present in the membrane forming the mitigation layer. In other embodiments, the mitigation layer includes solid features (e.g., printed solid features) that are provided and/or formed on a surface of the cell impermeable layer. In at least one embodiment, the mitigation layer has therein bonded solid features. In some embodiments, the cell impermeable layer and the mitigation layer are intimately bonded or otherwise connected to each other to form a composite layer having a tight/open structure. "Intimate bond" and "Intimately bonded", as used herein, refer to layers of the biocompatible membrane composite or to the solid features within the biocompatible membrane composite that are not readily separable or detachable at any point on their surface. A reinforcing component may optionally be positioned on either side of the biocompatible membrane composite (i.e., external to) or within the biocompatible membrane composite (i.e., internal to) to provide support to and prevent distortion of the biocompatible membrane composite. The biocompatible membrane composite may be used in or to form a device for encapsulating biological entities and/or cell populations. It is to be appreciated that the term "about" as used herein denotes +/−10% of the designated unit of measure.

Biological entities suitable for use with the biocompatible membrane composite include, but are not limited to, cells, viruses, viral vectors, gene therapies, bacteria, proteins, polysaccharides, antibodies, and other bioactive entities. It is to be appreciated that if a biological entity other than a cell is selected for use herein, the bioactive component or product of the biological entity needs to be able to pass through the cell impermeable layer, but not the entity itself. For simplicity, herein the biological entity is referred to as a cell, but nothing in this description limits the biological entity to cells or to any particular type of cell, and the following description applies also to biological entities that are not cells.

Various types of prokaryotic cells, eukaryotic cells, mammalian cells, non-mammalian cells, and/or stem cells may be used with the biocompatible membrane composite described herein. In some embodiments, the cells secrete a therapeutically useful substance. Such therapeutically useful substances include hormones, growth factors, trophic factors, neurotransmitters, lymphokines, antibodies, or other cell products which provide a therapeutic benefit to the device recipient. Examples of such therapeutic cell products include, but are not limited to, insulin and other pancreatic hormones, growth factors, interleukins, parathyroid hormone, erythropoietin, transferrin, collagen, elastin, tropoelastin, exosomes, vesicles, genetic fragments, and Factor VIII. Non-limiting examples of suitable growth factors include vascular endothelial growth factor, platelet-derived growth factor, platelet-activating factor, transforming growth factors bone morphogenetic protein, activin, inhibin, fibroblast growth factors, granulocyte-colony stimulating factor, granulocyte-macrophage colony stimulating factor, glial cell line-derived neurotrophic factor, growth differentiation factor-9, epidermal growth factor, and combinations thereof.

As discussed above, the biocompatible membrane composite includes a first layer (i.e. cell impermeable layer). The cell impermeable layer serves as a microporous, immune isolation barrier, and is impervious to vascular ingrowth and prevents cellular contact from the host. Herein, layers that do not have openings large enough to allow cellular ingrowth may be referred to as "tight" layers. The pores of the cell impermeable layer are sufficiently small so as to allow the passage therethrough of cellular nutrients, oxygen, waste products, and therapeutic substances while not permitting the passage of any cells. In some embodiments, the cell impermeable layer has an MPS (maximum pore size) that is less than about 1 micron, less than about 0.50 microns, less than about 0.30 microns, or less than about 0.10 microns as measured by porometry. The MPS may be from about 0.05 microns to about 1 micron, from about 0.1 microns to about 0.80 microns, from about 0.1 microns to about 0.6 microns, from about 0.1 microns to about 0.5 microns, or from about 0.2 microns to about 0.5 microns as measured by porometry.

Because the cell impermeable layer has an MPS that is sufficiently small so as to prevent vascular ingrowth, it is necessary to balance the parameters of the cell impermeable layer that could also negatively impact the mass transport and diffusion properties of the cell impermeable layer. For instance, while the MPS is small enough to prevent cell ingress or vascular ingrowth, the cell impermeable layer is sufficiently open so as to allow the passage of molecules (i.e. nutrients and therapeutic molecules) therethrough. Diffusion resistance is further minimized by keeping the cell impermeable layer thin and porous and low in mass. It is to be appreciated that sufficient durability and strength of the cell impermeable layer be maintained so that immune isolation can be provided in vivo through an intended use by ensuring the integrity of this tight layer. Therefore, it is necessary to balance the tradeoffs of the competing properties of strength and diffusion resistance.

In some embodiments, the cell impermeable layer has a thickness less than about 10 microns, less than about 8 microns, less than about 6 microns, or less than about 4 microns. The thickness may range from about 1 micron to about 10 microns, from about 1 micron to about 8 microns, from about 1 micron to about 6 microns, from about 5 microns to about 10 microns, or from about 1 micron to about 5 microns. In addition, it is to be appreciated that sufficient porosity of the cell impermeable layer be maintained so as to allow the passage of molecules. In certain embodiments, the porosity of the cell impermeable layer is greater than about 50%, greater than about 60%, greater than about 70%, or greater than about 80%. Additionally, the porosity may range from about 50% to about 98%, from about 50% to about 90%, from about 50% to about 80%, or from about 60% to about 90%.

It is to be appreciated that sufficient durability and strength of the cell impermeable layer be maintained so that immune isolation can be provided in vivo through an intended use by ensuring the integrity of the cell impermeable layer. As the properties impacting diffusion resistance are minimized, it creates a trade-off in maintaining the necessary strength properties for integrity of the cell impermeable layer. In certain embodiments, the maximum tensile load of the weakest axis of the cell impermeable layer is greater than about 40 N/m, greater than about 130 N/m, greater than about 260 N/m, greater than about 600 N/m, or greater than about 1000 N/m. Additionally, the maximum tensile load of the weakest axis may range from about 40 N/m to about 2000 N/m, 40 N/m to about 780 N/m, 40 N/m to about 350 N/m, from about 130 N/m to about 2000 N/m, from about 130 N/m to about 450 N/m, or from about 260 N/m to about 2000 N/m.

In certain embodiments, the cell impermeable layer has a combination of tensile strengths in orthogonal directions (D1, D2) that result in a geometric mean tensile strength that is greater than about 20 MPa, greater than about 50 MPa, greater than about 100 MPa, or greater than about 150 MPa when the geometric mean tensile strength is defined by the following equation:

$$\text{Geometric Mean} = \sqrt{(\text{Tensile Strength}_{D1})^2 + (\text{Tensile Strength}_{D2})^2}.$$

Additionally, the geometric mean tensile strength of the cell impermeable layer may range from about 20 MPa to about 180 MPa, from about 30 MPa to about 150 MPa, from about 50 MPa to about 150 MPa, or from about 100 MPa to about 150 MPa.

The high intrinsic strength of the cell impermeable layer allows the cell impermeable layer to achieve the bulk strength necessary to remain retentive and robust in application while minimizing its thickness at porosities sufficient for nutrient transport. This enables cell impermeable layers with previously unobtainable combinations of thickness, porosity, and bulk strength, thereby enabling robust constructs with higher diffusion rates through reduced thickness. As discussed previously, the biocompatible membrane composite includes a second layer (i.e., mitigation layer), which is sufficiently porous to permit growth of vascular tissue into the mitigation layer, and therefore also acts as a vascularizing layer. The mitigation layer creates a suitable environment at the cell impermeable interface to minimize, reduce, inhibit, or even prevent the formation of foreign body giant cells while allowing for access to blood vessels at the cell impermeable layer. Ingrowth of vascular tissues into the mitigation layer facilitates nutrient transfer through the cell impermeable layer. Layers that have openings large enough to allow cellular ingrowth may be referred to as "open layers". Blood vessels, which are the source of oxygen and nutrients for implanted cells, need to form in the mitigation layer so that they are sufficiently close to the cell impermeable layer such that the distance for nutrient diffusion to any encapsulated cells is minimized. The thinness of the cell impermeable layer helps to reduce the distance over which diffusion must occur.

The ingrowth of vascular tissue through the mitigation layer up to the cell impermeable layer facilitates nutrient transfer across the cell impermeable layer. The mitigation layer creates an environment that enables a sufficient formation of blood vessels into the mitigation layer positioned adjacent to the cell impermeable layer instead of the formation of foreign body giant cells. As a result, and as shown in the Examples, foreign body giant cells do not form at the interface of the cell impermeable layer and the mitigation layer such that foreign body cells impede sufficient vascularization for cell survival. It is to be noted that foreign body giant cells may individually form at the interface of the cell impermeable layer and the mitigation layer, but they do not impede or prevent the vascularization needed for growth of encapsulated cells.

The mitigation layer is characterized at least in part by the inclusion of a plurality of solid features that have a solid feature spacing, which is discussed in detail below. "Solid features" as used herein may be defined as three dimensional components within the mitigation layer and are generally immovable and resistant to deformation when exposed to environmental forces, such as, but not limited to, cell movement (e.g., cellular migration and ingrowth, host vascularization/endothelial blood vessel formation). To facilitate the reduction or mitigation of the formation of a barrier of foreign body giant cells at the cell impermeable layer, the solid features abutting the surface of the cell impermeable layer adjacent to the mitigation layer help prevent the fusion of multiple macrophages into multinucleated foreign body giant cells at this interface. In some embodiments, the solid features in the mitigation layer abutting the cell impermeable layer are intimately bonded to the cell impermeable layer and are herein referred to as "bonded solid features". "Non-bonded solid features" are those solid features within the mitigation layer that are not bonded (intimately bonded or otherwise) to the cell impermeable layer.

In some embodiments, the solid features of the mitigation layer project outwardly from a plane defined by the cell impermeable layer. In such embodiments, the solid features of the mitigation layer projecting from the cell impermeable layer may be intimately bonded with the cell impermeable layer and spaced such that they provide blockades or barriers to the formation of foreign body giant cells at this tight, cell impermeable interface. In some embodiments the solid features may be a feature of the mitigation layer (e.g. nodes), and may be connected to each other, such as by fibrils or fibers. In another embodiments, the solid features may be provided and/or otherwise formed on a surface of the cell impermeable layer (e.g., printed solid features) such that the solid features project outwardly from a plane defined by the cell impermeable layer.

In embodiments where the mitigation layer has a node and fibril microstructure (e.g., formed from a fibrillated polymer), the nodes are the solid features and the fibrils are not the solid features. Indeed, in some embodiments, the fibrils may be removed, leaving only the nodes in the mitigation layer. In embodiments where the nodes within the mitigation layer are the solid features, those nodes which are bonded to the cell impermeable layer are bonded solid features. In at least one embodiment, the mitigation layer is formed of an expanded polytetrafluoroethylene (ePTFE) membrane having a node and fibril microstructure.

The solid features of the mitigation layer do not negatively impact the overall diffusion resistance of the biocompatible membrane composite for applications that require a rapid time course of diffusion. The solid features are of a sufficiently small size such that they do not interfere with the amount of porous area needed for diffusion. Also, the thickness of the mitigation layer is sufficiently thin so as to maximize mass transport of oxygen and nutrients to encapsulated cells from the interstitium during the acute period post implantation. The space between the solid features are sufficiently open to allow for easy and rapid penetration/integration of host cells and vasculature up to the cell impermeable layer (i.e., tight layer) to decrease the duration of the acute period.

Figure 1B:
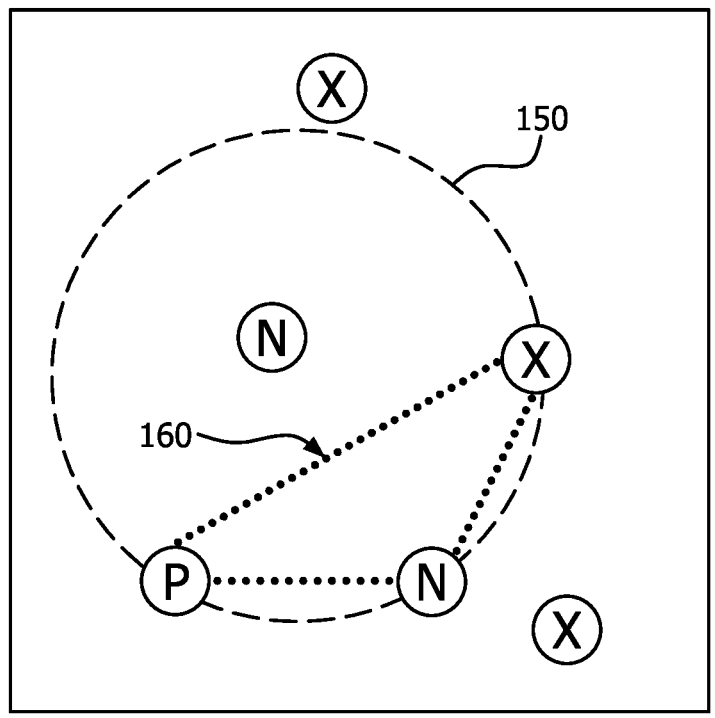
FIG. 1B is a schematic illustration depicting the determination of non-neighboring solid features where the solid features form the corners of a triangle whose circumcircle contains at least one additional solid feature in accordance with embodiments described herein.
Figure 2:
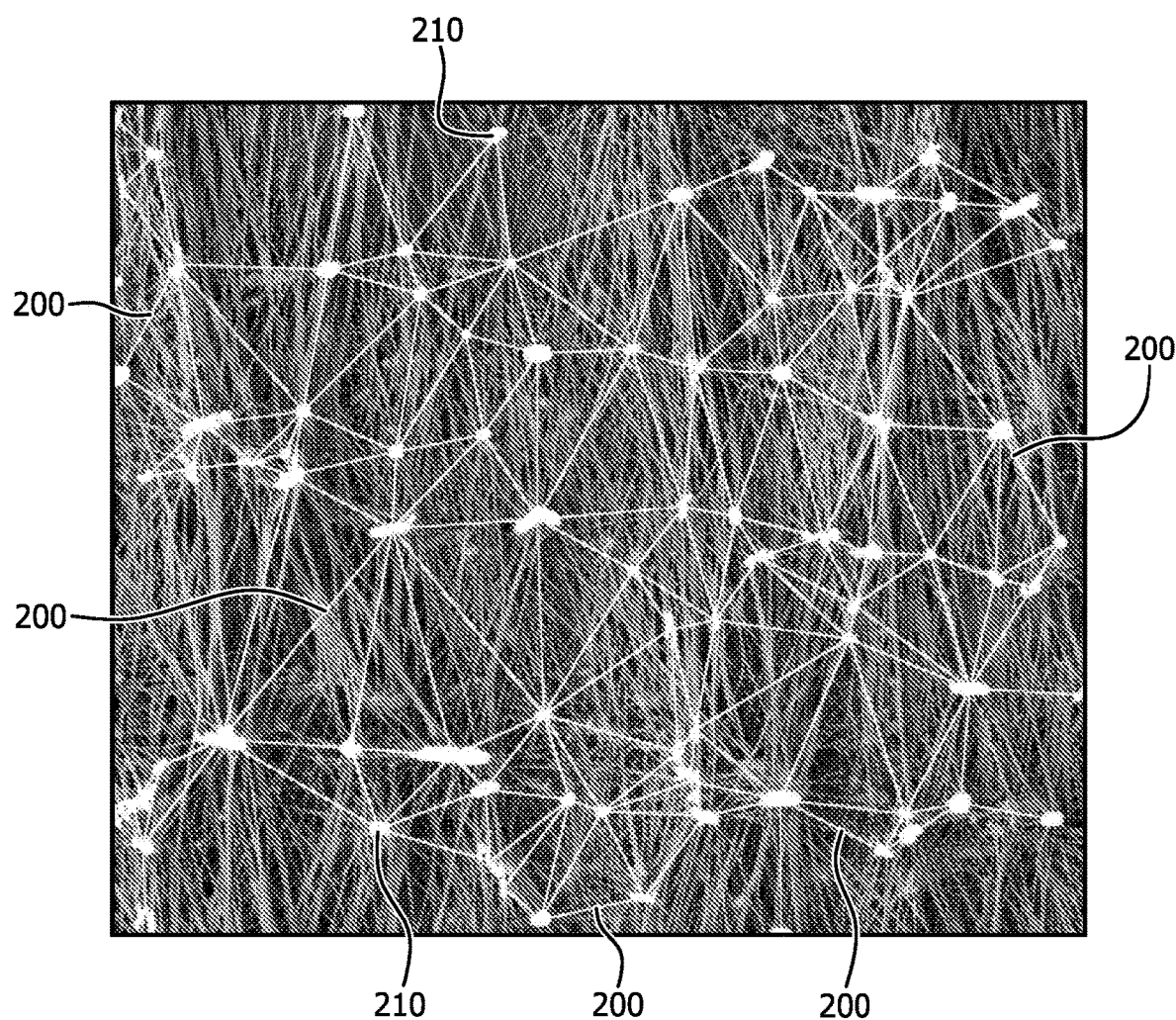
FIG. 2 is a scanning electron micrograph (SEM) image of the spacing (white lines) between solid features (white shapes) in an expanded polytetrafluoroethylene (ePTFE) membrane in accordance with embodiments described herein.

The majority of the solid feature spacing of the solid features adjacent to the cell isolating membrane is less than about 50 microns, less than about 40 microns, less than about 30 microns, less than about 20 microns, or less than about 10 microns. As used herein, the term "majority" is meant to describe an amount over half (i.e., greater than 50%) of the measured values for the parameter being measured. In some embodiments, the solid feature spacing may range from about 5 microns to about 50 microns, from about 5 microns to about 45 microns, from about 10 microns to about 40 microns, from about 10 microns to about 35 microns, or from about 15 microns to about 35 microns. The phrase "solid feature spacing" is defined herein as the straight-line distance between two neighboring solid features. In this disclosure, solid features are considered neighboring if their centroids represent the corners of a triangle whose circumcircle has an empty interior. As shown pictorially in FIG. 1A, the designated solid feature (P) is connected to neighboring solid features (N) to form a triangle 100 where the circumcircle 110 contains no solid features within. Solid features (X) designate the solid features that are not neighboring solid features. Thus, in the instance depicted in FIG. 1A, the solid feature spacing 130 is the straight distance between the designated solid features (P), (N). In contrast, the circumcircle 150 shown in FIG. 1B drawn from the triangle 160 contains therein a solid feature (N), and as such, cannot be utilized to determine the solid feature spacing in the mitigation layer. FIG. 2 is a scanning electron micrograph depicting measured distances, e.g., the white lines 200 between the solid features 210 (white shapes) in a mitigation layer formed of an expanded polytetrafluoroethylene membrane.

Figure 3A:
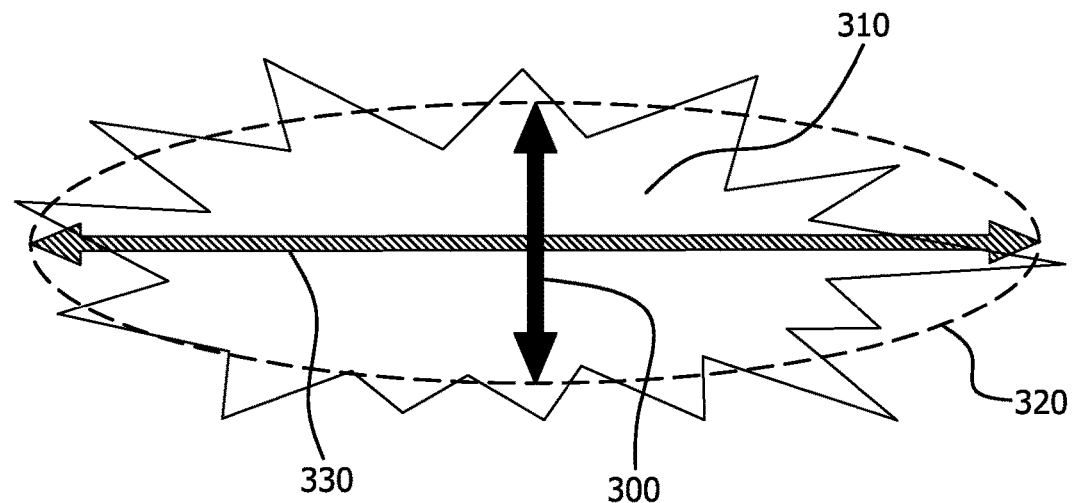
FIG. 3A is a schematic illustration depicting the method to determine the major axis and the minor axis of a solid feature in accordance with embodiments described herein.
Figure 3B:
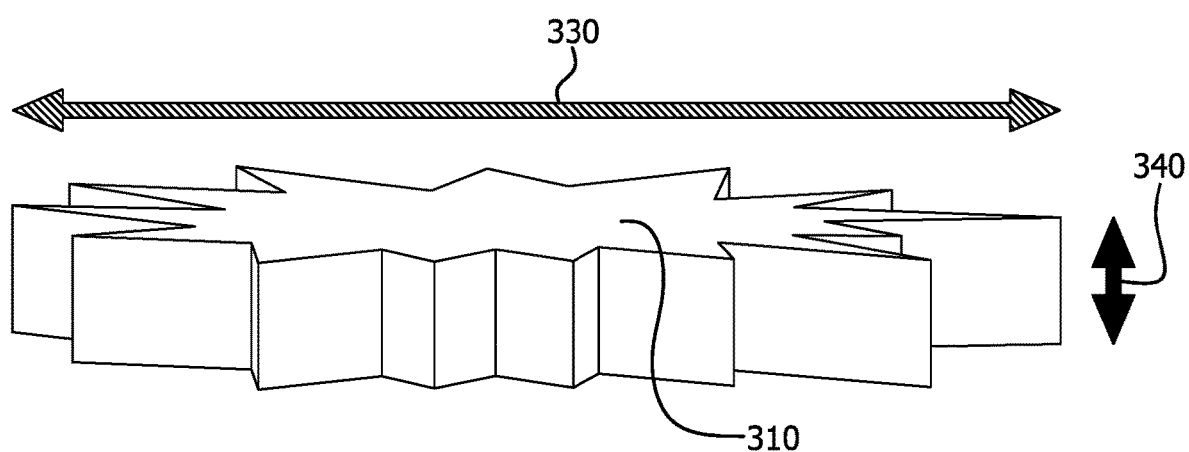
FIG. 3B is a schematic illustration depicting the depth of a solid feature in accordance with embodiments described herein.

The solid features also include a representative minor axis, a representative major axis, and a solid feature depth. The representative minor axis of a solid feature is defined herein as the length of the minor axis of an ellipse fit to the solid feature where the ellipse has the same area, orientation, and centroid as the solid feature. The representative major axis of a solid feature is defined herein as the length of the major axis of an ellipse fit to the solid feature where the ellipse has the same area, orientation, and centroid as the solid feature. The major axis is greater than or equal to the minor axis in length. The representative minor axis and representative major axis of a layer are the respective median values of all measured representative minor axes and representative major axes of features in said layer. The minor and major axes of an ellipse 320 to fit the solid feature 310 is shown pictorially in FIG. 3A. The representative minor axis of the solid feature 310 is depicted by arrow 300, and the representative major axis of the solid feature 310 is depicted by arrow 330. A majority of the solid features has a minor axis that range in size from about 3 microns to about 20 microns, from about 3 microns to about 15 microns, or from about 3 microns to about 10 microns. The solid feature depth is the length of the projection of the solid feature in the axis perpendicular to a surface of the layer (e.g., mitigation layer). The solid feature depth of a layer is the median value of all measured solid feature depths in said layer. The solid feature depth of the solid feature 310 is shown pictorially in FIG. 3B. The depth of the solid feature 310 is depicted by line 340. In at least one embodiment, the depth of the solid features is equal to or less than the thickness of the mitigation layer. In at least one embodiment, at least two of the representative minor axis, representative major axis, and solid feature depth is greater than 5 microns.

In embodiments where the solid features are interconnected by fibrils or fibers, the boundary connecting the solid features creates a pore. It is necessary that these pores are large enough to allow rapid cellular ingrowth and vascularization and not create a resistance to mass transport of oxygen and nutrients. The pore effective diameter is measured by quantitative image analysis (QIA) and performed on a scanning electron micrograph (SEM) image. The "effective diameter" of a pore is defined as the diameter of a circle that has an area equal to the measured area of the surface pore. This relationship is defined per the following equation:

$$\text{Effective Diameter} = 2 \times \sqrt{\frac{\text{Area}}{\pi}}.$$

Figure 4:
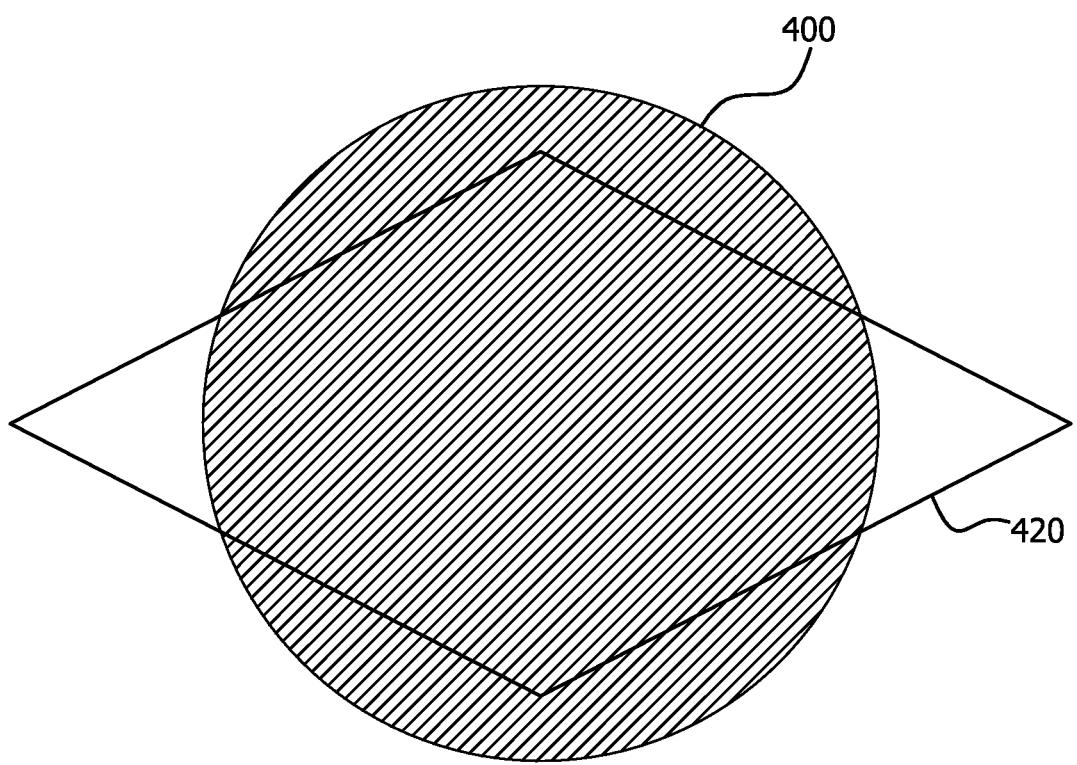
FIG. 4 is a schematic illustration of the effective diameter of a pore in accordance with embodiments described herein.
Figure 5:
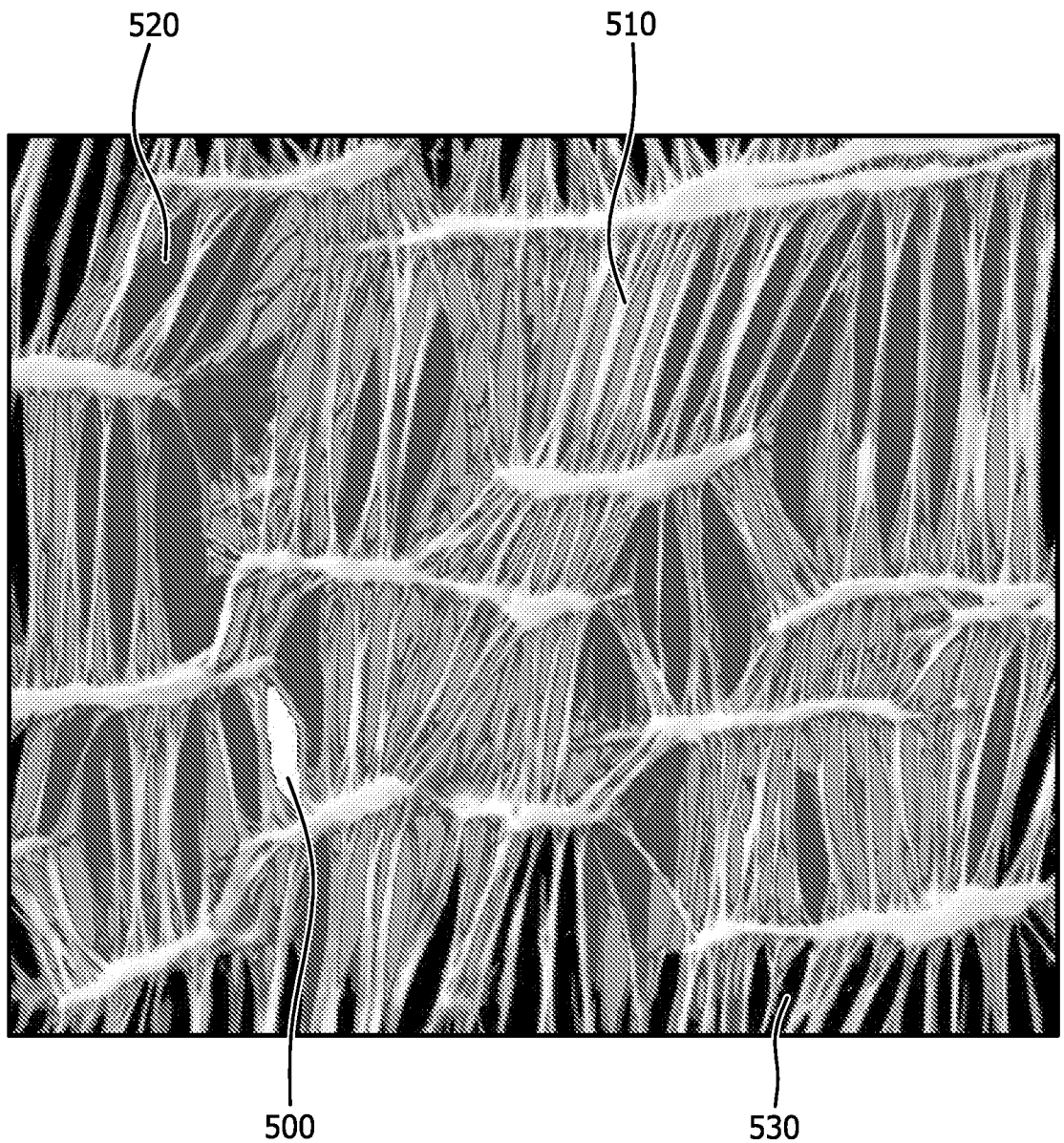
FIG. 5 is a scanning electron micrograph (SEM) image showing a pore size in accordance with embodiments described herein.

Turning to FIG. 4, the effective diameter is the diameter of the circle 400 and the surface pore is designated by reference numeral 420. The total pore area of a surface is the sum of the area of all pores at that surface. The pore size of a layer is the effective diameter of the pore that defines the point where roughly half the total pore area consists of pores with diameters smaller than the pore size and half the total pore area consists of pores with diameters greater than or equal to the pore size. FIG. 5 illustrates a pore size 500 (white in color), pores smaller in size 510 (shown in white), and pores larger in size 520 (shown in dark grey). Pores that intersect with the edge of the image 530 were excluded from analysis and are shown in black.

The pore size of the mitigation layer may range from about 1 micron to about 9 microns in effective diameter, from about 3 microns in effective diameter to about 9 microns in effective diameter, or from about 4 micron in effective diameter to about 9 microns in effective diameter as measured by quantitative image analysis (QIA) performed on an SEM image. Also, the mitigation layer has a thickness that is less than about 200 microns, less than about 290 microns, less than about 280 microns, less than about 270 microns, less than about 260 microns, less than about 200 microns, less than about 190 microns, less than about 180 microns, less than about 170 microns, less than about 160 microns, less than about 150 microns, less than about 140 microns, less than about 130 microns, less than about 120 microns, less than about 110 microns, less than about 100 microns, less than about 90 microns, less than about 80 microns, less than about 70 microns, or less than about 60 microns, less than 50 about microns, less than about 40 microns, less than about 30 microns, less than about 20 microns, or less than about 10 microns. The thickness of the mitigation layer may range from about 60 microns to about 200 microns, from about 60 microns to about 170 microns, from about 60 to about 150 microns, from about 60 microns to about 125 microns, from about 60 microns to about 100 microns, from about 3 microns to about 60 microns, from about 10 microns to about 50 microns, from about 10 microns to about 40 microns, or from about 15 microns to about 35 microns. In some embodiments, the mitigation layer has a porosity greater than about 60%. In other embodiments, the mitigation layer has a porosity greater than about 70%, greater than about 75%, greater than about 80%, or greater than about 85%. Additionally, the porosity of the mitigation layer may range from about 60% to about 90%, from about 70% to about 90%, from about 75% to about 90%, from about 80% to about 90%, or from about 80% to about 90%. In at least one embodiment, the porosity may be about 80%.

In some embodiments, the biocompatible membrane composite, including the cell impermeable layer, is perforated with discretely placed holes. The perforation size, number, and location can be selected to optimize cell function. As few as one (1) perforated hole may be present. The perforations are of a sufficient size to allow host vascular tissue (such as capillaries) to pass through the biocompatible membrane composite in order to support, for example, encapsulated pancreatic cell types. While the cell impermeable layer maintains its function as a microporous, immune isolation barrier in locations where no perforations are present, due to the discrete perforations where portions of the cell impermeable layer have been removed, the cell impermeable layer in its entirety is no longer cell impermeable because the discrete perforations allow vascular ingrowth and cellular contact from the host to pass through the biocompatible membrane composite. Because cell encapsulation device embodiments that contain a perforated cell impermeable layer allow for host immune cell contact with cells, the cells are no longer protected from immune rejection unless the host is immunocompromised or treated with immunosuppressant drugs.

Figure 9A:
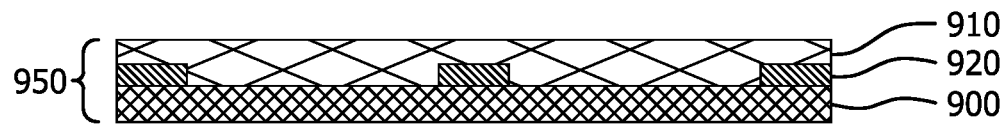
FIGS. 9A-9C are schematic illustrations of a biocompatible membrane composites showing various locations of a reinforcing component in accordance with embodiments described herein.
Figure 9B:
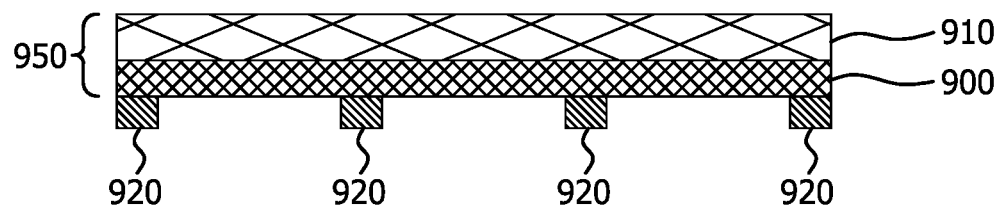
Figure 9C:
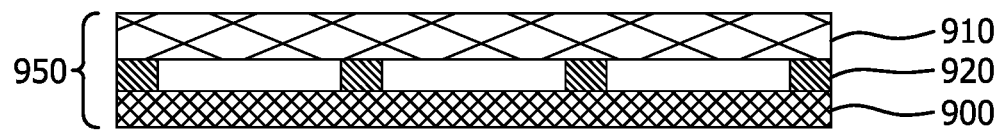

In at least one embodiment, a reinforcing component may be provided on the outer surface of the mitigation layer to strengthen the biocompatible membrane composite against environmental forces. In this orientation, the reinforcing component has a pore size sufficient to permit vascular ingrowth, and is therefore is also considered an "open" layer. Materials useful as the reinforcing component include materials that are significantly stiffer than the biocompatible membrane composite. Such materials include, but are not limited to, open mesh biomaterial textiles, woven textiles, non-woven textiles (e.g., collections of fibers or yarns), and fibrous matrices, either alone or in combination. In another embodiment, patterned grids, screens, strands and/or rods may be used as the reinforcing component. The reinforcing component may be positioned on the outer surface of cell impermeable layer (see, e.g. FIG. 9B). In this orientation, the reinforcing component may be a cell impermeable and nutrient impermeable dense layer as long as there is sufficient spacing for cells to reside between the nutrient impermeable dense layer (i.e., reinforcing component) and the cell impermeable layer. Additionally, the reinforcing component may be oriented within the mitigation layer at discrete regions (see, e.g. FIG. 9A) or the reinforcing component may be positioned between the cell impermeable layer and the mitigation layer (see, e.g. FIG. 9C). It is to be appreciated that the reinforcing component could be located externally, internally, or within the biocompatible membrane composite, or combinations thereof. Although not discussed in detail herein, it is to be appreciated that other layers (e.g. a vascularizing or vascularization layer, a mesh layer, a fabric layer, a reinforcing layer, etc.) or other reinforcing components on or within the biocompatible membrane composite are not precluded from inclusion herein and are considered to be within the purview of the invention.

In at least one embodiment, the cell impermeable layer and the mitigation layer are bonded together by one or more biocompatible adhesive to form the biocompatible membrane composite. The adhesive may be applied to the surface of one or both of the cell impermeable layer and the mitigation layer in a manner to create a discrete or intimate bond between the layers. Non-limiting examples of suitable biocompatible adhesives include fluorinated ethylene propylene (FEP), a polycarbonate urethane, a thermoplastic fluoropolymer comprised of TFE and PAVE, EFEP (ethylene fluorinated ethylene propylene), PEBAX (a polyether amide), PVDF (poly vinylidene fluoride), CarboSil® (ab-silicone polycarbonate urethane), Elasthane™ (a polyether urethane), PurSil® (a silicone polyether urethane), polyethylene, high density polyethylene (HDPE), ethylene chlorotetrafluoroethylene (ECTFE), perfluoroalkoxy (PFA), polypropylene, polyethylene terephthalate (PET), and combinations thereof. In one or more embodiment, the mitigation layer is intimately bonded to the cell impermeable layer. In other embodiments, the cell impermeable layer and the mitigation layer may be discretely bonded to each other. In some embodiments, the cell impermeable layer and the mitigation layer are co-expanded as a composite. In yet another embodiment, the cell impermeable layer may, at least in part, be bound to the mitigation layer by bonded solid features, thereby creating a discrete bond between the cell impermeable layer and the mitigation layer. In embodiments where the mitigation layer is intimately bonded to the cell impermeable layer, measured composite z-strengths may be greater than 100 kPa. Additionally, the measured composite z-strength may range from about 100 kPa to about 1300 kPa, from about 100 kPa to about 1100 kPa, from about 100 kPa to about 900 kPa, from about 100 kPa to about 700 kPa, from about 100 kPa to about 500 kPa, from about 100 kPa to about 300 kPa, or from about 100 kPa to about 200 kPa.

At least one of the cell impermeable layer and the mitigation layer may be formed of a polymer membrane or woven or non-woven collections of fibers or yarns, or fibrous matrices, either alone or in combination. Non-limiting examples of polymers that may be used one or both of the cell impermeable layer and the mitigation layer include, but are not limited to, alginate; cellulose acetate; polyalkylene glycols such as polyethylene glycol and polypropylene glycol; panvinyl polymers such as polyvinyl alcohol; chitosan; polyacrylates such as polyhydroxyethylmethacrylate; agarose; hydrolyzed polyacrylonitrile; polyacrylonitrile copolymers; polyvinyl acrylates such as polyethylene-co-acrylic acid, polyalkylenes such as polypropylene, polyethylene; polyvinylidene fluoride; fluorinated ethylene propylene (FEP); perfluoroalkoxy alkane (PFA); polyester sulfone (PES); polyurethanes; polyesters; and copolymers and combinations thereof. Examples of materials that may be used to form the mitigation layer include, but are not limited to, may include biocompatible textiles, including wovens and non-woven fabrics (e.g., a spunbound non-woven, melt blown fibrous materials, electrospun nanofibers, etc.), non-fluoropolymer membranes such as polyvinylidene difluoride (PVDF), nanofibers, polysulfones, polyethersulfones, polyarlysulfones, polyether ether ketone (PEEK), polyethylenes, polypropylenes, and polyimides. In some embodiments, a vascularization layer may be included and may be a spunbound, non-woven polyester or an expanded polytetrafluoroethylene (ePTFE) membrane.

In some embodiments at least one of the mitigation layer or reinforcing component is formed of a non-woven fabric. There are numerous types of non-woven fabrics, each of which may vary in tightness of the weave and the thickness of the sheet. The filament cross-section may be trilobal. The non-woven fabric may be a bonded fabric, a formed fabric, or an engineered fabric that is manufactured by processes other than weaving or knitting. In some embodiments, the non-woven fabric is a porous, textile-like material, usually in a flat sheet form, composed primarily or entirely of fibers, such as staple fibers assembled in a web, sheet, or batt. The structure of the non-woven fabric is based on the arrangement of, for example, staple fibers that are typically randomly arranged. In addition, non-woven fabrics can be created by a variety of techniques known in the textile industry. Various methods may create carded, wet laid, melt blown, spunbonded, or air laid non-woven materials. Non-limiting methods and substrates are described, for example, in U.S. Patent Publication No. 2010/0151575 to Colter, et al. In one embodiment the non-woven fabric is polytetrafluoroethylene (PTFE). In another embodiment the non-woven fabric is a spunbound polyester. The density of the non-woven fabric may be varied depending upon the processing conditions. In one embodiment the non-woven fabric is a spunbound polyester with a basis weight from about 0.40 to about 1.00 (oz/yd$^2$) a nominal thickness of about 127 microns to about 228 microns and a fiber diameter of about 0.5 microns to about 26 microns. The fiber cross-section may be trilobal. In some embodiments, the non-woven fabrics are biocompatible.

In some embodiments, the polymer(s) forming the cell impermeable layer and/or the mitigation layer, is a fibrillatable polymer. Fibrillatable, as used herein, refers to the ability to introduce fibrils to a polymer membrane, such as, but not limited to, converting portions of the solid features into fibrils. For example, the fibrils are the solid elements that span the gaps between the solid features. Fibrils are generally not resistant to deformation upon exposure to environmental forces, and are therefore deformable. The majority of deformable fibrils may have a diameter less than about 2 microns, less than about 1 micron, less than about 0.75 microns, less than about 0.50 microns, or less than about 0.25 microns. In some embodiments, the fibrils may have a diameter from about 0.25 microns to about 2 microns, from about 0.5 microns to about 2 microns, or from about 0.75 microns to about 2 microns.

Non-limiting examples of fibrillatable polymers that may be used to form one or more of the cell impermeable layer and the mitigation layer include, but are not limited to, tetrafluoroethylene (TFE) polymers such as polytetrafluoroethylene (PTFE), expanded PTFE (ePTFE), modified PTFE, TFE copolymers, polyvinylidene fluoride (PVDF), poly (p-xylylene) (ePPX) as taught in U.S. Patent Publication No. 2016/0032069 to Sbriglia, porous ultra-high molecular weight polyethylene (eUHMWPE) as taught in U.S. Pat. No. 9,926,416 to Sbriglia, porous ethylene tetrafluoroethylene (eETFE) as taught in U.S. Pat. No. 9,932,429 to Sbriglia, and porous vinylidene fluoride-co-tetrafluoroethylene or trifluoroethylene [VDF-co-(TFE or TrFE)] polymers as taught in U.S. Pat. No. 9,441,088 to Sbriglia, and combinations thereof.

In some embodiments, the fibrillatable polymer is a fluoropolymer membrane such as an expanded polytetrafluoroethylene (ePTFE) membrane. Expanded polytetrafluoroethylene (ePTFE) membranes have a node and fibril microstructure where the nodes are interconnected by the fibrils and the pores are the space located between the nodes and fibrils throughout the membrane. As used herein, the term "node" is mean to denote a solid feature consisting largely of polymer material. When deformable fibrils are present, these structures reside at the junction of multiple fibrils. In some embodiments, the fibrils may be removed from the membrane, such as, for example, by plasma etching.

In at least one embodiment, an expanded polytetrafluoroethylene membrane is used in one or both of the cell impermeable layer and the mitigation layer. Expanded polytetrafluoroethylene membranes such as, but not limited to, those prepared in accordance with the methods described in U.S. Pat. No. 3,953,566 to Gore, U.S. Pat. No. 7,306,729 to Bacino et al., U.S. Pat. No. 5,476,589 to Bacino, WO 94/13469 to Bacino, U.S. Pat. No. 5,814,405 to Branca et al. or U.S. Pat. No. 5,183,545 to Branca et al. may be used herein. In exemplary embodiments, one or both of the cell impermeable layer and the mitigation layer is formed of a fluoropolymer membrane, such as, but not limited to, an expanded polytetrafluoroethylene (ePTFE) membrane, a modified ePTFE membrane, a tetrafluoroethylene (TFE) copolymer membrane, a polyvinylidene fluoride (PVDF) membrane, or a fluorinated ethylene propylene (FEP) membrane.

In some embodiments, it may be desirable for the reinforcing component and/or an additional layer (e.g. a vascularization layer, a reinforcing layer, a mesh layer, a fabric layer, etc.) to be non-permeant (e.g., biodegradable). In such an instance, a biodegradable material may be used to form the reinforcing component. Suitable examples of biodegradable materials include, but are not limited to, polyglycolide: trimethylene carbonate (PGA:TMC), polyalphahydroxy acid such as polylactic acid, polyglycolic acid, poly (glycolide), and poly(lactide-co-caprolactone), poly(caprolactone), poly(carbonates), poly(dioxanone), poly (hydroxybutyrates), poly(hydroxyvalerates), poly (hydroxybutyrates-co-valerates), expanded polyparaxylylene (ePLLA), such as is taught in U.S. Patent Publication No. 2016/0032069 to Sbriglia, and copolymers and blends thereof. Alternatively, the mitigation layer may be coated with a bio-absorbable material or a bio-absorbable material may be incorporated into or onto the mitigation layer in the form of a powder. Coated materials may promote infection site reduction, vascularization, and favorable type 1 collagen deposition.

The biocompatible membrane composite may have at least partially thereon a surface coating, such as a Zwitterion non-fouling coating, a hydrophilic coating, or a CBAS®/Heparin coating (commercially available from W. L. Gore & Associates, Inc.). The surface coating may also or alternatively contain antimicrobial agents, (e.g., anti-CD 47 antibodies (anti-fibrotic)), pharmaceuticals, and other biologically active molecules (e.g., stimulators of vascularization such as FGF, VEGF, endoglin, PDGF, angiopoetins, and integrins; Anti-fibrotic such as TGFb inhibitors, sirolimus, CSF1R inhibitors, and anti CD 47 antibody; anti-inflammatory/immune modulators such as CXCL12, and corticosteroids), and combinations thereof.

An optional reinforcing component may be provided to the biocompatible membrane composite to minimize distortion in vivo so that the cell bed thickness is maintained (e.g., in an encapsulated device). This additional optional reinforcing component provides a stiffness to the biocompatible membrane composite that is greater than the biocompatible membrane composite itself to provide mechanical support. This optional reinforcing component could be continuous in nature or it may be present in discrete regions on the biocompatible membrane composite, e.g., either patterned across the entire surface of the biocompatible membrane composite or located in specific locations such as around the perimeter of the biocompatible membrane composite. Non-limiting patterns suitable for the reinforcing component on the surface of the biocompatible membrane composite include dots, straight lines, angled lines, curved lines, dotted lines, grids, etc. The patterns forming the reinforcing component may be used singly or in combination. In addition, the reinforcing component may be temporary in nature (e.g., formed of a bioabsorbable material) or permanent in nature (e.g., a polyethylene terephthalate (PET) mesh or Nitinol). As is understood by one of ordinary skill in the art, the impact of component stiffness depends not just on the stiffness of a single component, but also on the location and restraint of the reinforcing component in the final device form. In order for a component (e.g., a reinforcing component) to be practically useful for adding stiffness to the biocompatible composite membrane, the component should have a stiffness above about 0.01 N/cm, although a final determination of the stiffness needed will depend on location and restraint in the finished cell encapsulation device.

Figure 6A:
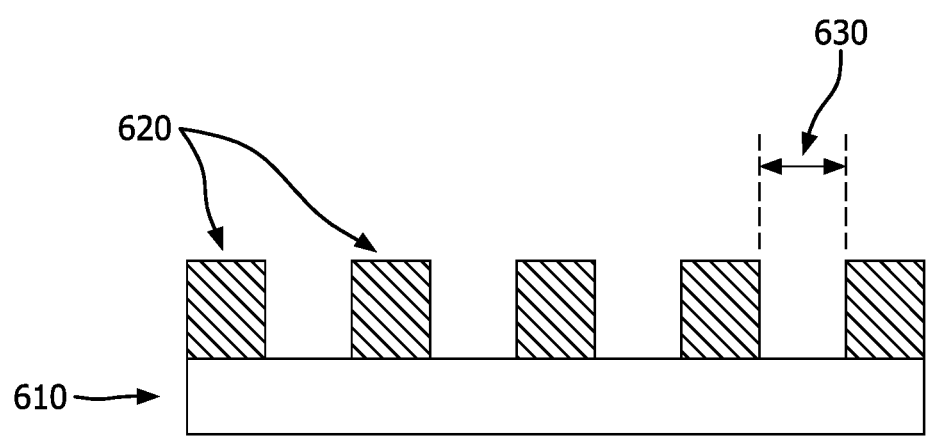
FIG. 6A is a schematic illustration of a thermoplastic polymer in the form of solid features positioned on a surface of a cell impermeable layer in accordance with embodiments described herein.
Figure 6E:
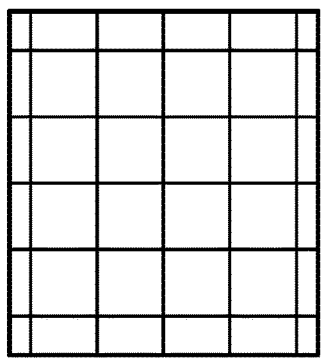
FIGS. 6B-6I are schematic illustrations of sample geometries for forming solid features on a cell impermeable layer in accordance with embodiments described herein.
Figure 6I:
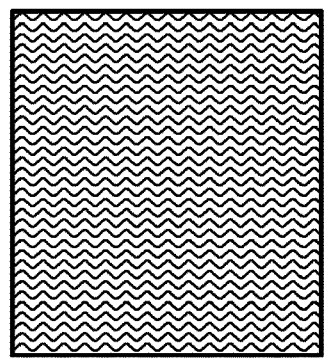
Figure 6D:
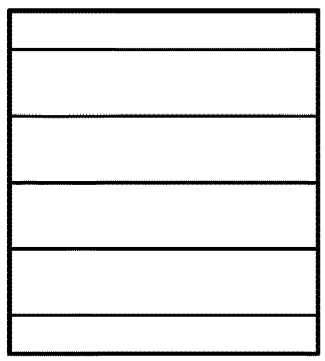
Figure 6H:
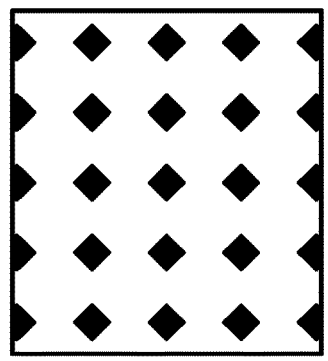
Figure 6C:
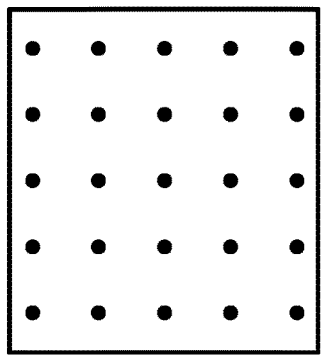
Figure 6G:
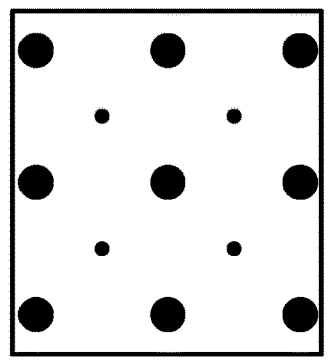
Figure 6B:
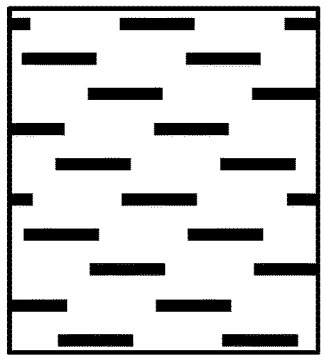
Figure 6F:
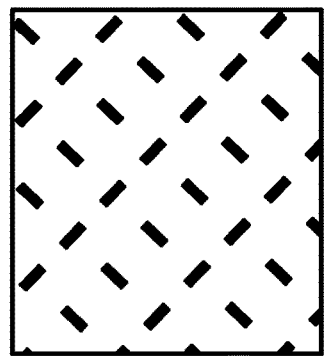

In some embodiments, the solid features of the mitigation layer may be formed by microlithography, micro-molding, machining, selectively depositing, or printing (or otherwise laying down) a polymer (e.g., thermoplastic) onto a cell impermeable layer to form at least a part of a solid feature. Any conventional printing technique such as transfer coating, screen printing, gravure printing, ink-jet printing, patterned imbibing, and knife coating may be utilized to place the thermoplastic polymer onto the cell impermeable layer. FIG. 6A illustrates a thermoplastic polymer in the form of solid features 620 positioned on a cell impermeable layer 610 (after printing is complete), where the solid features 620 have a feature spacing 630. Non-limiting examples of geometries for forming the solid features include, but are not limited to, dashed lines (see FIG. 6B) dots and/or dotted lines (see FIGS. 6C, 6G), geometric shapes (see FIG. 6H), straight lines (see FIG. 6D), angled lines (see FIG. 6F), curved lines, grids (see FIG. 6E), etc. and combinations thereof.

Materials used to form the solid features of the mitigation layer include, but are not limited to, thermoplastics, polyurethane, polypropylene, silicones, rubbers, epoxies, polyethylene, polyether amide, polyetheretherketone, polyphenylsulfone, polysulfone, silicone polycarbonate urethane, polyether urethane, polycarbonate urethane, silicone polyether urethane, polyester, polyester terephthalate, melt-processable fluoropolymers, such as, for example, fluorinated ethylene propylene (FEP), tetrafluoroethylene-(perfluoroalkyl) vinyl ether (PFA), an alternating copolymer of ethylene and tetrafluoroethylene (ETFE), a terpolymer of tetrafluoroethylene (TFE), hexafluoropropylene (HFP) and vinylidene fluoride (THV), polyvinylidene fluoride (PVDF), and combinations thereof. In some embodiments, polytetrafluoroethylene may be used to form the pattern features. In further embodiments, the solid features may be separately formed and adhered to a surface of the cell impermeable layer (not illustrated).

Figure 7A:
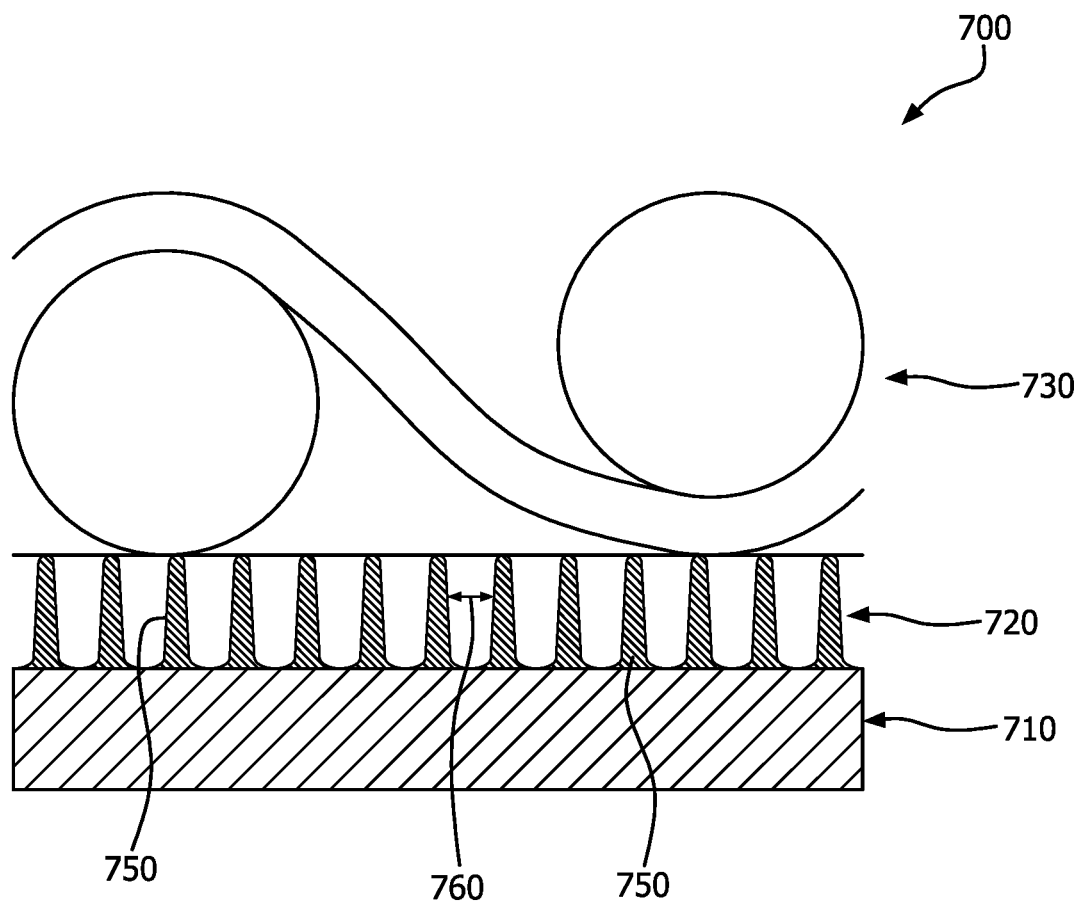
FIG. 7A is a schematic illustration of a biocompatible membrane composite having therein bonded solid features intimately bonded to a surface of the cell impermeable layer in accordance with embodiments described herein.

A biocompatible membrane composite 700 is depicted in FIG. 7A, which includes a cell impermeable layer 710, a mitigation layer 720, and an optional reinforcement layer 730. In the depicted embodiment, the solid features 750 are bonded to a surface of the cell impermeable layer 710 to form the mitigation layer 720. The solid features 750 are depicted in FIG. 7A as being essentially the same height and width and extending between the cell impermeable layer 710 and the optional reinforcement layer 730, although it is to be appreciated that this is exemplary in nature only and the solid features 750 may vary in height and/or width. The distance between solid features 750 is the solid feature spacing 760, and may, in some instances, vary between the various solid features 750.

Figure 7B:
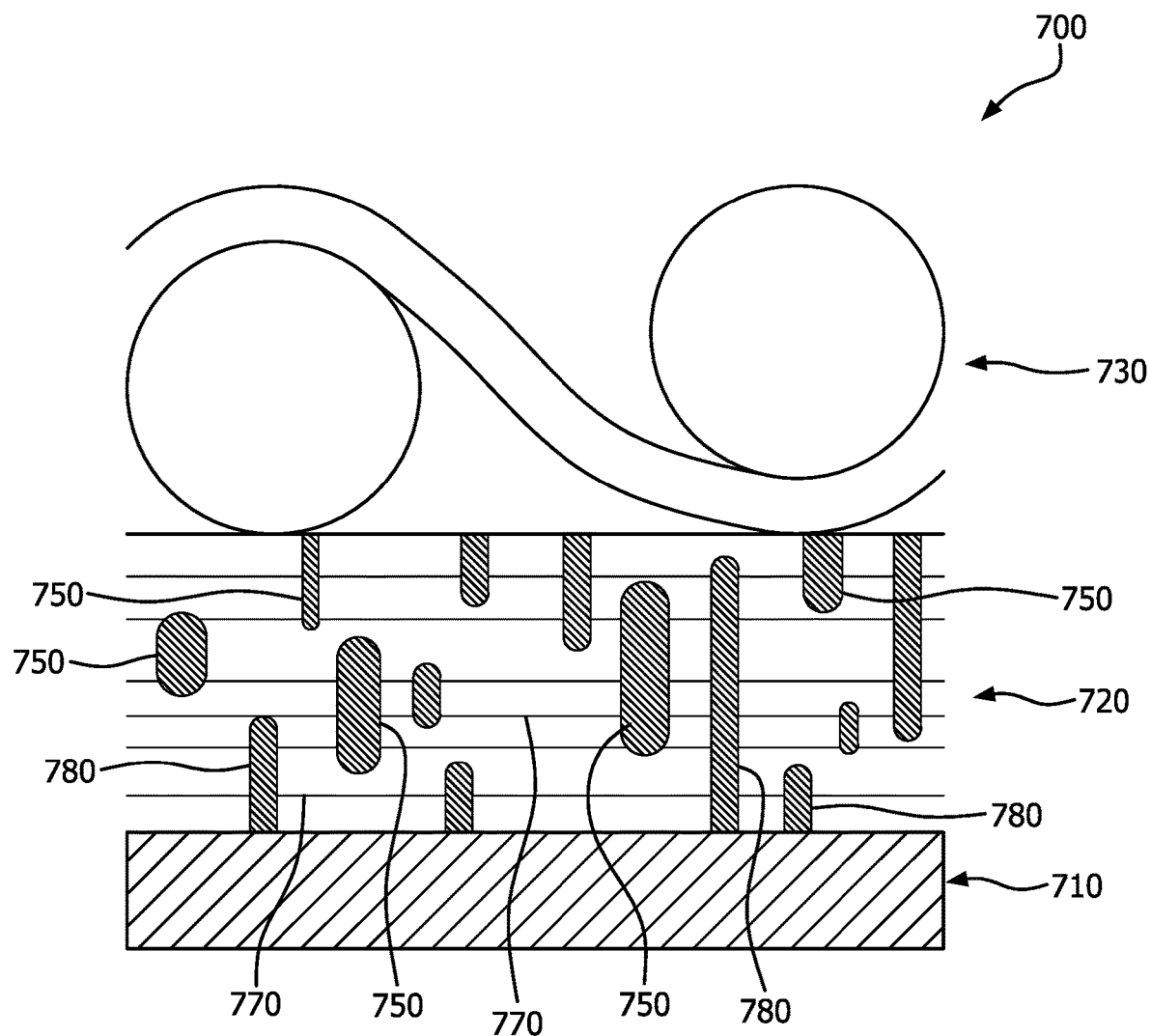
FIG. 7B is a schematic illustration of a biocompatible membrane composite where the mitigation layer has therein solid features with differing heights and widths in accordance with embodiments described herein.

FIG. 7B depicts another biocompatible composite 700 that includes a cell impermeable layer 710, a mitigation layer 720, and an optional reinforcement layer 730. In the depicted biocompatible membrane composite, the solid features 750, 780 are nodes that differ in height and width, and may or may not extend the distance between the cell impermeable layer 710 and the optional reinforcement layer 730. The solid features 750, 780 are connected by fibrils 770. In FIG. 7B, the majority of the solid feature depth is less than the thickness of the mitigation layer 720. The solid features 780 are bonded solid features.

Figure 8:
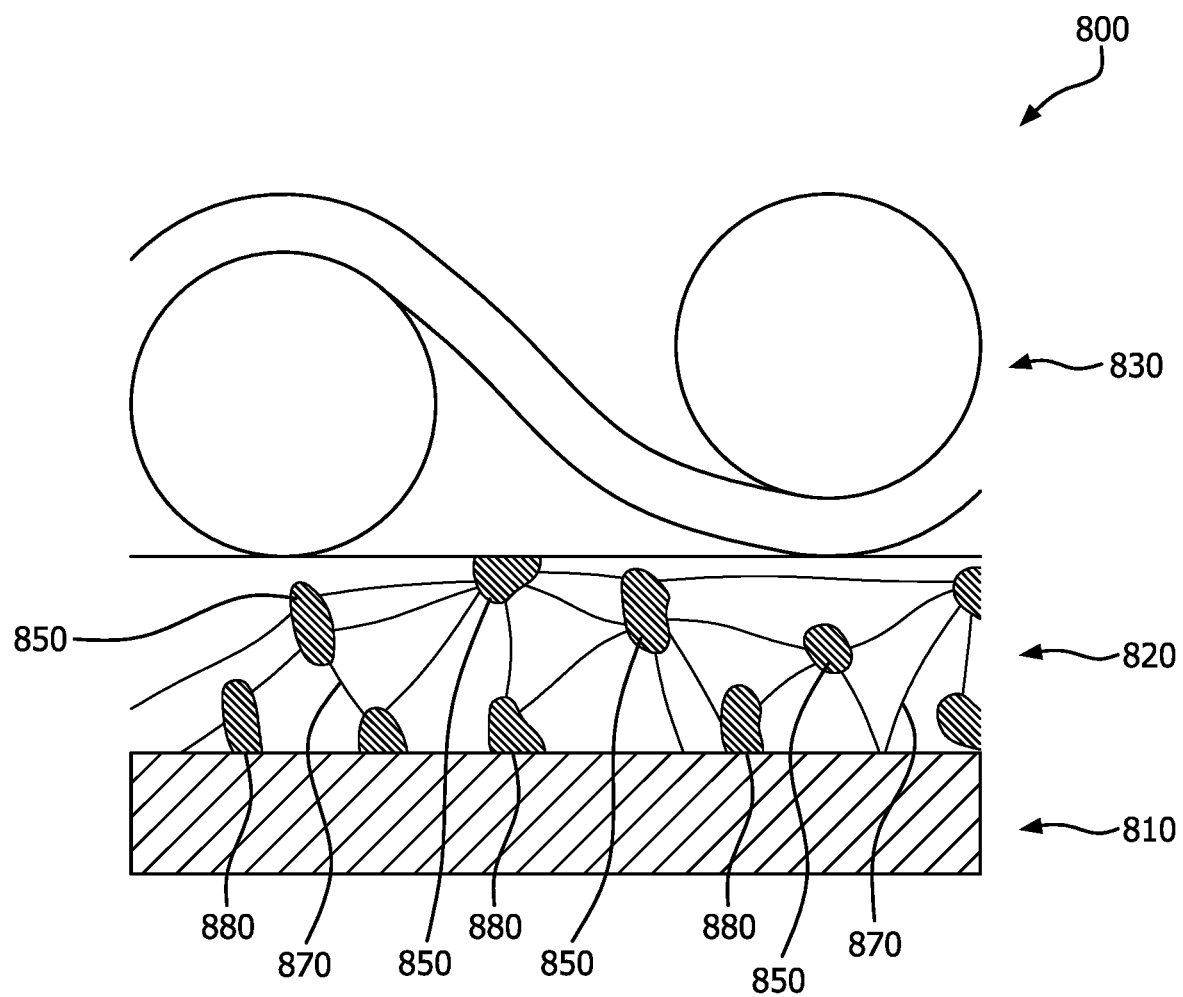
FIG. 8 is a schematic illustration of a biocompatible membrane composite having a mitigation layer containing therein solid features that are nodes in accordance with embodiments described herein.

Turning to FIG. 8, a biocompatible membrane composite containing a cell impermeable layer 810, a mitigation layer 820, and an optional reinforcement layer 830 is depicted. In this embodiment, solid features within the mitigation layer 820 are the nodes of a mitigation layer 820 that are formed in an ePTFE membrane. The nodes 850, 880 are interconnected by fibrils 870. Nodes 850 are positioned within the mitigation layer 820. Nodes 880 are not only within the mitigation layer 820, but are also in contact with, and are intimately bonded to, the cell impermeable layer 810.

As discussed above, the reinforcing component may be oriented within or between the composite layers at discrete regions. In one non-limiting embodiment shown in FIG. 9A, the reinforcing component 920 is formed as discrete regions on the inner surface of the cell impermeable layer 900 and are positioned within the mitigation layer 910 in the biocompatible membrane composite 950. In the embodiment depicted in FIG. 9B, the reinforcing component 920 is positioned on the cell impermeable layer 900 on a side opposing the mitigation layer 910 and is external to the biocompatible membrane composite 950. In yet another non-limiting embodiment depicted in FIG. 9C, the reinforcing component 920 is positioned between the cell impermeable layer 900 and the mitigation layer 910 in to the biocompatible membrane composite 950.

Figure 10:
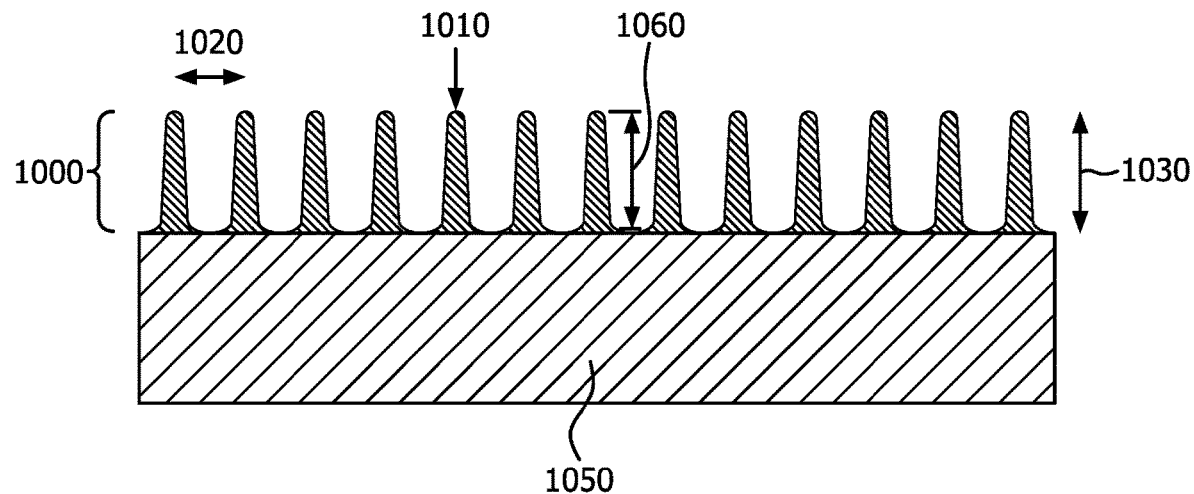
FIG. 10 is a schematic illustration of a cross-sectional view of a mitigation layer positioned on a cell impermeable layer where the mitigation layer is characterized at least by solid feature size, solid feature spacing, solid feature depth, and thickness in accordance with embodiments described herein.

In the embodiments described herein, the mitigation layer 1000 may be formed by placing or otherwise depositing a polymer in a pattern (as described above) which is characterized by one or more of the following: the solid feature size (i.e., minor axis) 1010, solid feature spacing 1020, solid feature depth 1060, thickness 1030, the absence of fibrils and/or the pore size (as measured by quantitative image analysis (QIA) performed on an SEM image) as depicted generally in FIG. 10. A cell impermeable layer 1050 is shown for reference only.

Figure 11:
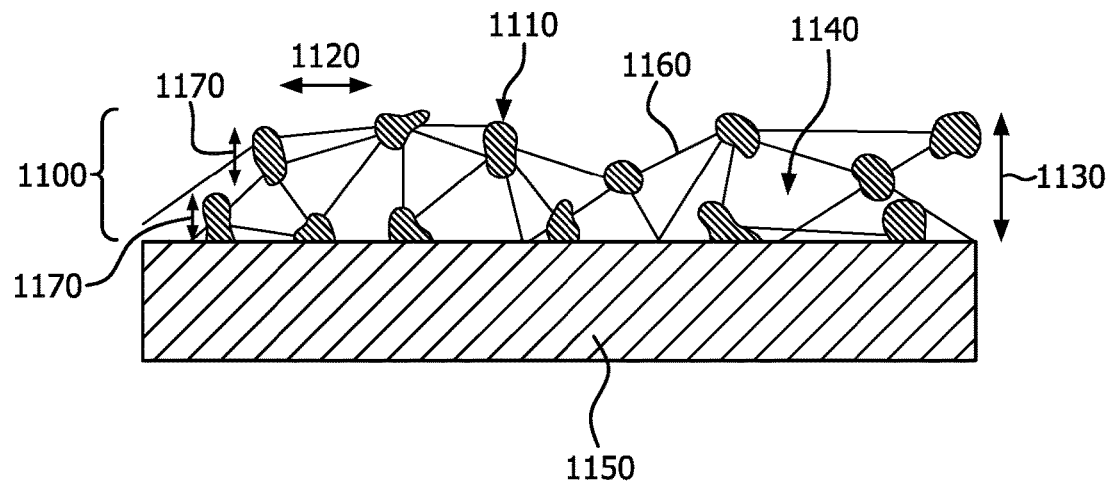
FIG. 11 is a schematic illustration of a cross-sectional view of a mitigation layer positioned on a cell impermeable layer where the mitigation layer is characterized at least by solid feature size, solid feature spacing, solid feature depth, thickness, and pore size in accordance with embodiments described herein.

FIG. 11 depicts a mitigation layer 1100 that is formed of a polymer having a node and fibril microstructure that is characterized by one or more of the following: the solid feature size (i.e., minor axis) 1110, solid feature spacing 1120, solid feature depth 1170, thickness 1130, the presence of fibrils 1160 and/or the pore size (as measured by quantitative image analysis (QIA) performed on an SEM image) 1140 as depicted generally in FIG. 11. A cell impermeable layer 1150 is shown for reference only.

Figure 12A:
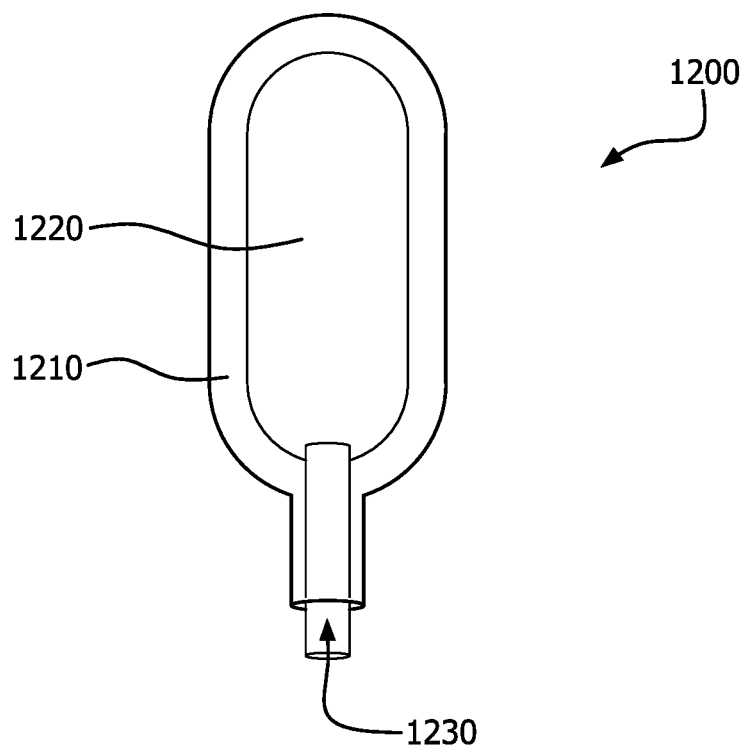
FIG. 12A is a schematic illustration of a top view of a cell encapsulation device in accordance with embodiments described herein.

The biocompatible membrane composite can be manufactured into various forms including, but not limited to, a housing, a chamber, a pouch, a tube, or a cover. In one embodiment, the biocompatible membrane composite forms a cell encapsulating device as illustrated in FIG. 12A. FIG. 12A is a top view of a cell encapsulating device 1200 formed of two layers of the biocompatible membrane composite that are sealed along a portion of their periphery 1210. Only the outer layer of the biocompatible membrane composite 1220 is shown in FIG. 12A. The cell encapsulating device 1200 includes an internal chamber, also known as a lumen (not shown) for containing cells and a port 1230 that extends into the internal chamber and is in fluid communication therewith.

Figure 12B:
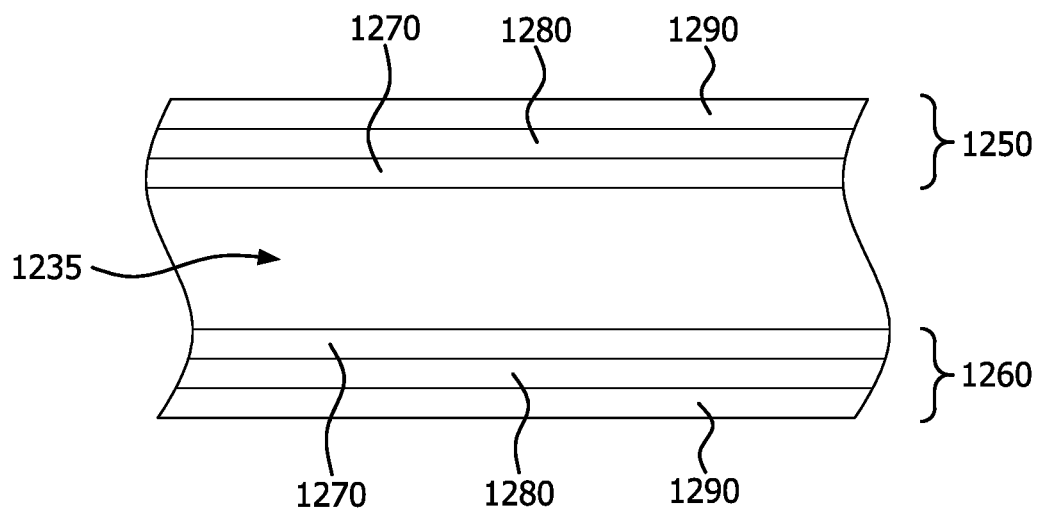
FIG. 12B is a schematic illustration of a cross-sectional illustration of the cell encapsulation device of FIG. 12A depicting an orientation of the layers of the biocompatible membrane composite and placement of cells in accordance with embodiments described herein.

FIG. 12B is a cross-sectional illustration of the cell encapsulation device of FIG. 12A. As shown, a first biocompatible membrane composite 1250 is positioned adjacent to a second biocompatible membrane composite 1260. The biocompatible membrane composites 1250, 1260 each include a cell impermeable layer (first layer) 1270 and a mitigation layer (second layer) 1280. An optional reinforcing layer (third layer) 1290 is shown. A lumen 1235 is located between the two membrane composites 1250, 1260 for the placement of cells (and/or other biologically active molecules).

Having generally described this disclosure, a further understanding can be obtained by reference to certain specific examples illustrated below which are provided for purposes of illustration only and are not intended to be all inclusive or limiting unless otherwise specified.

Test Methods
Porosity

The porosity of a layer is defined herein as the proportion of layer volume consisting of pore space compared to the total volume of the layer. The porosity is calculated by comparing the bulk density of a porous construct consisting of solid fraction and void fraction to the density of the solid fraction using the following equation:

$$\text{Porosity} = \left(1 - \frac{\text{Density}_{Bulk}}{\text{Density}_{Solid\ Fraction}}\right) \times 100\%.$$

Thickness

The thickness of the layers in the biocompatible membrane composites was measured by quantitative image analysis (QIA) of cross-sectional SEM images. Cross-sectional SEM images were generated by fixing membranes to an adhesive, cutting the film by hand using a liquid-nitrogen-cooled razor blade, and then standing the adhesive backed film on end such that the cross-section was vertical. The sample was then sputter coated using an Emitech K550X sputter coater (commercially available from Quorum Technologies Ltd, UK) and platinum target. The sample was then imaged using a FEI Quanta 400 scanning electron microscope from Thermo Scientific.

Layers within the cross-section SEM images were then measured for thickness using ImageJ 1.51 h from the National Institutes of Health (NIH). The image scale was set per the scale provided by the SEM. The layer of interest was isolated and cropped using the free-hand tool. A number of at least ten equally spaced lines were then drawn in the direction of the layer thickness. The lengths of all lines were measured and averaged to define the layer thickness.

Stiffness

A stiffness test was performed based on ASTM D790-17 Standard test method for flexural properties of unreinforced and reinforced plastics and electrical insulating material. This method was used to determine the stiffness for biocompatible membrane composite layers and/or the final cell encapsulation device.

Procedure B of the ASTM method was followed and includes greater than 5% strain and type 1 crosshead position for deflection. The dimensions of the fixture were adjusted to have a span of 16 mm and a radius of support and nosepiece of 1.6 mm. The test parameters used were a deflection of 3.14 mm and a test speed of 96.8 mm/min. In cases where the sample width differed from the standard 1 cm, the force was normalized to a 1 cm sample width by the linear ratio.

The load was reported in N/cm at maximum deflection.

Tensile Strength

Materials were tested for tensile strength using a 5500 Series Instron® Electromechanical Testing System. Unless otherwise noted, materials were tested prior to the application of any coatings. Samples were cut using a D412F or D638-V dogbone die. The samples were then loaded into the Instron® tester grips and tested at a constant rate of 20 in/min (for D412F samples) or 3 in/min (for D683-V samples) until failure. Maximum load was normalized by test area (defined as gauge width times material thickness) to define tensile stress. Materials were tested in perpendicular directions (D1 and D2) and the maximum stress in each direction was used to calculate the geometric mean tensile strength of the material per the below equation:

$$\text{Geometric Mean} = \sqrt{(\text{Tensile } Strength_{D1})^2 + (\text{Tensile } Strength_{D2})^2}.$$

Maximum Tensile Load

Materials were tested for maximum tensile load using a 5500 Series Instron® Electromechanical Testing System. Unless otherwise noted, materials were tested for prior to the application of any coatings. Samples were cut oriented in the axis of interest using a D412F or D638-V dogbone die. The samples were then loaded into the Instron® tester grips and tested at a constant rate of 20 in/min (for D412F samples) or 3 in/min (for D683-V samples) until failure. The maximum load sustained during testing was normalized by specimen gauge width (6.35 mm for D412F samples and 3.175 mm for D638-V samples) to define maximum tensile load.

Composite Bond Strength (Z-Strength)

Materials were tested for composite bond strength using a 5500 Series Instron® Electromechanical Testing System.

Unless otherwise noted, materials were tested prior to the application of any coatings. Samples were fixed to a 1"×1" (2.54 cm×2.54 cm) steel platen using 3M 9500PC double sided tape and loaded into the Instron® with an opposing 1"×1" (2.54 cm×2.54 cm) steel platen with 3M 9500PC double sided tape on its surface. A characteristic compressive load of 1001 N was applied for 60 seconds to allow adhesive to partially penetrate the structure. After this bonding, the platens were separated at a constant rate of 20 in/seconds until failure. The maximum tensile load was normalized by the test area (defined as the 1"×1" test area) to define the composite bond.

Mass/Area

Samples were cut (either by hand, laser, or die) to a known geometry. Unless otherwise noted, materials were tested prior to the application of any coatings. The dimensions of the sample were measured or verified and the area was calculated in $m^2$. The sample was then weighed in grams on a calibrated scale. The mass in grams was divided by the area in $m^2$ to calculate the mass per area in $g/m^2$.

SEM Sample Preparation

SEM samples were prepared by first fixing the membrane composite or membrane composite layer(s) of an adhesive for handling, with the side opposite the side intended for imaging facing the adhesive. The film was then cut to provide an approximately 3 mm×3 mm area for imaging. The sample was then sputter coated using an Emitech K550X sputter coater and platinum target. Images were then taken using a FEI Quanta 400 scanning electron microscope from Thermo Scientific at a magnificent and resolution that allowed visualization of a sufficient number of features for robust analysis while ensuring each feature's minimum dimension was at least five pixels in length.

Solid Feature Spacing

Solid feature spacing was determined by analyzing SEM images in ImageJ 1.51 h from the National Institute of Health (NIH). The image scale was set based on the scale provided by the SEM image. Features were identified and isolated through a combination of thresholding based on size/shading and/or manual identification. In instances where the structure consists of a continuous structure, such as a nonwoven or etched surface, as opposed to a structure with discrete solid features, solid features are defined as the portion of the structure surrounding voids the their corresponding spacing extending from one side of the void to the opposing side. After isolating the features, a Delaunay Triangulation was performed to identify neighboring features. Triangulations whose circumcircle extended beyond the edge of the image were disregarded from the analysis. Lines were drawn between the nearest edges of neighboring features and measured for length to define spacing between neighboring features (see, e.g., FIG. 1A). The solid feature spacing of a layer is the median value of all measured solid feature spacings in said layer. As such, the majority of solid feature spacings in said layer will be equal to or greater than the solid feature spacing of the layer. The median of all measured solid feature spacings marks the value that is less than or equal to half of the measured solid feature spacings and greater than or equal to half of the measured solid feature spacings. Therefore, if the measured median is above or below some value, the majority of measurements is similarly above or below said value. As such, the median is used as summary statistic to represent the majority of solid feature spacings.

Measurement of Representative Minor Axis and Representative Major Axis

The representative minor axis was measured by analyzing SEM images of membrane surfaces in ImageJ 1.51 h from the NIH. The image scale was set based on the scale provided by the SEM image. Features were identified and isolated through a combination of thresholding based on size/shading and/or manual identification. After isolating the features, the built in particle analysis capabilities were leveraged to determine the major and minor axis of the representative ellipse. The minor axis of this ellipse is the representative minor axis of the measured feature. The median of all measured minor axes marks the value that is less than or equal to half of the measured minor axes and greater than or equal to half of the measured minor axes. Similarly, the median of all measured major axes marks the value that is less than or equal to half of the measured major axes and greater than or equal to half of the measured major axes. In both cases, if the measured median is above or below some value, the majority of measurements is similarly above or below said value. As such, the median is used as summary statistic to represent the majority of solid feature representative minor axes and representative major axes.

Solid Feature Depth

Solid feature depth was determined by using quantitative image analysis (QIA) of SEM images of membrane cross-sections. Cross-sectional SEM images were generated by fixing films to an adhesive, cutting the film by hand using a liquid-nitrogen-cooled razor blade, and then standing the adhesive backed film on end such that the cross-section was vertical. The sample was then sputter coated using an Emitech K550X sputter coater (commercially available from Quorum Technologies Ltd, UK) and platinum target. The sample was then imaged using a FEI Quanta 400 scanning electron microscope from Thermo Scientific.

Features within the cross-section SEM images were then measured for depth using ImageJ 1.51 h from the National Institutes of Health (NIH). The image scale was set per the scale provided by the SEM. Features were identified and isolated through a combination of thresholding based on size/shading and/or manual identification. After isolating features, built in particle analysis capabilities were leveraged to calculate the Feret diameter and angle formed by the axis defined by the Feret diameter axis and horizontal plane for each solid feature. The Feret diameter is the furthest distance between any two points on a feature's boundary in the plane of the SEM image. The Feret diameter axis is the line defined by these two points. The projection of the Feret diameter of each solid feature in the direction of the layer thickness was calculated per the equation:

$$\text{Projection}_{Thickness} = \sin\theta * \text{Length}_{Longest\ Axis}.$$

The projection of the longest axis in the direction of the layer thickness is the solid feature depth of the measured feature. The median of all measured solid feature depths marks the value that is less than or equal to half of the measured solid feature depths and greater than or equal to half of the measured solid feature depths. Therefore, if the measured median is above or below some value, the majority of measurements is similarly above or below said value As such, the median is used as summary statistic to represent the majority of solid feature depths.

Pore Size

The pore size was measured by analyzing SEM images of membrane surfaces in ImageJ 1.51 h from the NIH. The image scale was set based on the scale provided by the SEM image. Pores were identified and isolated through a combination of thresholding based on size/shading and/or manual identification. After isolating the pores, the built in particle analysis capabilities were leveraged to determine the area of each pore. The measured pore area was converted to an "effective diameter" per the below equation:

$$\text{Effective Diameter} = 2 \times \sqrt{\frac{\text{Area}}{\pi}}$$

The pore areas were summed to define the total area of the surface defined by pores. This is the total pore area of the surface. The pore size of a layer is the effective diameter of the pore that defines the point where roughly half the total pore area consists of pores with diameters smaller than the pore size and roughly half the total pore area consists of pores with diameters greater than or equal to the pore size.

MPS (Maximum Pore Size)

MPS (maximum pore size) was measured per ASTM F316 using a Quantachrome 3Gzh porometer from Anton Paar and silicone oil (20.1 dyne/cm) as a wetting solution.

Integration of Biocompatible Membrane Composite into a Device Form

In order to evaluate the in vivo utility, various biocompatible membrane composites were manufactured into a device form suitable for use as an implantable encapsulation device for the delivery of a cell therapy. In this test form, two identical membrane composites were sealed around a perimeter region to form an open internal lumen space accessed by a fill tube or port to enable the loading of cells.

A thermoplastic film acted as the bonding component that created the perimeter seal around the device during the welding operation. The specific film used was a polycarbonate urethane film. The extruded tube had an outer diameter of 1.60 mm and an inner diameter of 0.889 mm.

Additionally, a reinforcing mechanical support having a suitable stiffness was added to the exterior of the encapsulation device. In particular, a polyester monofilament woven mesh with 120 microns fibers spaced approximately 300 microns from each other was positioned on the outside of both composite membranes (i.e., the exterior of the device). The stiffness of this layer was 0.097 N/cm.

Figure 13:
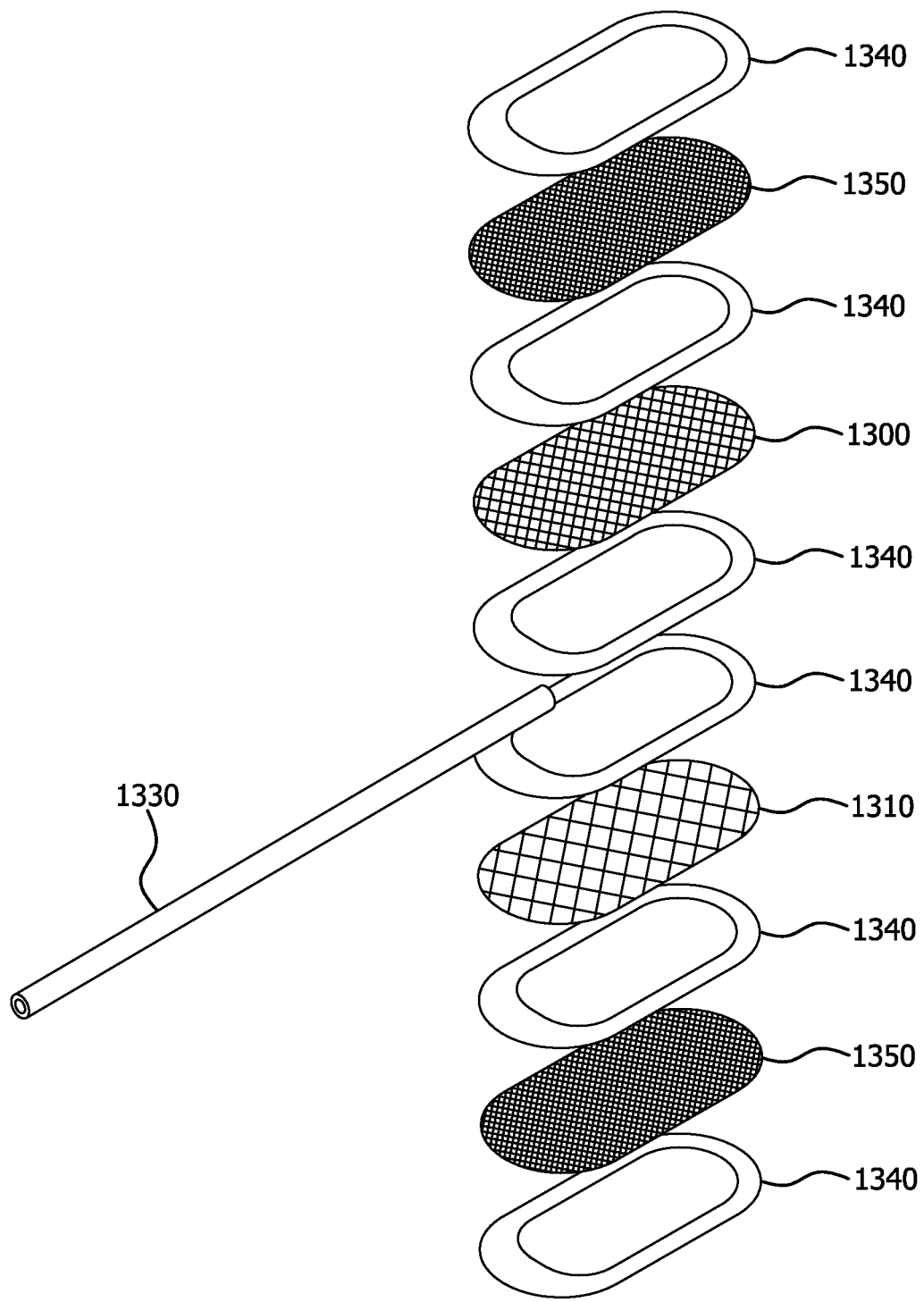
FIG. 13 is a schematic illustration of an exploded view of an exemplary encapsulation device in accordance with embodiments described herein.

All layers were cut to an approximate 22 mm×11 mm oval outer dimension size using a laser cutting table. The film was cut into oval ring profiles with a 2 mm width and placed in an intercalating stack up pattern on both sides of the biocompatible membrane composite as well as around the polyester mesh (reinforcing layer). This intercalating stack-up pattern of the components allowed for a melted film bond around each of the composite layers as well as the mesh at a perimeter location. The layers of the biocompatible membrane composite were stacked symmetrically opposing the filling tube 1330 such that the cell impermeable tight layer of the biocompatible membrane composite was facing internally towards the inner lumen. An exploded view of the encapsulation device is shown in FIG. 13. As shown in FIG. 13, the cell encapsulation device is formed a first biocompatible membrane composite 1300 sealed along a portion of its periphery to a second biocompatible membrane composite 1310 along a portion of its periphery. An inner chamber is formed between the two biocompatible membranes 1300, 1310 with access through a filling tube 1330. The cell encapsulation device may further include at least one weld film 1340 positioned at least between the first biocompatible membrane composite 1300 and a reinforcing component 1350 and between the second biocompatible membrane composite 1310 and another reinforcing component 1350. A weld film 1340 may also be used to adhere the first biocompatible membrane composite to the second biocompatible membrane composite around the peripheries thereof.

An integral perimeter seal around the device was formed by using either an ultrasonic welder (Herrmann Ultrasonics) or a thermal staking welder (Thermal Press International, Inc.). With both processes, thermal or vibrational energy and force was applied to the layered stack to melt and flow the thermoplastic film above its softening temperature to weld all the layers together. The device was constructed in a two step welding process where the energy or heat was applied from one side such that the first composite membrane was integrated into one side of the device followed by the second composite membrane onto the opposing side of the device. The final suitability of the weld was assessed by testing the device for integrity using a pressure decay test with a USON Sprint iQ Leak Tester at a test pressure of 5 PSI.

In Vivo Porcine Study to Evaluate Host Tissue Response

Sterilized, empty encapsulation devices (i.e., no cells) were sealed at the fill tube using a radio frequency (RF) welder and implanted subcutaneously in the dorsum of swine using a trocar delivery technique. After 30 days, the animals were euthanized and devices with surrounding tissue were retrieved for histological imaging.

The tissue samples were processed such that the skin and subcutaneous tissue were reflected to expose the implanted encapsulation devices. The devices were identified using digital radiography (Faxitron UltraFocus System) when needed prior to removing the encapsulation device and surrounding tissue en bloc. Device orientation was marked with staples. All explanted devices and surrounding tissue were immersed in 10% neutral buffered formalin. Each device specimen was assigned a unique accession number.

Three cross-sections were taken from each specimen. The three sections from each device were embedded together in paraffin, cut into 5-10 microns thick sections, placed on a slide and stained with hematoxylin and eosin (H&E) and Masson's Trichrome. Images of the slide were captured using a Nikon DS-Fi Series camera and Nikon NIS Elements Microscope Imaging software. At least three magnification images of each slide were captured. Measurements were taken using the Nikon NIS Elements Microscope Imaging software which is calibrated using a certified microscope micrometer and scale bars are included on each image.

In Vitro Production of Human PDX1-Positive Pancreatic Endoderm and Endocrine Cells The directed differentiation methods herein for pluripotent stem cells, for example, hES and iPS cells, can be described into at least four or five or six or seven stages, depending on end-stage cell culture or cell population desired (e.g. PDX1-positive pancreatic endoderm cell population (or PEC), or endocrine precursor cell population, or endocrine cell population, or immature beta cell population or mature endocrine cell population).

Stage 1 is the production of definitive endoderm from pluripotent stem cells and takes about 2 to 5 days, preferably 2 or 3 days. Pluripotent stem cells are suspended in media comprising RPMI, a TGFβ superfamily member growth factor, such as Activin A, Activin B, GDF-8 or GDF-11 (100 ng/mL), a Wnt family member or Wnt pathway activator, such as Wnt3a (25 ng/mL), and alternatively a rho-kinase or ROCK inhibitor, such as Y-27632 (10 μM) to enhance growth, and/or survival and/or proliferation, and/or cell-cell adhesion. After about 24 hours, the media is exchanged for media comprising RPMI with serum, such as 0.2% FBS, and a TGFβ superfamily member growth factor, such as Activin A, Activin B, GDF-8 or GDF-11 (100 ng/mL), and alternatively a rho-kinase or ROCK inhibitor for another 24 (day 1)

to 48 hours (day 2). Alternatively, after about 24 hours in a medium comprising Activin/Wnt3a, the cells are cultured during the subsequent 24 hours in a medium comprising Activin alone (i.e., the medium does not include Wnt3a). Importantly, production of definitive endoderm requires cell culture conditions low in serum content and thereby low in insulin or insulin-like growth factor content. See McLean et al. (2007) *Stem Cells* 25: 29-38. McLean et al. also show that contacting hES cells with insulin in concentrations as little as 0.2 µg/mL at Stage 1 can be detrimental to the production of definitive endoderm. Still others skilled in the art have modified the Stage 1 differentiation of pluripotent cells to definitive endoderm substantially as described here and in D'Amour et al. (2005), for example, at least, Agarwal et al., Efficient Differentiation of Functional Hepatocytes from Human Embryonic Stem Cells, Stem Cells (2008) 26:1117-1127; Borowiak et al., Small Molecules Efficiently Direct Endodermal Differentiation of Mouse and Human Embryonic Stem Cells, (2009) Cell Stem Cell 4:348-358; Brunner et al., Distinct DNA methylation patterns characterize differentiated human embryonic stem cells and developing human fetal liver, (2009) Genome Res. 19:1044-1056, Rezania et al. Reversal of Diabetes with Insulin-producing Cells Derived In Vitro from Human Pluripotent Stem Cells (2014) Nat Biotech 32(11): 1121-1133 (GDF8 & GSK3beta inhibitor, e.g. CHIR99021); and Pagliuca et al. (2014) Generation of Function Human Pancreatic B-cell In Vitro, Cell 159: 428-439 (Activin A & CHIR) Proper differentiation, specification, characterization and identification of definitive are necessary in order to derive other endoderm-lineage cells. Definitive endoderm cells at this stage co-express SOX17 and HNF3β (FOXA2) and do not appreciably express at least HNF4alpha, HNF6, PDX1, SOX6, PROX1, PTF1A, CPA, cMYC, NKX6.1, NGN3, PAX3, ARX, NKX2.2, INS, GSC, GHRL, SST, or PP. The absence of HNF4alpha expression in definitive endoderm is supported and described in detail in at least Duncan et al. (1994), Expression of transcription factor HNF-4 in the extraembryonic endoderm, gut, and nephrogenic tissue of the developing mouse embryo: HNF-4 is a marker for primary endoderm in the implanting blastocyst," *Proc. Natl. Acad. Sci,* 91:7598-7602 and Si-Tayeb et al. (2010), Highly Efficient Generation of Human Hepatocyte-Like cells from Induced Pluripotent Stem Cells," *Hepatology* 51:297-305.

Stage 2 takes the definitive endoderm cell culture from Stage 1 and produces foregut endoderm or PDX1-negative foregut endoderm by incubating the suspension cultures with RPMI with low serum levels, such as 0.2% FBS, in a 1:1000 dilution of ITS, 25 ng KGF (or FGF7), and alternatively a ROCK inhibitor for 24 hours (day 2 to day 3). After 24 hours (day 3 to day 4), the media is exchanged for the same media minus a TGFβ inhibitor, but alternatively still a ROCK inhibitor to enhance growth, survival and proliferation of the cells, for another 24 (day 4 to day 5) to 48 hours (day 6). A critical step for proper specification of foregut endoderm is removal of TGFβ family growth factors. Hence, a TGFβ inhibitor can be added to Stage 2 cell cultures, such as 2.5 µM TGFβ inhibitor no. 4 or 5 µM SB431542, a specific inhibitor of activin receptor-like kinase (ALK), which is a TGFβ type I receptor. Foregut endoderm or PDX1-negative foregut endoderm cells produced from Stage 2 co-express SOX17, HNF1B and HNF4alpha and do not appreciably co-express at leasHNF3B (FOXA2), nor HNF6, PDX1, SOX6, PROX1, PTF1A, CPA, cMYC, NKX6.1, NGN3, PAX3, ARX, NKX2.2, INS, GSC, GHRL, SST, or PP, which are hallmark of definitive endoderm, PDX1-positive pancreatic endoderm or pancreatic progenitor cells or endocrine progenitor/precursors as well as typically poly hormonal type cells.

Stage 3 (days 5-8) for PEC production takes the foregut endoderm cell culture from Stage 2 and produces a PDX1-positive foregut endoderm cell by DMEM or RPMI in 1% B27, 0.25 µM KAAD cyclopamine, a retinoid, such as 0.2 retinoic acid (RA) or a retinoic acid analog such as 3 nM of TTNPB (or CTT3, which is the combination of KAAD cyclopamine and TTNPB), and 50 ng/mL of Noggin for about 24 (day 7) to 48 hours (day 8). Specifically, Applicants have used DMEM-high glucose since about 2003 and all patent and non-patent disclosures as of that time employed DMEM-high glucose, even if not mentioned as "DMEM-high glucose" and the like. This is, in part, because manufacturers such as Gibco did not name their DMEM as such, e.g. DMEM (Cat. No 11960) and Knockout DMEM (Cat. No 10829). It is noteworthy, that as of the filing date of this application, Gibco offers more DMEM products but still does not put "high glucose" in certain of their DMEM products that contain high glucose e.g. Knockout DMEM (Cat. No. 10829-018). Thus, it can be assumed that in each instance DMEM is described, it is meant DMEM with high glucose and this was apparent by others doing research and development in this field. Again, a ROCK inhibitor or rho-kinase inhibitor such as Y-27632 can be used to enhance growth, survival, proliferation and promote cell-cell adhesion. Additional agents and factors include but are not limited to ascorbic acid (e.g. Vitamin C), BMP inhibitor (e.g. Noggin, LDN, Chordin), SHH inhibitor (e.g. SANT, cyclopamine, HIP1); and/or PKC activator (e.g. PdBu, TBP, ILV) or any combination thereof. Alternatively, Stage 3 has been performed without an SHH inhibitor such as cyclopamine in Stage 3. PDX1-positive foregut cells produced from Stage 3 co-express PDX1 and HNF6 as well as SOX9 and PROX, and do not appreciably co-express markers indicative of definitive endoderm or foregut endoderm (PDX1-negative foregut endoderm) cells or PDX1-positive foregut endoderm cells as described above in Stages 1 and 2.

The above stage 3 method is one of four stages for the production of PEC populations. For the production of endocrine progenitor/precursor and endocrine cells as described in detail below, in addition to Noggin, KAAD-cyclopamine and Retinoid; Activin, Wnt and Heregulin, thyroid hormone, TGFb-receptor inhibitors, Protein kinase C activators, Vitamin C, and ROCK inhibitors, alone and/or combined, are used to suppress the early expression NGN3 and increasing CHGA-negative type of cells.

Stage 4 (about days 8-14) PEC culture production takes the media from Stage 3 and exchanges it for media containing DMEM in 1% vol/vol B27 supplement, plus 50 ng/mL KGF and 50 ng/mL of EGF and sometimes also 50 ng/mL Noggin and a ROCK inhibitor and further includes Activin alone or combined with Heregulin. Alternatively, Stage 3 cells can be further differentiated using KGF, RA, SANT, PKC activator and/or Vitamin C or any combination thereof. These methods give rise to pancreatic progenitor cells co-expressing at least PDX1 and NKX6.1 as well as PTF1A. These cells do not appreciably express markers indicative of definitive endoderm or foregut endoderm (PDX1-negative foregut endoderm) cells as described above in Stages 1, 2 and 3.

Stage 5 production takes Stage 4 PEC cell populations above and further differentiates them to produce endocrine progenitor/precursor or progenitor type cells and/or singly and poly-hormonal pancreatic endocrine type cells in a medium containing DMEM with 1% vol/vol B27 supplement, Noggin, KGF, EGF, RO (a gamma secretase inhibitor), nicotinamide and/or ALK5 inhibitor, or any combination thereof, e.g. Noggin and ALK5 inhibitor, for about 1 to 6 days (preferably about 2 days, i.e. days 13-15). Alternatively, Stage 4 cells can be further differentiated using retinoic acid (e.g. RA or an analog thereof), thyroid hormone (e.g. T3, T4 or an analogue thereof), TGFb receptor inhibitor (ALK5 inhibitor), BMP inhibitor (e.g. Noggin, Chordin, LDN), or gamma secretase inhibitor (e.g., XXI, XX, DAPT, XVI, L685458), and/or betacellulin, or any combination thereof. Endocrine progenitor/precursors produced from Stage 5 co-express at least PDX1/NKX6.1 and also express CHGA, NGN3 and Nkx2.2, and do not appreciably express markers indicative of definitive endoderm or foregut endoderm (PDX1-negative foregut endoderm) as described above in Stages 1, 2, 3 and 4 for PEC production.

Stage 6 and 7 can be further differentiated from Stage 5 cell populations by adding any of a combination of agents or factors including but not limited to PDGF+SSH inhibitor (e.g. SANT, cyclopamine, HIP1), BMP inhibitor (e.g. Noggin, Chordin, LDN), nicotinamide, insulin-like growth factor (e.g. IGF1, IGF2), TTNBP, ROCK inhibitor (e.g. Y27632), TGFb receptor inhibitor (e.g. ALK5i), thyroid hormone (e.g. T3, T4 and analogues thereof), and/or a gamma secretase inhibitor (XXI, XX, DAPT, XVI, L685458) or any combination thereof to achieve the cell culture populations or appropriate ratios of endocrine cells, endocrine precursors and immature beta cells.

Stage 7 or immature beta cells are considered endocrine cells but may or may not me sufficiently mature to respond to glucose in a physiological manner. Stage 7 immature beta cells may express MAFB, whereas MAFA and MAFB expressing cells are fully mature cells capable of responding to glucose in a physiological manner.

Stages 1 through 7 cell populations are derived from human pluripotent stem cells (e.g. human embryonic stem cells, induced pluripotent stem cells, genetically modified stem cells e.g. using any of the gene editing tools and applications now available or later developed) and may not have their exact naturally occurring corresponding cell types since they were derived from immortal human pluripotent stem cells generated in vitro (i.e. in an artificial tissue culture) and not the inner cell mass in vivo (i.e. in vivo human development does not have an human ES cell equivalent).

Pancreatic cell therapy replacements as intended herein can be encapsulated in the described herein devices consisting of herein described membranes using any of Stages 4, 5, 6 or 7 cell populations and are loaded and wholly contained in a macro-encapsulation device and transplanted in a patient, and the pancreatic endoderm lineage cells mature into pancreatic hormone secreting cells, or pancreatic islets, e.g., insulin secreting beta cells, in vivo (also referred to as "in vivo function") and are capable of responding to blood glucose normally.

Encapsulation of the pancreatic endoderm lineage cells and production of insulin in vivo is described in detail in U.S. application Ser. No. 12/618,659 (the '659 application), entitled ENCAPSULATION OF PANCREATIC LINEAGE CELLS DERIVED FROM HUMAN PLURIPOTENT STEM CELLS, filed Nov. 13, 2009. The '659 application claims the benefit of priority to Provisional Patent Application No. 61/114,857, entitled ENCAPSULATION OF PANCREATIC PROGENITORS DERIVED FROM HES CELLS, filed Nov. 14, 2008; and U.S. Provisional Patent Application No. 61/121,084, entitled ENCAPSULATION OF PANCREATIC ENDODERM CELLS, filed Dec. 9, 2008; and now U.S. Pat. Nos. 8,278,106 and 8,424,928. The methods, compositions and devices described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

Additionally, embodiments described herein are not limited to any one type of pluripotent stem cell or human pluripotent stem cell and include but are not limited to human embryonic stem (hES) cells and human induced pluripotent stem (iPS) cells or other pluripotent stem cells later developed. It is also well known in the art, that as of the filing of this application, methods for making human pluripotent stems may be performed without destruction of a human embryo and that such methods are anticipated for production of any human pluripotent stem cell.

Methods for producing pancreatic cell lineages from human pluripotent cells were conducted substantially as described in at least the listed publications assigned to ViaCyte, Inc. including but not limited to: PCT/US2007/62755 (WO2007101130), PCT/US2008/80516 (WO2009052505), PCT/US2008/82356 (WO2010053472), PCT/US2005/28829 (WO2006020919), PCT/US2014/34425 (WO2015160348), PCT/US2014/60306 (WO2016080943), PCT/US2016/61442 (WO2018089011), PCT/US2014/15156 (WO2014124172), PCT/US2014/22109 (WO2014138691), PCT/US2014/22065 (WO2014138671), PCT/US2005/14239 (WO2005116073), PCT/US2004/43696 (WO2005063971), PCT/US2005/24161 (WO2006017134), PCT/US2006/42413 (WO2007051038), PCT/US2007/15536 (WO2008013664), PCT/US2007/05541 (WO2007103282), PCT/US2008/61053 (WO2009131568), PCT/US2008/65686 (WO2009154606), PCT/US2014/15156 (WO2014124172), PCT/US2018/41648 (WO2019014351), PCT/US2014/26529 (WO2014160413), PCT/US2009/64459 (WO2010057039); and d'Amour et al. 2005 Nature Biotechnology 23:1534-41; D'Amour et al. 2006 Nature Biotechnology 24(11):1392-401; McLean et al., 2007 Stem Cells 25:29-38, Kroon et al. 2008 Nature Biotechnology 26(4): 443-452, Kelly et al. 2011 Nature Biotechnology 29(8): 750-756, Schulz et al., 2012 PLos One 7(5):e37004; and/or Agulnick et al. 2015 Stem Cells Transl. Med. 4(10): 1214-22.

Methods for producing pancreatic cell lineages from human pluripotent cells were conducted substantially as described in at least the listed below publications assigned to Janssen including but not limited to: PCT/US2008/68782 (WO200906399), PCT/US2008/71775 (WO200948675), PCT/US2008/71782 (WO200918453), PCT/US2008/84705 (WO200970592), PCT/US2009/41348 (WO2009132063), PCT/US2009/41356 (WO2009132068), PCT/US2009/49183 (WO2010002846), PCT/US2009/61635 (WO2010051213), PCT/US2009/61774 (WO2010051223), PCT/US2010/42390 (WO2011011300), PCT/US2010/42504 (WO2011011349), PCT/US2010/42393 (WO2011011302), PCT/US2010/60756 (WO2011079017), PCT/US2011/26443 (WO2011109279), PCT/US2011/36043 (WO2011143299), PCT/US2011/48127 (WO2012030538), PCT/US2011/48129 (WO2012030539), PCT/US2011/48131 (WO2012030540), PCT/US2011/47410 (WO2012021698), PCT/US2012/68439 (WO2013095953), PCT/US2013/29360 (WO2013134378), PCT/US2013/39940 (WO2013169769), PCT/US2013/44472 (WO2013184888), PCT/US2013/78191 (WO2014106141), PCTU/S2014/38993 (WO2015065524), PCT/US2013/75939 (WO2014105543), PCT/US2013/75959 (WO2014105546), PCT/US2015/29636 (WO2015175307), PCT/US2015/64713 (WO2016100035), PCT/US2014/41988 (WO2015002724), PCT/US2017/25847 (WO2017180361), PCT/US2017/37373 (WO2017222879), PCT/US2017/37373 (WO2017222879); PCT/US2009/049049 (WO2010/002785), PCT/US2010/060770 (WO2011/079018), PCT/US2014/042796, (WO2015/065537), P CT/US2008/070418 (WO2009/012428); Bruin et al. 2013 Diabetologia. 56(9): 1987-98, Fryer et al. 2013 Curr. Opin. Endocrinol. Diabetes Obes. 20(2): 112-7, Chetty et al. 2013 Nature Methods. 10(6):553-6, Rezania et al. 2014 Nature Biotechnologyy 32(11):1121-33, Bruin et al. 2014 Stem Cell Res. 12(1): 194-208, Hrvatin 2014 Proc. Natl. Acad. Sci. USA. 111(8): 3038-43, Bruin et al. 2015 Stem Cell Reports. 5, 1081-1096, Bruin et al. 2015 Science Transl. Med., 2015, 7, 316ps23, and/or Bruin et al. 2015 Stem Cell Reports. 14; 4(4):605-20.

In one embodiment, human pluripotent cells were differentiated to PDX1-positive pancreatic endodermcells including pancreatic progenitors and endocrine precursors according to one of the preferred following conditions A and/or B.

TABLE 1

Media Conditions for PDX1-positive Pancreatic Endoderm Cell Production

| Stage | A | B |
|---|---|---|
| 1 | | r0.2FBS-ITS1:5000 A100 W50 |
| | | r0.2FBS-ITS1:5000A100 |
| 2 | | r0.2FBS-ITS1:1000 K25 IV |
| | | r0.2FBS-ITS1:1000 K25 |
| | | r0.2FBS-ITS1:1000 K25 |
| 3 | | db-TT3 N50 |
| | | db-TT3 N50 |
| | | db-TT3 N50 |
| 4 | | db-N50 K50 E50 |
| | | db-N50 K50 E50 |
| | | db-N50 K50 E50 |
| | | db-N50 K50 E50 --> Cryopreserved |
| Thaw | db-N50 K50 E50 | db-N100 A5i (1 uM) |
| (S5- | db-N50 K50 E50 | db-N100 A5i (1 uM) |
| S6) | db-N50 K50 E50 | db-N100 A5i (1 uM) |
| | | db-N100 A5i (10 uM) |
| | | db-A5i (10 uM) |
| | | db-A5i (10 uM) |

Table 1 Legend: r0.2FBS: RPMI 1640 (Mediatech); 0.2% FBS (HyClone), 1x Gluta-MAX-1 (Life Technologies), 1% v/v penicillin/streptomycin; db: DMEM Hi Glucose (HyClone) supplemented with 0.5x B-27 Supplement (Life Technologies); A100, A50, A5: 100 ng/mL recombinant human Activin A (R&D Systems); A5i: 1 uM, 5 uM, 10 uM ALK5 inhibitor; TT3: 3 nM TTNPB (Sigma-Aldrich); E50: 50 ng/mL recombinant human EGF (R&D Systems); ITS: Insulin-Transferrin-Selenium (Life Technologies) diluted 1:5000 or 1:1000; IV: 2.5 mM TGF-b RI Kinase inhibitor IV (EMD Bioscience); K50, K25: 50 ng/mL, 25 ng/mL recombinant human KGF (R&D Systems, or Peprotech); N50, N100: 50 ng/mL or 100 ng/mL recombinant human Noggin (R&D Systems); W50: 50 ng/mL recombinant mouse Wnt3A (R&D Systems).

One of ordinary skill in the art will appreciate that there may exist other methods for production of PDX1-positive pancreatic endoderm cells or PDX1-positive pancreatic endoderm lineage cells including pancreatic progenitors or even endocrine and endocrine precursor cells; and at least those PDX1-positive pancreatic endoderm cells described in Kroon et al. 2008, Rezania et al. 2014 supra and Pagliuca et al. 2014 Cell 159(2):428-439, supra.

One of ordinary skill in the art will also appreciate that the embodiments described herein for production of PDX1-positive pancreatic endoderm cells consists of a mixed population or a mixture of subpopulations. And because unlike mammalian in vivo development which occurs along the anterior-posterior axis, and cells and tissues are named such accordingly, cell cultures in any culture vessels lack such directional patterning and thus have been characterized in particular due to their marker expression. Hence, mixed subpopulations of cells at any stage of differentiation does not occur in vivo. The PDX1-positive pancreatic endoderm cell cultures therefore include, but are not limited to: i) endocrine precursors (as indicated e.g. by the early endocrine marker, Chromogranin A or CHGA); ii) singly hormonal polyhormonal cells expressing any of the typical pancreatic hormones such as insulin (INS), somatostatin (SST), pancreatic polypeptide (PP), glucagon (GCG), or even gastrin, incretin, secretin, or cholecystokinin; iii) pre-pancreatic cells, e.g. cells that express PDX-1 but not NKX6.1 or CHGA; iv) endocrine cells that co-express PDX-1/NKX6.1 and CHGA (PDX-1/NKX6.1/CHGA), or non-endocrine e.g., PDX-1/NKX6.1 but not CHGA (PDX-1+/NKX6.1+/CHA−); and v) still there are cells that do not express PDX-1, NKX6.1 or CHGA (e.g. triple negative cells).

This PDX1-positive pancreatic endoderm cells population with its mixed subpopulations of cells mostly express at least PDX-1, in particular a subpopulation that expresses PDX-1/NKX6.1. The PDX1/NKX6.1 subpopulation has also been referred to as "pancreatic progenitors", "Pancreatic Epithelium" or "PEC" or versions of PEC, e.g. PEC-01. Although Table 1 describes a stage 4 population of cells, these various subpopulations are not limited to just stage 4. Certain of these subpopulations can be for example found in as early as stage 3 and in later stages including stages 5, 6 and 7 (immature beta cells). The ratio of each subpopulation will vary depending on the cell culture media conditions employed. For example, in Agulnick et al. 2015, supra, 73-80% of PDX-1/NKX6.1 cells were used to further differentiate to islet-like cells (ICs) that contained 74-89% endocrine cells generally, and 40-50% of those expressed insulin (INS). Hence, different cell culture conditions are capable of generating different ratios of subpopulations of cells and such may effect in vivo function and therefore blood serum c-peptide levels. And whether modifying methods for making PDX1-positive pancreatic endoderm lineage cell culture populations effects in vivo function can only be determined using in vivo studies as described in more detail below. Further, it cannot be assumed and should not be assumed that just because a certain cell type has been made and has well characterized, that such a method produces the same cell intermediates, unless this is also well characterized.

In one aspect, a method for producing mature beta cells in vivo is provided. The method consisting of making human definitive endoderm lineage cells derived from human pluripotent stem cells in vitro with at least a TGFβ superfamily member and/or at least a TGFβ superfamily member and a Wnt family member, preferably a TGFβ superfamily member and a Wnt family member, preferably Activin A, B or GDF-8, GDF-11 or GDF-15 and Wnt3a, preferably Actvin A and Wnt3a, preferably GDF-8 and Wnt3a. The method for making PDX1-positive pancreatic endoderm cells from definitive endoderm cells with at least KGF, a BMP inhibitor and a retinoic acid (RA) or RA analog, and preferably with KGF, Noggin and RA. The method may further differentiate the PDX1-positive pancreatic endoderm cells into immature beta cells or MAFA expressing cells with a thyroid hormone and/or a TGFb-RI inhibitor, a BMP inhibitor, KGF, EGF, a thyroid hormone, and/or a Protein Kinase C activator; preferably with noggin, KGF and EGF, preferably additionally with T3 or T4 and ALK5 inhibitor or T3 or T4 alone or ALK5 inhibitor alone, or T3 or T4, ALK5 inhibitor and a PKC activator such as ILV, TPB and PdBu. Or preferably with noggin and ALK5i and implanting and maturing the PDX1-positive pancreatic endoderm cells or the MAFA immature beta cell populations into a mammalian host in vivo to produce a population of cells including insulin secreting cells capable of responding to blood glucose.

In one aspect, a unipotent human immature beta cell or PDX1-positive pancreatic endoderm cell that expresses INS and NKX6.1 and does not substantially express NGN3 is provided. In one embodiment, the unipotent human immature beta cell is capable of maturing to a mature beta cell. In one embodiment, the unipotent human immature beta cell further expresses MAFB in vitro and in vivo. In one embodiment, the immature beta cells express INS, NKX6.1 and MAFA and do not substantially express NGN3.

In one aspect, pancreatic endoderm lineage cells expressing at least CHGA (or CHGA+) refer to endocrine cells; and pancreatic endoderm cells that do not express CHGA (or CHGA−) refer to non-endocrine cells. In another aspect, these endocrine and non-endocrine sub-populations may be multipotent progenitor/precursor sub-populations such as non-endocrine multipotent pancreatic progenitor sub-populations or endocrine multipotent pancreatic progenitor sub-populations; or they may be unipotent sub-populations such as immature endocrine cells, preferably immature beta cells, immature glucagon cells and the like.

In one aspect, more than 10% preferably more than 20%, 30%, 40% and more preferably more than 50%, 60%, 70%, 80%, 90%, 95%, 98% or 100% of the cells in the pancreatic endoderm or PDX1-positive pancreatic endoderm cell population (stage 4) are the non-endocrine (CHGA−) multipotent progenitor sub-population that give rise to mature insulin secreting cells and respond to glucose in vivo when implanted into a mammalian host.

One embodiment provides a composition and method for differentiating pluripotent stem cells in vitro to substantially pancreatic endoderm cultures and further differentiating the pancreatic endoderm culture to endocrine or endocrine precursor cells in vitro. In one aspect, the endocrine precursor or endocrine cells express CHGA. In one aspect, the endocrine cells can produce insulin in vitro. In one aspect, the in vitro endocrine insulin secreting cells may produce insulin in response to glucose stimulation. In one aspect, more than 10% preferably more than 20%, 30%, 40% and more preferably more than 50%, 60%, 70%, 80%, 90%, 95%, 98% or 100% of the cells in the cells population are endocrine cells.

Embodiments described herein provide for compositions and methods of differentiating pluripotent human stem cells in vitro to endocrine cells. In one aspect, the endocrine cells express CHGA. In one aspect, the endocrine cells can produce insulin in vitro. In one aspect, the endocrine cells are immature endocrine cells such as immature beta cells. In one aspect, the in vitro insulin producing cells may produce insulin in response to glucose stimulation.

One embodiment provides a method for producing insulin in vivo in a mammal, said method comprising: (a) loading a pancreatic endoderm cell or endocrine cell or endocrine precursor cell population into an implantable semi-permeable device; (b) implanting the device with the cell population into a mammalian host; and (c) maturing the cell population in said device in vivo wherein at least some of the endocrine cells are insulin secreting cells that produce insulin in response to glucose stimulation in vivo, thereby producing insulin in vivo to the mammal. In one aspect the endocrine cell is derived from a cell composition comprising PEC with a higher non-endocrine multipotent pancreatic progenitor sub-population (CHGA−). In another aspect, the endocrine cell is derived from a cell composition comprising PEC with a reduced endocrine sub-population (CHGA+). In another aspect, the endocrine cell is an immature endocrine cell, preferably an immature beta cell.

In one aspect the endocrine cells made in vitro from pluripotent stem cells express more PDX1 and NKX6.1 as compared to PDX-1 positive pancreatic endoderm populations, or the non-endocrine (CHGA−) subpopulations which are PDX1/NKX6.1 positive. In one aspect, the endocrine cells made in vitro from pluripotent stem cells express PDX1 and NKX6.1 relatively more than the PEC non-endocrine multipotent pancreatic progenitor sub-population (CHGA−). In one aspect, a Bone Morphogenic Protein (BMP) and a retinoic acid (RA) analog alone or in combination are added to the cell culture to obtain endocrine cells with increased expression of PDX1 and NKX6.1 as compared to the PEC non-endocrine multipotent progenitor sub-population (CHGA−). In one aspect BMP is selected from the group comprising BMP2, BMP5, BMP6, BMP7, BMP8 and BMP4 and more preferably BMP4. In one aspect the retinoic acid analog is selected from the group comprising all-trans retinoic acid and TTNPB (4-[(E)-2-(5,6,7,8-Tetrahydro-5,5,8,8-tetramethyl-2-naphthalenyl)-1-propenyl]benzoic acid Arotinoid acid), or 0.1-10 µM AM-580 (4-[(5,6,7,8-Tetrahydro-5,5,8,8-tetramethyl-2-naphthalenyl)carboxamido]benzoic acid) and more preferably TTNPB.

One embodiment provides a method for differentiating pluripotent stem cells in vitro to endocrine and immature endocrine cells, preferably immature beta cells, comprising dissociating and re-associating the aggregates. In one aspect the dissociation and re-association occurs at stage 1, stage 2, stage 3, stage 4, stage 5, stage 6 or stage 7 or combinations thereof. In one aspect the definitive endoderm, PDX1-negative foregut endoderm, PDX1-positive foregut endoderm, PEC, and/or endocrine and endocrine progenitor/precursor cells are dissociated and re-associated. In one aspect, the stage 7 dissociated and re-aggregated cell aggregates consist of fewer non-endocrine (CHGA−) sub-populations as compared to endocrine (CHGA+) sub-populations. In one aspect, more than 10% preferably more than 20%, 30%, 40% and more preferably more than 50%, 60%, 70%, 80%, 90%, 95%, 98% or 100% of the cells in the cell population are endocrine (CHGA+) cells.

One embodiment provides a method for differentiating pluripotent stem cells in vitro to endocrine cells by removing the endocrine cells made during stage 4 PEC production thereby enriching for non-endocrine multipotent pancreatic progenitor (CHGA−) sub-population which is PDX1+ and NKX6.1+.

In one embodiment, PEC cultures enriched for the non-endocrine multipotent progenitor sub-population (CHGA−) are made by not adding a Noggin family member at stage 3 and/or stage 4. In one embodiment, PEC cultures which are relatively replete of cells committed to the endocrine lineage (CHGA+) are made by not adding a Noggin family member at stage 3 and/or stage 4. In one aspect the Noggin family member is a compound selected from the group comprising Noggin, Chordin, Follistatin, Folistatin-like proteins, Cerberus, Coco, Dan, Gremlin, Sclerostin, PRDC (protein related to Dan and Cerberus).

One embodiment provides a method for maintaining endocrine cells in culture by culturing them in a media comprising exogenous high levels of glucose, wherein the exogenous glucose added is about 1 mM to 25 mM, about 1 mM to 20 mM, about 5 mM to 15 mM, about 5 mM to 10 mM, about 5 mM to 8 mM. In one aspect, the media is a DMEM, CMRL or RPMI based media.

One embodiment provides a method for differentiating pluripotent stem cells in vitro to endocrine cells with and without dissociating and re-associating the cell aggregates. In one aspect the non-dissociated or the dissociated and re-associated cell aggregates are cryopreserved or frozen at stage 6 and/or stage 7 without affecting the in vivo function of the endocrine cells. In one aspect, the cryopreserved endocrine cell cultures are thawed, cultured and, when transplanted, function in vivo.

Another embodiment provides a culture system for differentiating pluripotent stem cells to endocrine cells, the culture system comprising of at least an agent capable of suppressing or inhibiting endocrine gene expression during early stages of differentiation and an agent capable of inducing endocrine gene expression during later stages of differentiation. In one aspect, an agent capable of suppressing or inhibiting endocrine gene expression is added to the culture system consisting of pancreatic PDX1 negative foregut cells. In one aspect, an agent capable of inducing endocrine gene expression is added to the culture system consisting of PDX1-positive pancreatic endoderm progenitors or PEC. In one aspect, an agent capable of suppressing or inhibiting endocrine gene expression is an agent that activates a TGFbeta receptor family, preferably it is Activin, preferably, it is high levels of Activin, followed by low levels of Activin. In one aspect, an agent capable of inducing endocrine gene expression is a gamma secretase inhibitor selected from a group consisting of N—[N-(3,5-Difluro-phenacetyl-L-alanyl)]-S-phenylglycine t-Butyl Ester (DAPT), RO44929097, DAPT (N—[N-(3,5-Difluorophen-acetyl-L-alanyl)]-S-phenylglycine t-Butyl Ester), 1-(S)-endo-N-(1,3,3)-Trimethylbicyclo[2.2.1]hept-2-yl)-4-fluoro-phenyl Sulfonamide, WPE-III31C, S-3-[N'-(3,5-difluorophenyl-alpha-hydroxyacetyl)-L-alanilyl]amino-2,3-dih-ydro-1-methyl-5-phenyl-1H-1,4-benzodiazepin-2-one, (N)—[(S)-2-hydroxy-3-methyl-butyryl]-1-(L-alaninyl)-(S)-1-amino-3-methyl-4,5,6,7-tetrahydro-2H-3-benzazepin-2-one, BMS-708163 (Avagacestat), BMS-708163, Semagacestat (LY450139), Semagacestat (LY450139), MK-0752, MK-0752, YO-01027, YO-01027 (Dibenzazepine, DBZ), LY-411575, LY-411575, or LY2811376. In one aspect, high levels of Activin is meant levels greater than 40 ng/mL, 50 ng/mL, and 75 ng/m L. In one aspect, high levels of Activin are used during stage 3 or prior to production of pancreatic foregut endoderm cells. In one aspect, low levels of Activin means less than 30 ng/mL, 20 ng/mL, 10 ng/mL and 5 ng/m L. In one aspect, low levels of Activin are used during stage 4 or for production of PEC. In one aspect, the endocrine gene that is inhibited or induced is NGN3. In another aspect, Activin A and Wnt3A are used alone or in combination to inhibit endocrine expression, preferably to inhibit NGN3 expression prior to production of pancreatic foregut endoderm cells, or preferably during stage 3. In one aspect, a gamma secretase inhibitor, preferably RO44929097 or DAPT, is used in the culture system to induce expression of endocrine gene expression after production of PEC, or preferably during stages 5, 6 and/or 7.

An in vitro cell culture comprising endocrine cells wherein at least 5% of said human cells express an endocrine marker selected from the group consisting of, insulin (INS), NK6 homeobox 1 (NKX6.1), pancreatic and duodenal homeobox 1 (PDX1), transcription factor related locus 2 (NKX2.2), paired box 4 (PAX4), neurogenic differentiation 1 (NEUROD), forkhead box A1 (FOXA1), forkhead box A2 (FOXA2), snail family zinc finger 2 (SNAIL2), and musculoaponeurotic fibrosarcoma oncogene family A and B (MAFA and MAFB), and does not substantially express a marker selected from the group consisting of neurogenin 3 (NGN3), islet 1 (ISL1), hepatocyte nuclear factor 6 (HNF6), GATA binding protein 4 (GATA4), GATA binding protein 6 (GATA6), pancreas specific transcription factor 1a (PTF1A) and SRY (sex determining region Y)-9 (SOX9), wherein said endocrine cells are unipotent and can mature to pancreatic beta cells.

In Vivo Nude Rate Study to Evaluate Functional Response

The encapsulation devices were loaded ex vivo with about $6-7 \times 10^6$ cells (or about 20 µL) of pancreatic progenitor cells as described in at least the teachings of U.S. Pat. No. 8,278,106 to Martinson, et. al. After being held in media for less than 24-96 hours, two devices were implanted subcutaneously in each male immunodeficient athymic nude rat. The pancreatic progenitor cells were allowed to develop and mature in vivo and functional performance of the grafts was measured by performing glucose stimulated insulin secretion (GSIS) assays at 12, 16, 20 and 23-24 weeks post-implant.

GSIS Assay and Measurement of C-Peptide Secretion

Animals that had been implanted with encapsulated pancreatic progenitor cells underwent glucose stimulated insulin secretion assays at 12, 16, 20 and 23-24 weeks post device implantation to monitor graft function. Animals were fasted for 4-16 hours and blood samples were taken via jugular vein venupuncture prior to glucose administration at a dose of 3 g/kg body weight via intraperitoneal injection of a sterile 30% glucose solution. Blood samples were again drawn at 90 minutes, or 60 and 90 minutes, or 30 and 60 minutes after glucose administration. Serum was separated from the whole blood and then assayed for human c-peptide using a commercially available ELISA kit (Mercodia, catalog #10-1141-01, Uppsala Sweden). Beta-cells co-release c-peptide with insulin from pro-insulin in an equimolar ratio and c-peptide is measured as a surrogate for insulin secretion due to its longer half-life in blood.

Nude Rat Explant Histology

At indicated time points post implant, nude rats were euthanized and devices were explanted. Excess tissue was trimmed away and devices were placed in neutral buffered 10% formalin for about 6-30 hours. Fixed devices were processed for paraffin embedding in a Leica Biosystems ASP300S tissue processor. Processed devices were cut into 4-6 pieces of approximately 5 mm each and embedded together in paraffin blocks. Multiple 3-10 micron cross sections were cut from each block, place on slides and stained with hematoxylin and eosin (H&E). Images of the slides were captured using a Hamamatsu Nanozoomer 2.0-HT Digital Slide Scanner.

EXAMPLES

Comparative Example 1

Manufacturing of Biocompatible Membrane Composite

Figure 14:
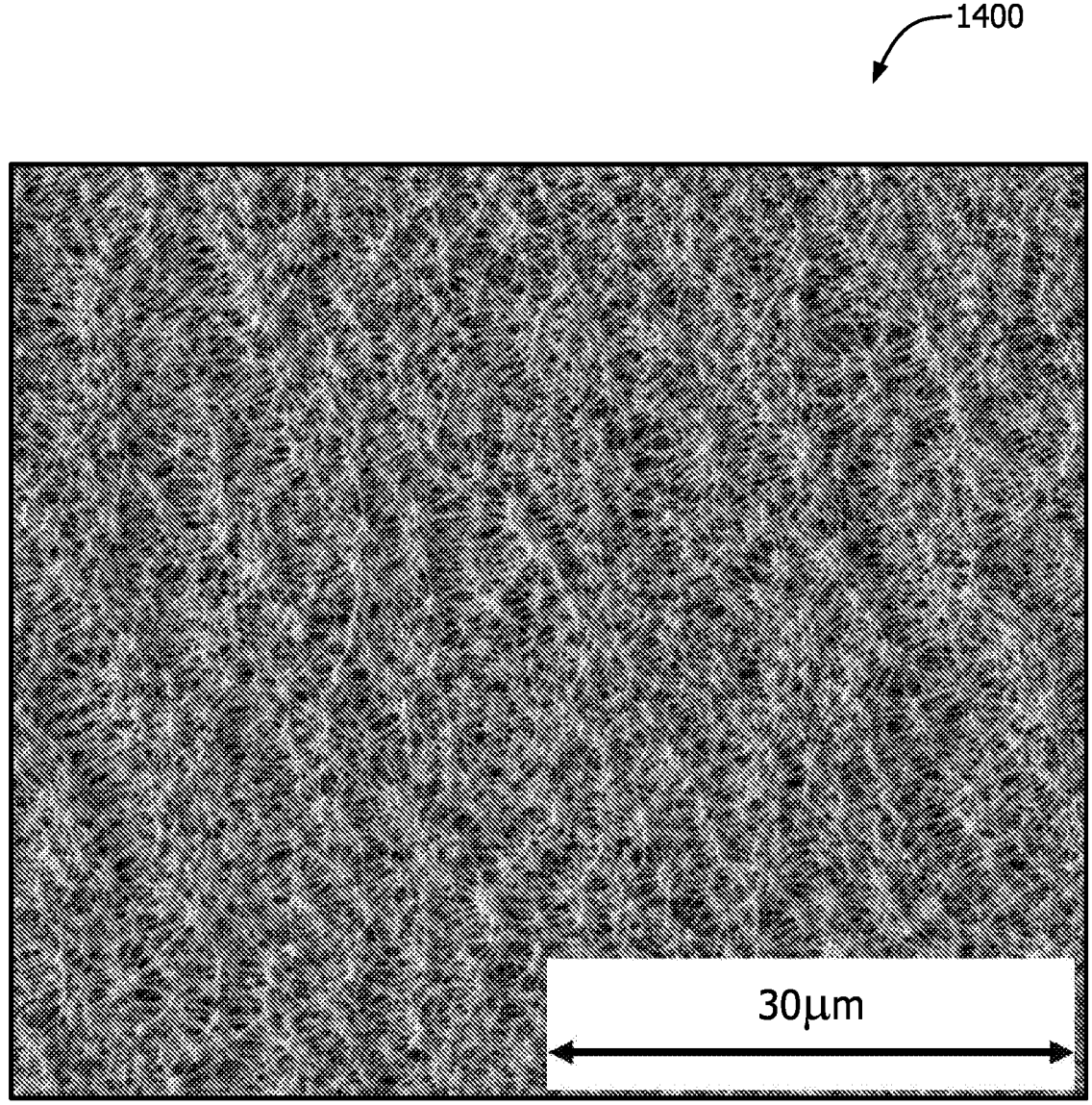
FIG. 14 is an SEM image of the top surface of a comparable cell impermeable layer formed of an expanded polytetrafluoroethylene (ePTFE) membrane in accordance with embodiments described herein.

A device was constructed using only a single membrane layer (i.e., not a composite) to provide baseline performance in absence of an open-tight biocompatible membrane composite. The single membrane served as the Cell Impermeable Layer only and was a commercially available microporous, hydrophilic ePTFE membrane with an MPS of 0.4 microns sold under the trade name Biopore® from Millipore (Cork, Ireland). This single layer provided a tight, cell impermeable interface while still enabling mass transport of oxygen and nutrients therethrough. A representative scanning electron micrograph (SEM) of a surface of the ePTFE membrane forming the cell impermeable layer is shown in FIG. 14.

This single membrane layer was evaluated and characterized for the relevant parameters. Parameters for layers are marked as "N/A" if they are not relevant for that layer's specific function. Parameters for layers are marked as "—" if they are practically unobtainable as a result of how the layers of the composite were processed. The methods used for the characterization of the relevant parameters were performed in accordance with the methods set forth in the section entitled "Method" set forth above. The results of Comparable Example 1 are summarized in Table 2.

TABLE 2

| Layer Function | Cell Impermeable | FBGC Mitigation |
|---|---|---|
| Description | Biopore ePTFE | None |
| MPS (μm) | 0.43 | none |
| Pore Size (μm) | 0.43 | none |
| Thickness (μm) | 25.7 | none |
| Mass (g/m²) | 20.6 | none |
| Porosity (%) | 63.6 | none |
| Solid Feature Spacing (μm) | N/A | none |
| Solid Feature Minor Axis (μm) | N/A | none |
| Solid Feature Major Axis (μm) | N/A | none |
| Solid Feature Depth (μm) | N/A | none |

TABLE 2-continued

| Layer Function | Cell Impermeable | FBGC Mitigation |
|---|---|---|
| Weakest Axis Tensile Strength (N/m) | 404.2 | none |
| Geometric Mean Tensile Strength (MPa) | 37.0 | none |
| Composite Bond (kPa) | N/A | |

Evaluation of Single ePTFE Membrane Performance

The single membrane layer was ultrasonically welded into a device form in accordance with the Integration of Biocompatible Membrane Composite into a Device Form set forth in the Test Methods section above and evaluated in vivo.

Figure 37:
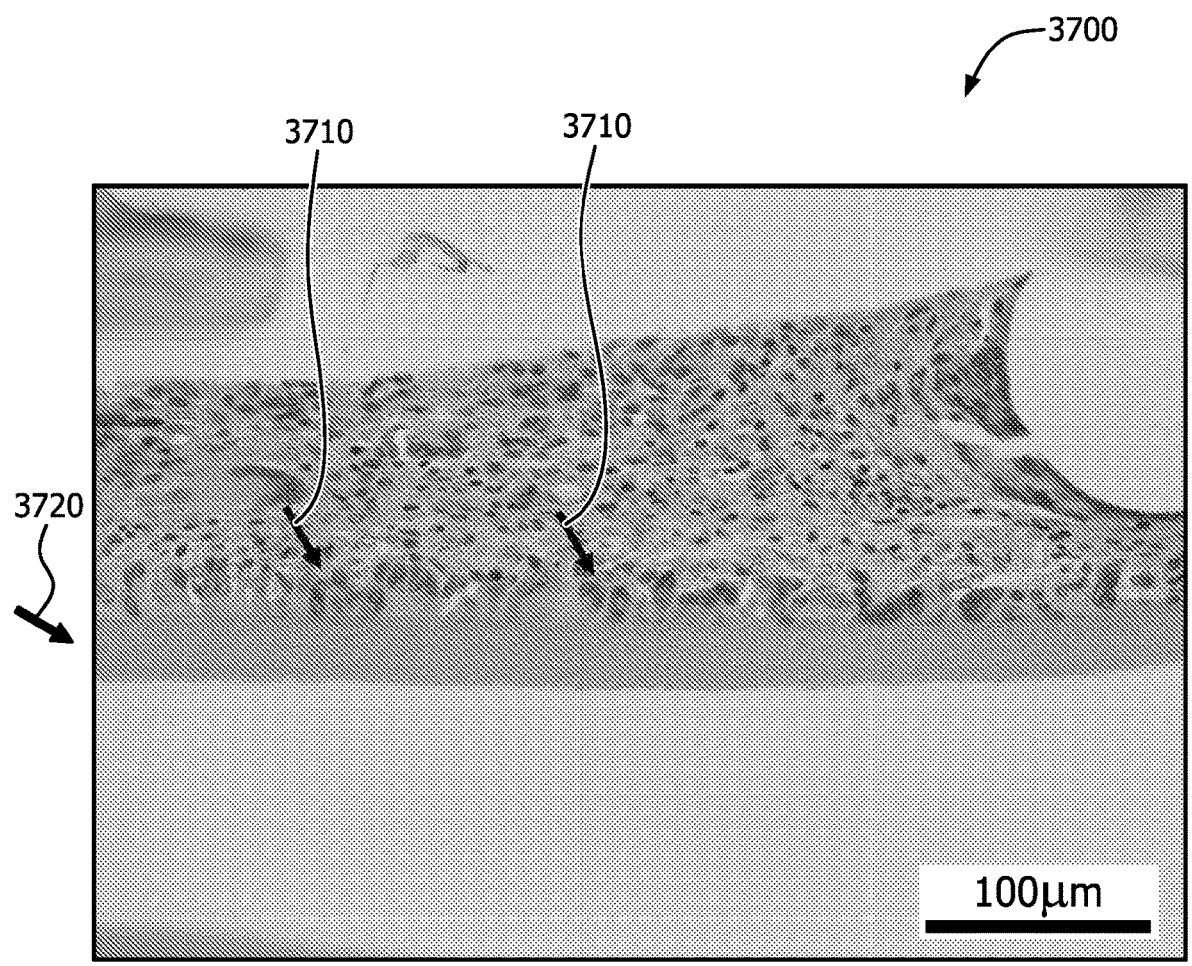
FIG. 37 is a representative histology image showing the observation of foreign body giant cells on the cell impermeable layer of Comparative Example 1 in accordance with embodiments described herein.

The host tissue response was evaluated in accordance with the In Vivo Porcine Study_set forth in the Test Methods section above. The host tissue response at the device interface demonstrated host tissue penetration up to the cell impermeable ePTFE tight layer. At this interface a contiguous line of foreign body giant cells was observed at the ePTFE layer, creating a barrier for neovascularization. The histology image shown in FIG. 37 is a representative image of the observation of foreign body giant cells indicated by arrows 3710 on the cell impermeable layer 3720.

The functional response was evaluated in vivo in accordance with the In Vivo Nude Rat Study set forth in the Test Methods section above. The results are shown in Table 3. The low levels of c-peptide indicate a low level of insulin producing cells present in the device.

TABLE 3

| | Mean Human c-peptide serum levels for each time point | | | | | | | | Sample size (n) for each time point | |
|---|---|---|---|---|---|---|---|---|---|---|
| | 12 weeks | | 16 weeks | | 20 weeks | | 23-24 weeks | | | |
| GSIS Time (min) | 0 | 90 | 0 | 90 | 0 | 90 | 0 | 90 | # animals | # devices |
| Comparative Example 1 * | 45.7 | 80 | nd | nd | nd | nd | nd | nd | 7 | 14 |
| Comparative Example 2 | 12** | 48 | 30 | 98 | 29 | 154 | 62 | 124 | 5 | 10 |
| Comparative Example 3 | 40 | 34 | 13 | 25 | nd | nd | nd | nd | 6 | 12 |
| Example 1 | 30 | 394 | 51.2 | 661 | 93 | 658 | 113 | 959 | 5-6 | 10-12 |

* 10 μl load or 3.7E6 cells per each device

** rats were not fasted prior to GSIS assay

Comparative Example 2

Manufacturing of Biocompatible Membrane Composite

A composite was constructed having two distinct layers. The first layer (Cell Impermeable Layer) was a commercially available microporous, hydrophilic ePTFE membrane with an MPS of 0.4 µm sold under the trade name Biopore® from Millipore (Cork, Ireland). This first layer provided a tight, cell impermeable interface while still enabling mass transport of oxygen and nutrients therethrough. A representative scanning electron micrograph (SEM) of the surface of the ePTFE membrane forming the cell impermeable layer is shown in FIG. 14.

Figure 15:
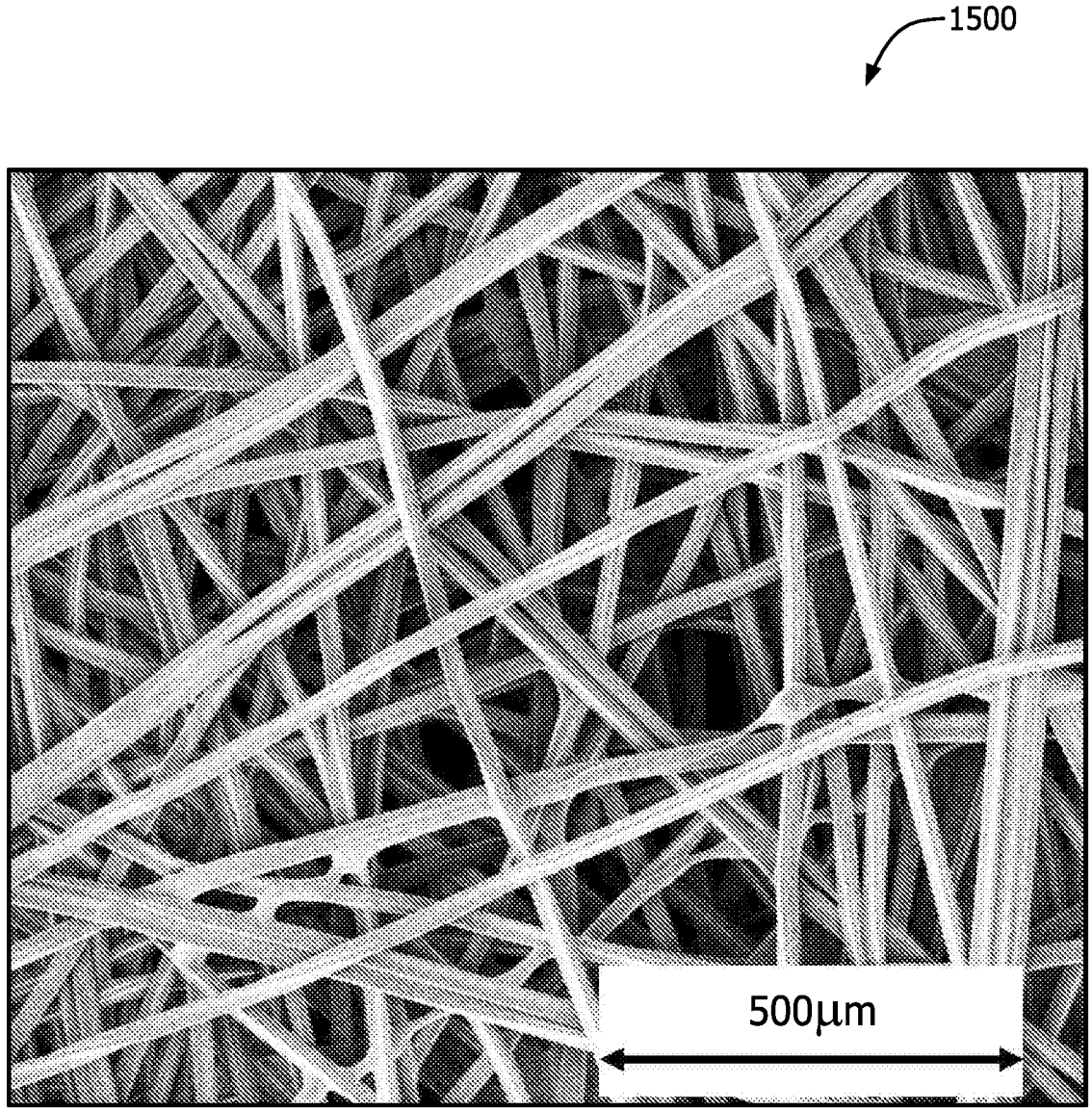
FIG. 15 is an SEM image of the top surface of a vascularization layer formed of a non-woven polyester in accordance with embodiments described herein.

The second layer (Mitigation Layer) was a commercially available spunbound polyester nonwoven material. A representative SEM of the surface of the nonwoven material forming the vascularization layer is shown in FIG. 15.

The two layers (Cell Impermeable and Mitigation Layers) were assembled into a composite using a heated lamination process. The fibers of the nonwoven material were heated to a temperature above their melt temperature so that they adhered to the ePTFE membrane across the entire surface area of the ePTFE membrane where the fibers of the spunbound nonwoven made contact with the surface of the ePTFE membrane. A 1.60 m Galaxy Flatbed Laminator was used and the ePTFE and the nonwoven material were processed at a temperature of 167.2° C. to 169.4° C., an applied Nip pressure of 344.7 kpa, and a speed of 1.22 meters per minute. Additionally, it was demonstrated that similar results were achieved with a 1.88 m HPL 74HC Flatbed Laminator where the ePTFE and the nonwoven material were processed at temperature of 156.1° C.-158.3° C., an applied Nip pressure of 34.5 kPa, and a speed of 2.44 meters per minute.

Characterization of the Biocompatible Membrane Composite

Each layer of the two-layer composite was evaluated and characterized for the relevant parameters necessary for the function of each layer. Parameters for layers are marked as "N/A" if they are not relevant for that layer's specific function. Parameters for layers are marked as "—" if they are practically unobtainable as a result of how the layers of the composite were processed. The methods used for the characterization of the relevant parameters were performed in accordance with the methods described in "Test Methods" section set forth above. The results of Comparable Example 2 are summarized in Table 4.

TABLE 4

| Layer Function | Cell Impermeable | FBGC Mitigation |
|---|---|---|
| Description | Biopore ePTFE | PET Nonwoven |
| MPS (µm) | 0.43 | N/A |
| Pore Size (µm) | 0.43 | 101.77 |
| Thickness (µm) | 25.7 | 77.4 |
| Mass (g/m$^2$) | 20.6 | 12.4 |
| Porosity (%) | 63.6 | 92.7 |
| Solid Feature Spacing (µm) | N/A | 77.9 |
| Solid Feature Minor Axis (µm) | N/A | 28.8 |
| Solid Feature Major Axis (µm) | N/A | — |
| Solid Feature Depth (µm) | N/A | 27.0 |
| Weakest Axis Tensile Strength (N/m) | 404.2 | 270.4 |
| Geometric Mean Tensile Strength (MPa) | 37.0 | 6.3 |
| Composite Bond (kPa) | — | |

Evaluation of the Composite Membrane Performance

The biocompatible membrane composite was ultrasonically welded into a device form in accordance with the Integration of Biocompatible Membrane Composite into a Device Form set forth in the Test Methods section above and evaluated in vivo.

Figure 16:
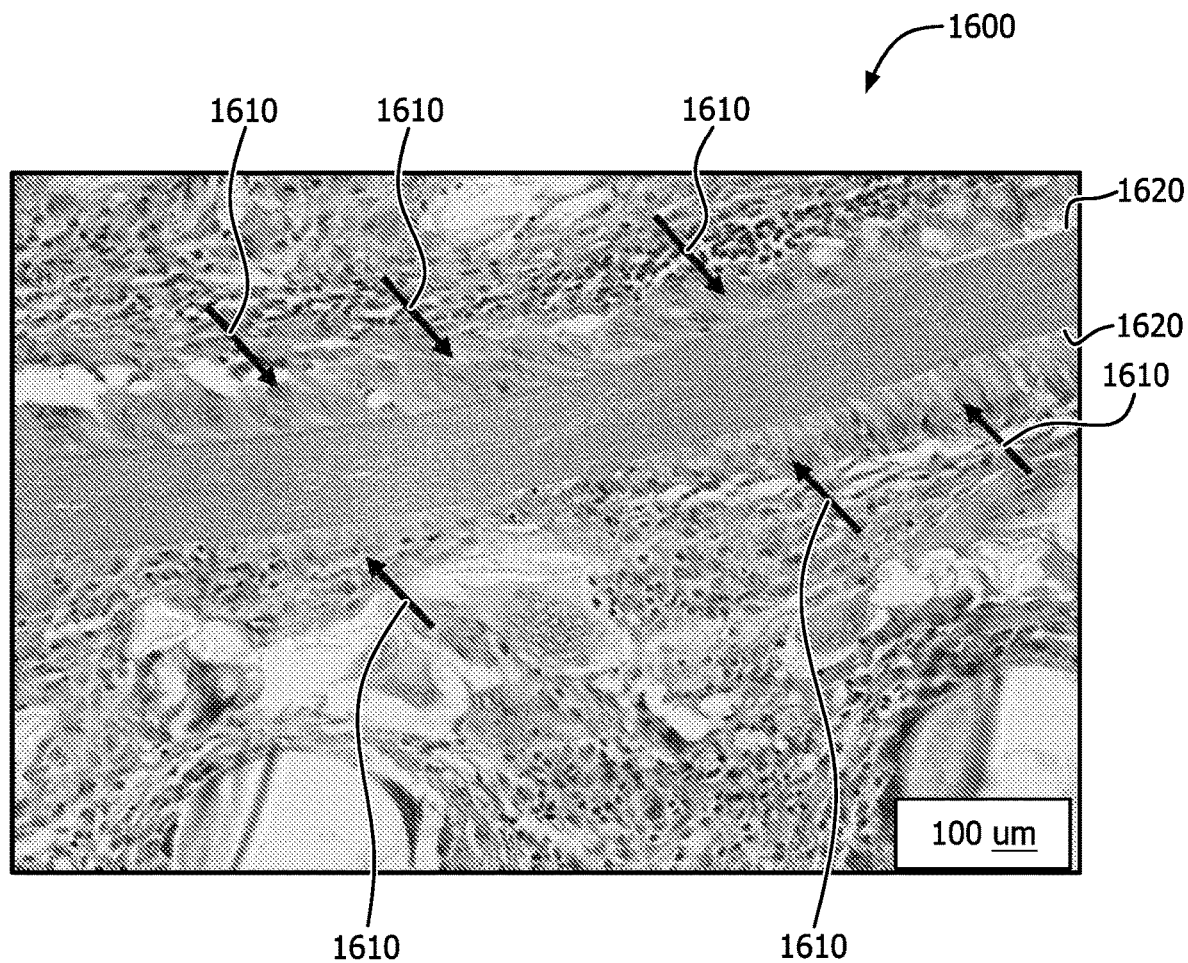
FIG. 16 is a representative histology image showing the presence of foreign body giant cells on the surface of a cell impermeable layer of Comparative Example 1 in accordance with embodiments described herein.

The host tissue response was evaluated in accordance with the In Vivo Porcine Study set forth in the Test Methods section set forth above. The host tissue response at the device interface demonstrated host tissue penetration through all layers of the device up to the cell impermeable ePTFE tight layer. At this interface a contiguous line of foreign body giant cells was observed at the ePTFE layer, creating a barrier for neovascularization. The histology image shown in FIG. 16 is a representative image of the observation of foreign body giant cells indicated by arrows 1610 on the cell impermeable layer 1620.

The functional response was evaluated in vivo in accordance with the In Vivo Nude Rat Study set forth in the Test Methods section above. The results are shown in Table 3. The low levels of c-peptide indicate a low level of insulin producing cells present in the device.

Comparative Example 3

Manufacturing of Biocompatible Membrane Composite

A composite was constructed with two distinct layers. A first layer of an ePTFE membrane (Cell Impermeable Layer) was formed according to the teachings of U.S. Pat. No. 3,953,566 to Gore.

Figure 17:
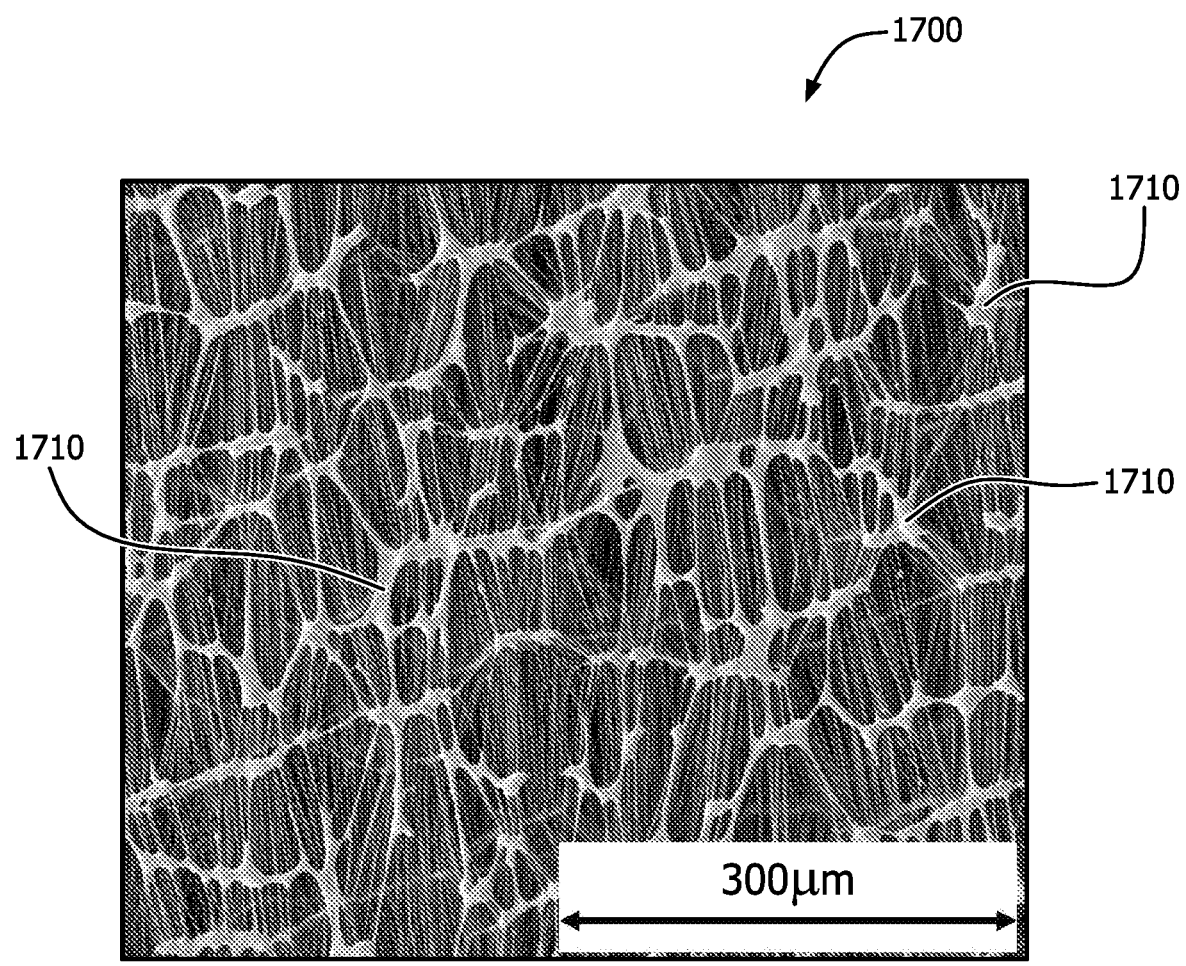
FIG. 17 is an SEM image of the top surface of the mitigation layer with a discontinuous layer of fluorinated ethylene propylene (FEP) on the mitigation layer of Comparative Example 2 in accordance with embodiments described herein.

A second ePTFE membrane (Mitigation Layer) was prepared according the teachings of U.S. Pat. No. 5,814,405 to Branca, et. al. During an initial machine direction (MD) expansion step, a fluorinated ethylene propylene (FEP) film was applied to the second ePTFE membrane. Through subsequent co-processing of the second ePTFE membrane and FEP through the machine direction (MD) expansion and transverse direction (TD) expansion, the FEP became discontinuous on the surface of the second ePTFE membrane as per the teachings of WO/94/13469 to Bacino. FIG. 17 is a representative image of the second ePTFE layer 1700 surface with discontinuous layer of FEP 1710 thereon.

Figure 18:
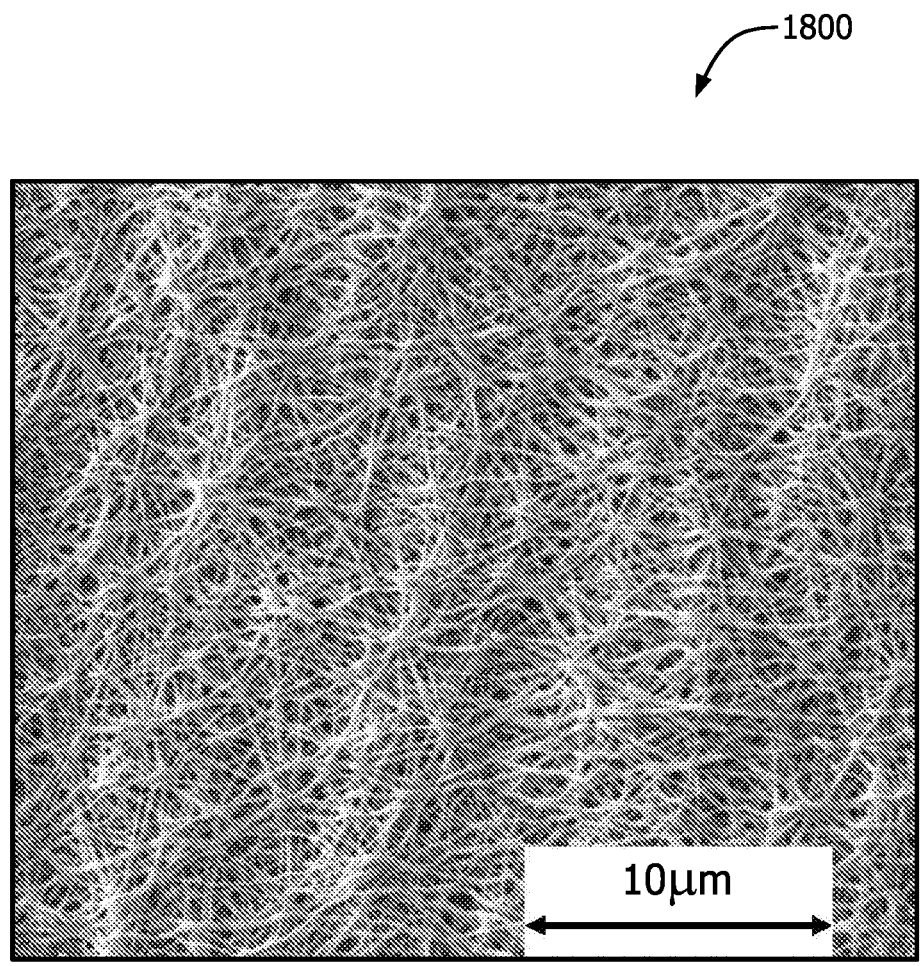
FIG. 18 is an SEM image of the top surface of the ePTFE cell impermeable layer of Comparative Example 3, Example 1, and Example 2 in accordance with embodiments described herein.
Figure 19:
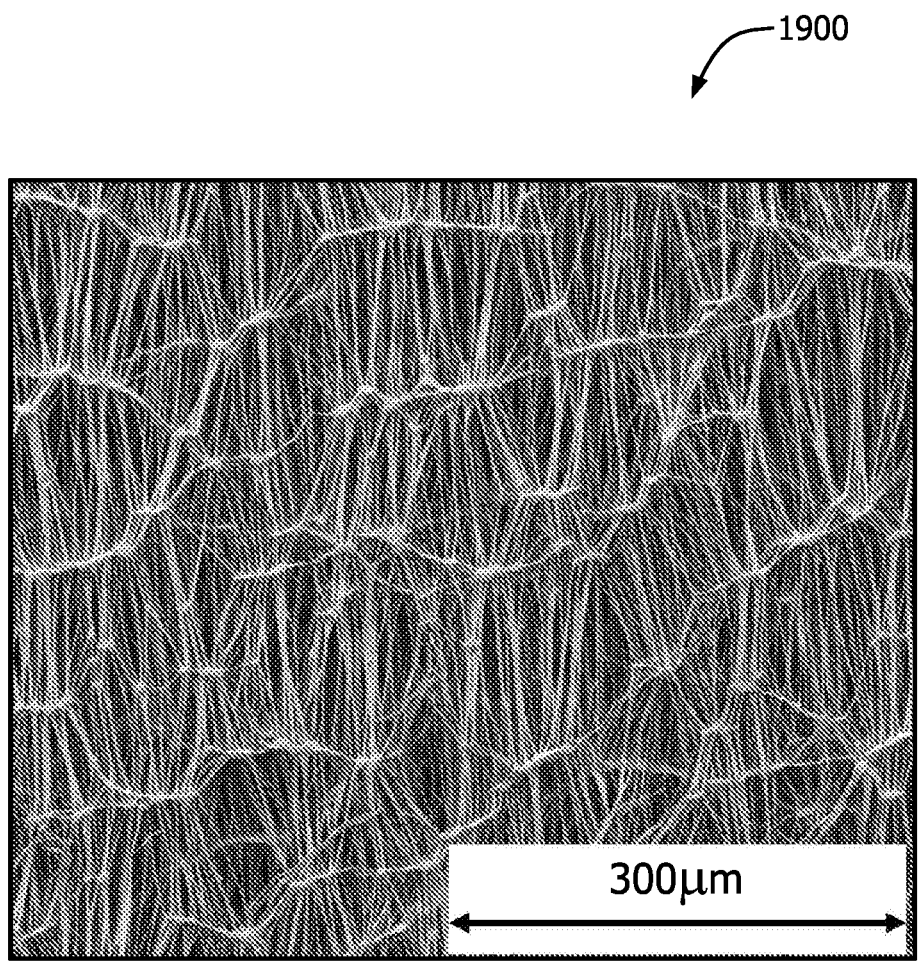
FIG. 19 is an SEM image of the top surface of the ePTFE mitigation layer of Comparative Example 3 in accordance with embodiments described herein.
Figure 20:
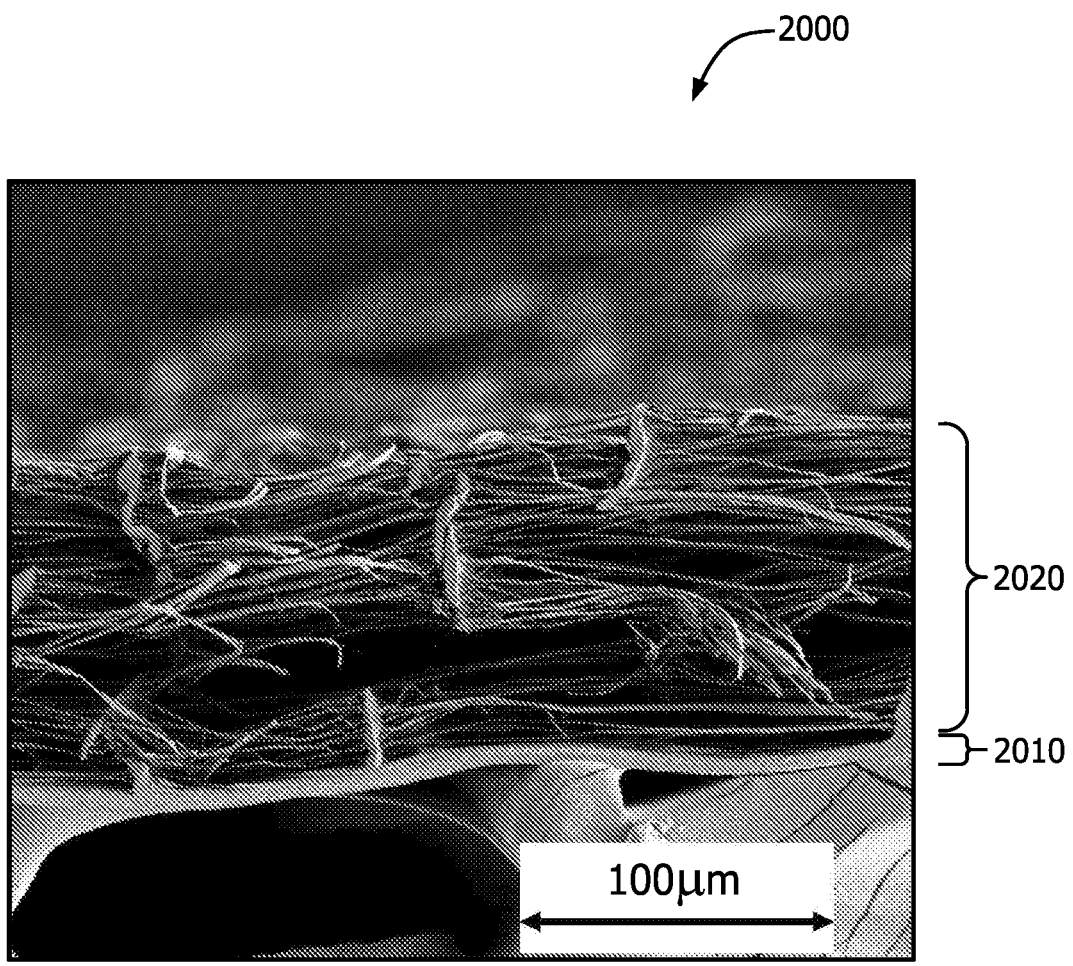
FIG. 20 is an SEM image of the cross-section of the two layer ePTFE composite of Comparative Example 3 in accordance with embodiments described herein.

The second ePTFE layer including the discontinuous FEP thereon was laminated to the first layer by bringing the materials (with the FEP positioned between the two layers) into contact at a temperature above the melting point of the FEP. Both ePTFE layers were held under tension to prevent unintentional deformation during this lamination process. The composite was subsequently rendered hydrophilic per the teachings in U.S. Pat. No. 5,902,745. The SEM image shown in FIG. 18 is a representative image of the node and fibril structure of the first ePTFE layer (Cell Impermeable Layer). The SEM image shown in FIG. 19 is a representative image of the node and fibril structure of the second ePTFE layer (Mitigation Layer). FIG. 20 is an SEM image of a representative image of the cross-section structure of the two-layer biocompatible membrane composite 2000 including the first ePTFE layer 2010 (Cell Impermeable Layer) and the second ePTFE layer 2020 (Mitigation Layer).

Characterization of the Biocompatible Membrane Composite

Each layer of the two-layer composite was evaluated and characterized for the relevant parameters necessary for the function of each layer. Parameters for layers are marked as "N/A" if they are not relevant for that layer's specific function. Parameters for layers are marked as "—" if they are practically unobtainable as a result of how the layers of the composite were processed. The methods used for the characterization of the relevant parameters were performed in accordance with the methods described in "Test Methods" section set forth above. The results of Comparable Example 3 are summarized in Table 5.

TABLE 5

| Layer Function | Cell Impermeable | FBGC Mitigation |
|---|---|---|
| Description | ePTFE Tight Layer | ePTFE Open Layer |
| MPS (μm) | 0.20 | — |
| Pore Size (μm) | 0.38 | 9.74 |
| Thickness (μm) | 8.4 | 95.7 |
| Mass (g/m²) | 4.2 | 6.6 |
| Porosity (%) | 77.4 | 96.9 |
| Solid Feature Spacing (μm) | N/A | 63.2 |
| Solid Feature Minor Axis (μm) | N/A | 4.2 |
| Solid Feature Major Axis (μm) | N/A | 24.6 |
| Solid Feature Depth (μm) | N/A | 24.5 |
| Weakest Axis Tensile Strength (MPa) | 799.3 | |
| Geometric Mean Tensile Strength (MPa) | 12.6 | |
| Composite Bond (kPa) | 251.4 | |

Evaluation of the Composite Membrane Performance

The biocompatible membrane composite was thermally welded into a device form in accordance with the Integration of Biocompatible Membrane Composite into a Device Form set forth in the Test Methods section above and evaluated in vivo.

Figure 21:
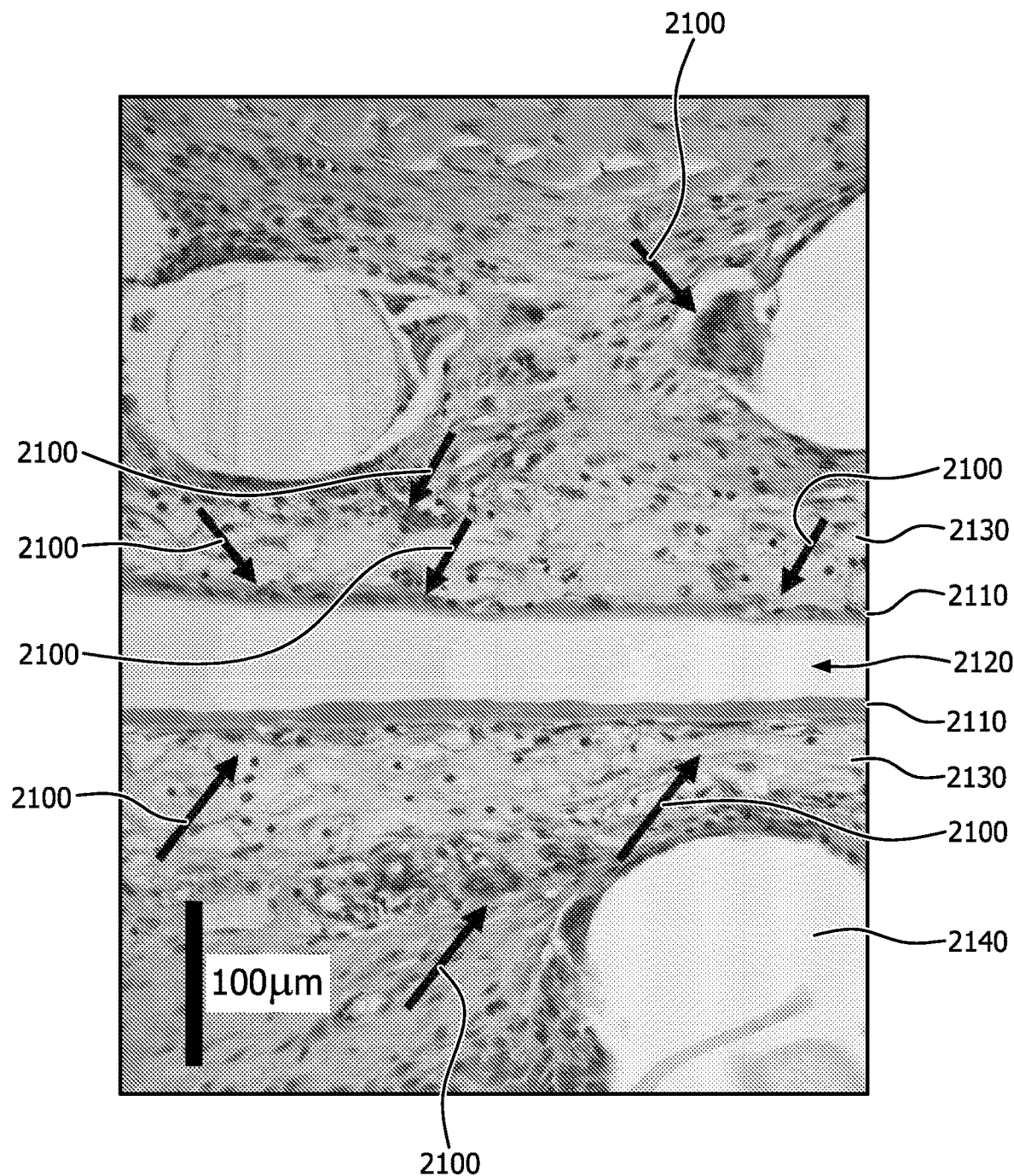
FIG. 21 is a representative histology image showing foreign body giant cells abutting the cell impermeable layers of Comparative Example 3 in accordance with embodiments described herein.

The host tissue response was evaluated in accordance with the In Vivo Porcine Study set forth in the Test Methods section above. The host tissue response at the device interface demonstrated host tissue penetration through all layers of the device up to the cell impermeable ePTFE tight layer. At this interface a contiguous line of foreign body giant cells was still visible at the cell impermeable layer, creating a barrier for neovascularization as seen in Comparable Examples 1 and 2. FIG. 21 is a representative histology image of the observation of foreign body giant cells (indicated by reference numerals 2100) abutting cell impermeable layers 2110. The lumen 2120, the mitigation layer 2130, and an external reinforcing component 2140 are also depicted in FIG. 21.

The functional response was evaluated in vivo in accordance with the In Vivo Nude Rat Study set forth in the Test Methods section above. The results are shown in Table 3. The functional response of the device loaded with cells is shown in Table 3. The low levels of c-peptide indicate a low level of insulin producing cells present in the device.

Example 1

Manufacturing of Biocompatible Membrane Composite

A composite was constructed with two distinct layers. A first ePTFE membrane (Cell Impermeable Layer) was formed according to the teachings of U.S. Pat. No. 3,953,566 to Gore.

Figure 22:
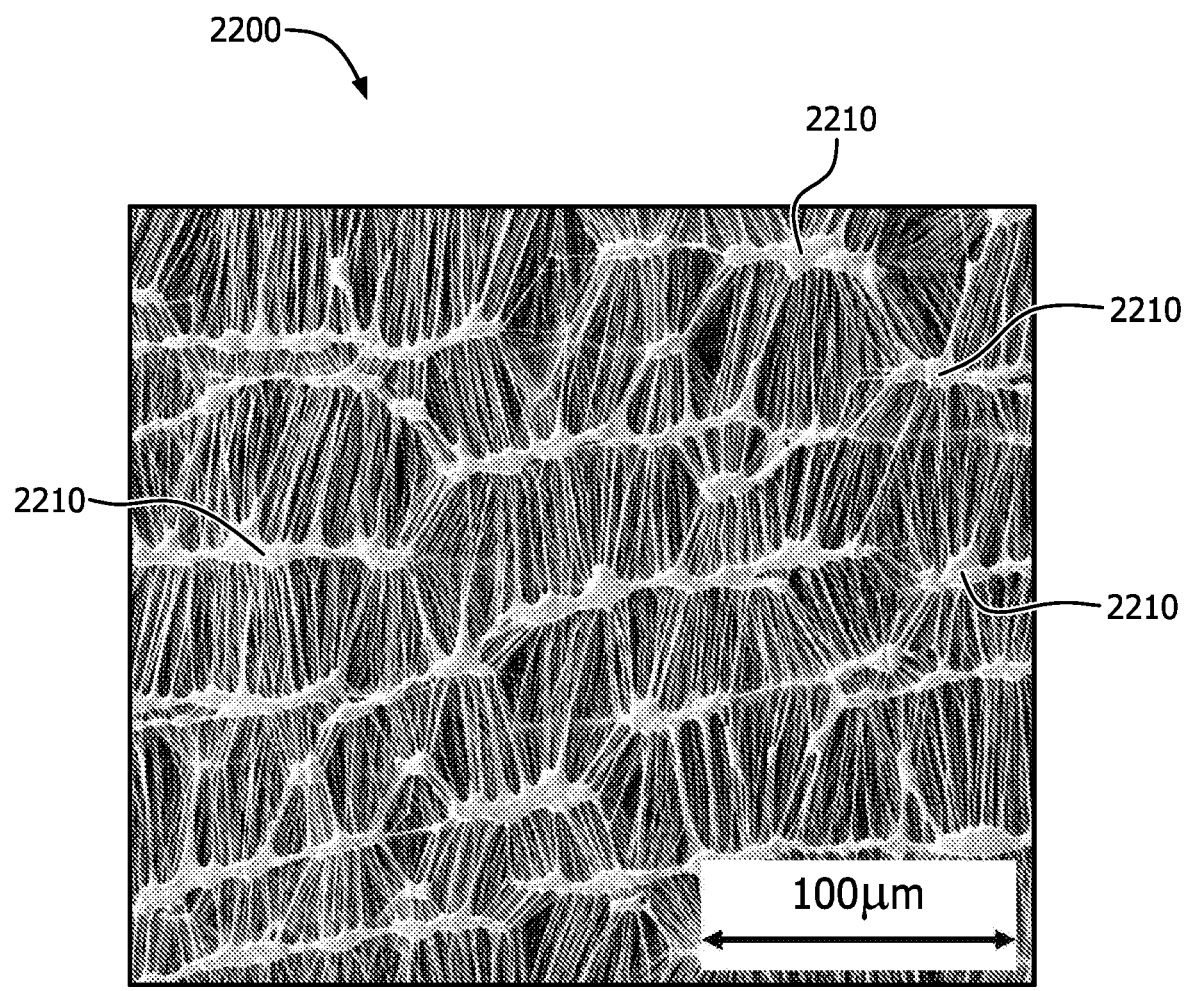
FIG. 22 is an SEM image of the top surface of the ePTFE mitigation layer with a discontinuous layer of fluorinated ethylene propylene (FEP) thereon of Example 1 in accordance with embodiments described herein.

A second ePTFE membrane (Mitigation Layer) was prepared according to the teachings of U.S. Pat. No. 5,814,405 to Branca, et al. During the initial machine direction (MD) expansion step, a fluorinated ethylene propylene (FEP) film was applied to the second ePTFE membrane. Through subsequent co-processing of the second ePTFE membrane and FEP through machine direction (MD) expansion and transverse direction (TD) expansion, the FEP became discontinuous on the second ePTFE membrane as per the teachings of WO/94/13469 to Bacino. The SEM image shown in FIG. 22 is a representative image of the second ePTFE membrane surface 2200 with the discontinuous layer of FEP 2210 thereon.

Figure 23:
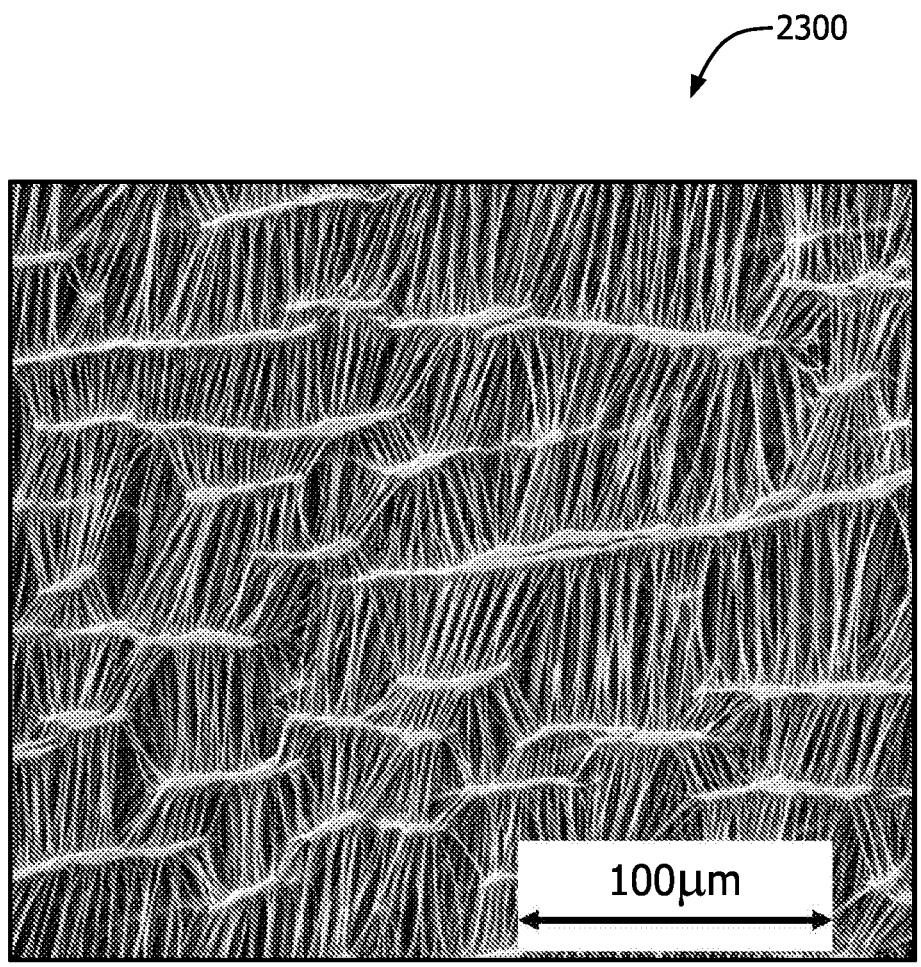
FIG. 23 is an SEM image of the top surface of the ePTFE mitigation layer of Example 1 in accordance with embodiments described herein.
Figure 24:
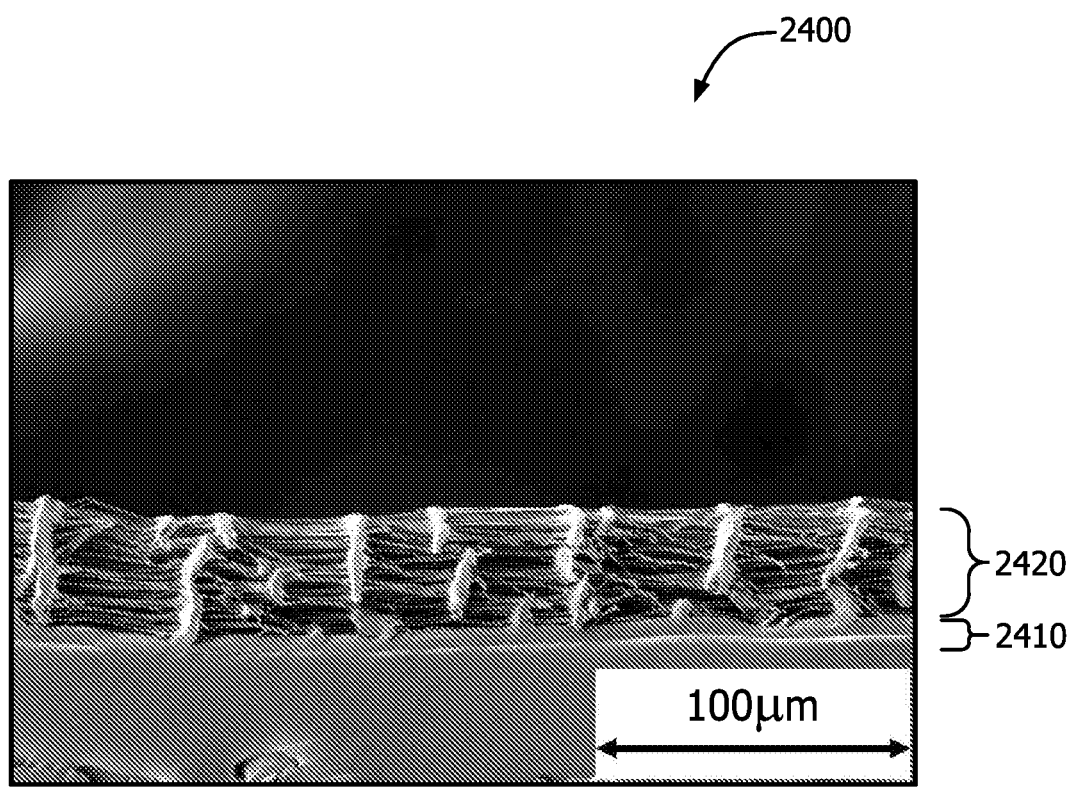
FIG. 24 is an SEM image of the cross-section of the two-layer ePTFE composite of Example 1 in accordance with embodiments described herein.

The second ePTFE layer including the discontinuous layer of FEP thereon was laminated to the first ePTFE layer by bringing the materials (with the FEP positioned between the two ePTFE membranes) into contact at a temperature above the melting point of the FEP. The two ePTFE layers were left unrestrained in the transverse direction during lamination. The laminate was then transversely expanded above the melting point of polytetrafluoroethylene (PTFE) such that each ePTFE layer was returned to its width prior to any necking sustained through lamination. The composite was subsequently rendered hydrophilic per the teachings of U.S. Pat. No. 5,902,745, to Butler, et al. The SEM image shown in FIG. 18 is a representative image of the node and fibril structure of the first ePTFE membrane (Cell Impermeable Layer). The SEM image shown in FIG. 23 is a representative image of the node and fibril structure of the second ePTFE membrane (Mitigation Layer). The SEM image shown in FIG. 24 is a representative image of the cross-section structure of the two-layer composite 2400 (i.e., the first ePTFE membrane 2410 (Cell Impermeable Layer) and the second ePTFE membrane 2420 (Mitigation Layer)).

Characterization of the Biocompatible Membrane Composite

Each layer of the two-layer composite was evaluated and characterized for the relevant parameters necessary for the function of each layer. Parameters for layers are marked as "N/A" if they are not relevant for that layer's specific function. Parameters for layers are marked as "—" if they are practically unobtainable as a result of how the layers of the composite were processed. The methods used for the characterization of the relevant parameters were performed in accordance with the methods described in "Test Methods" section set forth above. The results of Example 1 are summarized in Table 6.

TABLE 6

| Layer Function | Cell Impermeable | FBGC Mitigation |
|---|---|---|
| Description | ePTFE Tight Layer | ePTFE Open Layer |
| MPS (μm) | 0.18 | — |
| Pore Size (μm) | 0.34 | 8.06 |
| Thickness (μm) | 6.1 | 44.6 |
| Mass (g/m²) | 3.8 | 6.2 |
| Porosity (%) | 71.7 | 93.7 |
| Solid Feature Spacing (μm) | N/A | 24.2 |
| Solid Feature Minor Axis (μm) | N/A | 4.7 |
| Solid Feature Major Axis (μm) | N/A | 31.9 |
| Solid Feature Depth (μm) | N/A | 11.5 |
| Weakest Axis Tensile Strength (N/m) | 768.8 | |
| Geometric Mean Tensile Strength (MPa) | 22.8 | |
| Composite Bond (kPa) | 1231.9 | |

Evaluation of the Composite Membrane Performance

The biocompatible membrane composite was thermally welded into a device form in accordance with the Integration of Biocompatible Membrane Composite into a Device Form set forth in the Test Methods section above and evaluated in vivo.

Figure 38:
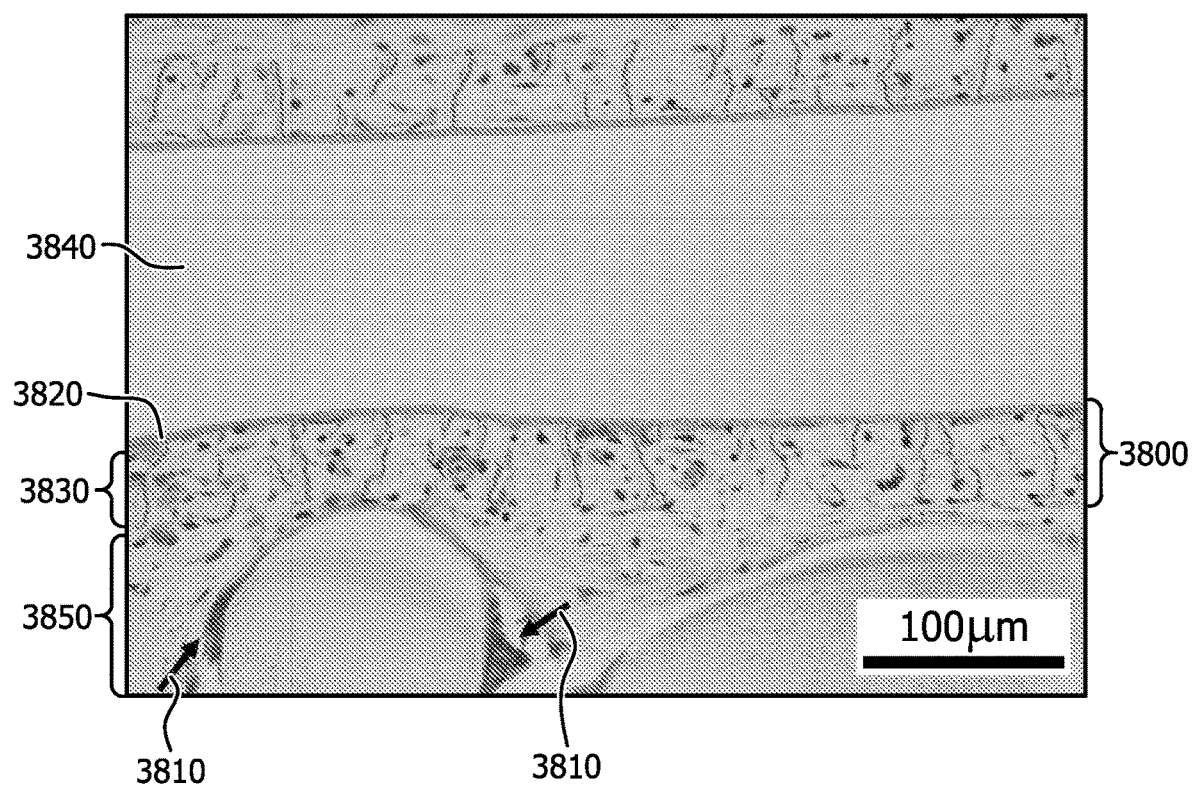
FIG. 38 is a representative histology image showing the absence of the formation of foreign body giant cell on the impermeable layer of Example 1 in accordance with embodiments described herein.

The host tissue response was evaluated in the In Vivo Porcine Study set forth in the Method section above. The host tissue response at the device interface demonstrated host tissue penetration through the polyester woven mesh reinforcing component and open ePTFE mitigation layer up to the tight ePTFE cell impermeable layer. While foreign body giant cells were present within the polyester woven mesh (reinforcing component), there was no evidence of foreign body giant cells observed lining the tight, ePTFE layer (Cell Impermeable Layer) in comparison to what was observed in Comparable Examples 1-3. The histology image shown in FIG. 38 is a representative image of this observation, with arrows 3810 indicating the location of the foreign body giant cells in relation to each layer and within the biocompatible membrane composite 3800. Additionally, as shown in FIG. 38, foreign body giant cells did not form a layer on the surface of the cell impermeable layer 3820. It was concluded that the biocompatible membrane composite 3800 formed of the cell impermeable layer 3820 and the mitigation layer 3830 described in this Example reduced the formation of foreign body giant cells on the surface of the cell impermeable layer 3820. The lumen 3840 and an external reinforcing component 3850 are also depicted in FIG. 38.

The functional response was evaluated in vivo in accordance with the In Vivo Nude Rat Study described in the Test Methods section set forth above. The results are shown in Table 3. The results demonstrated a step change in functional response as compared to the comparative examples, which indicated a significant increase in viability of insulin producing cells. At 12 weeks after implantation, the c-peptide blood serum concentration measured in response to glucose stimulated insulin secretion was, on average, 394 µM, which is 4.9 times that of Comparative Example 1 and 8.2 times that of Comparative Example 2 where no mitigation layer is present. It was concluded that in order to achieve such an increase in the degree of functional response, the mitigation layer was able to successfully mitigate the formation of foreign body giant cells at the cell impermeable interface.

Example 2

Manufacturing of Biocompatible Membrane Composite

A biocompatible membrane composite was constructed with two distinct layers. A first layer consisting of an ePTFE membrane (Cell Impermeable Layer) was formed according to the teachings of U.S. Pat. No. 3,953,566 to Gore.

Figure 25:
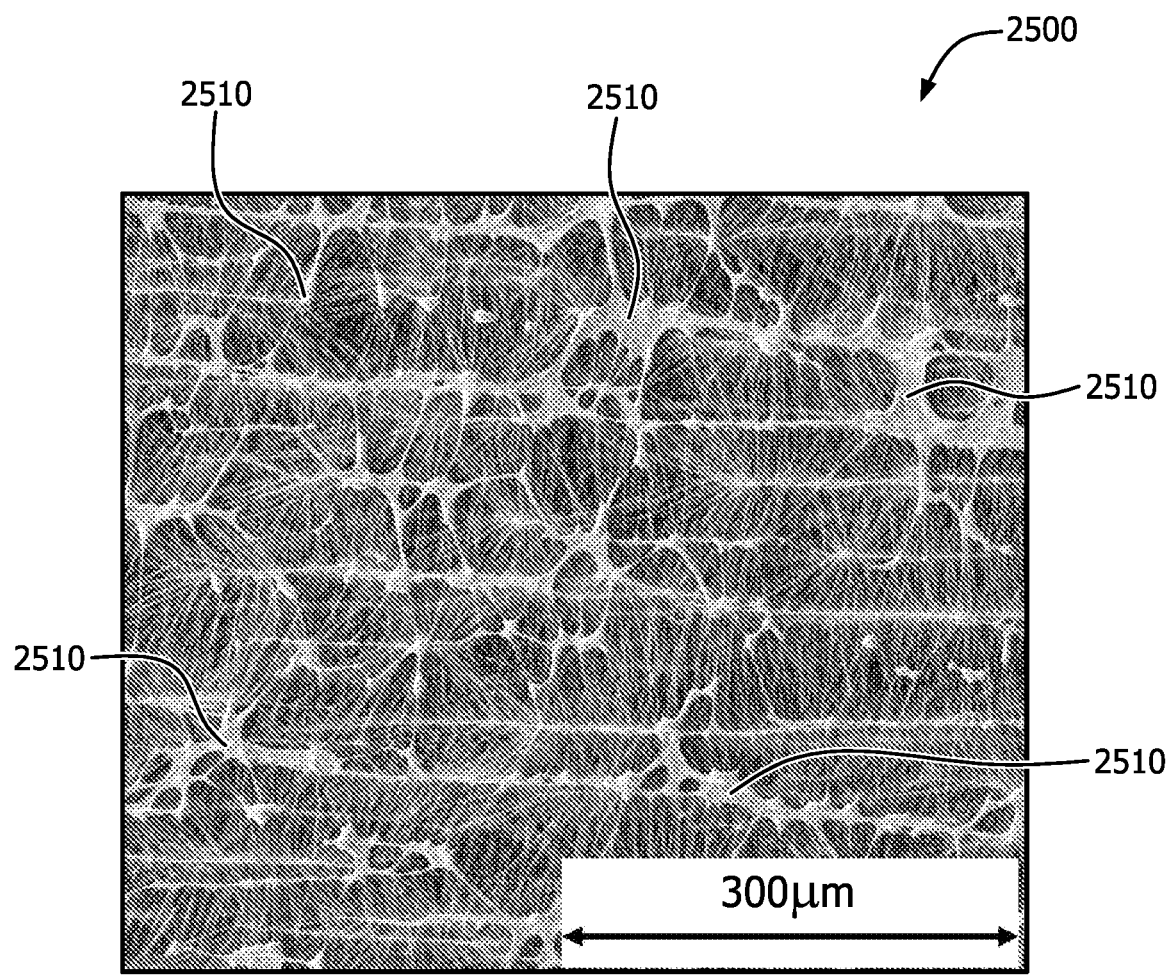
FIG. 25 is an SEM image of the top surface of the ePTFE mitigation layer with a discontinuous layer of FEP thereon of Example 2 in accordance with embodiments described herein.

A second ePTFE membrane (FBGC Mitigation Layer) was prepared according the teachings of U.S. Pat. No. 5,814,405 to Branca, et al. During the initial machine direction (MD) expansion step, a fluorinated ethylene propylene (FEP) film was applied to the second ePTFE membrane. Through subsequent co-processing of the second ePTFE membrane and FEP through machine direction (MD) expansion and transverse direction (TD) expansion, the FEP became discontinuous on the second ePTFE membrane as per the teachings of WO/94/13469 to Bacino. The SEM image shown in FIG. 25 is a representative image of the surface or the second ePTFE membrane 2500 having thereon discontinuous FEP 2510.

Figure 26:
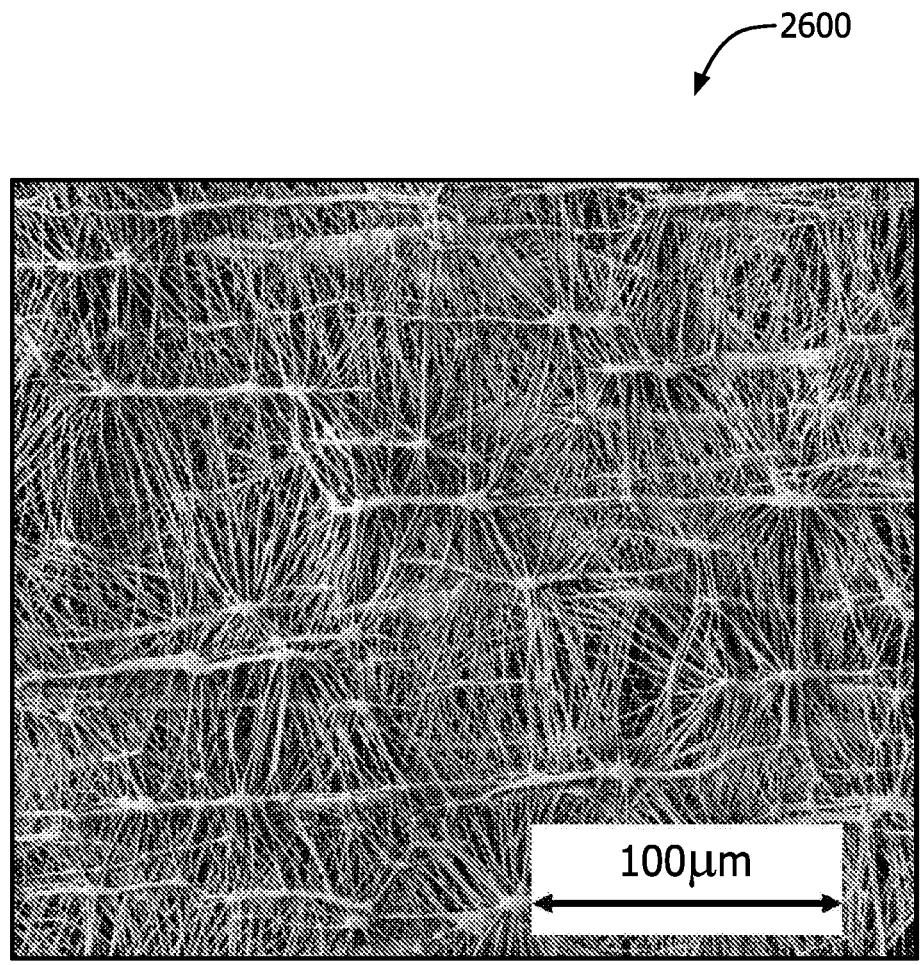
FIG. 26 is an SEM image of the top surface of the ePTFE mitigation layer of Example 2 in accordance with embodiments described herein.
Figure 27:
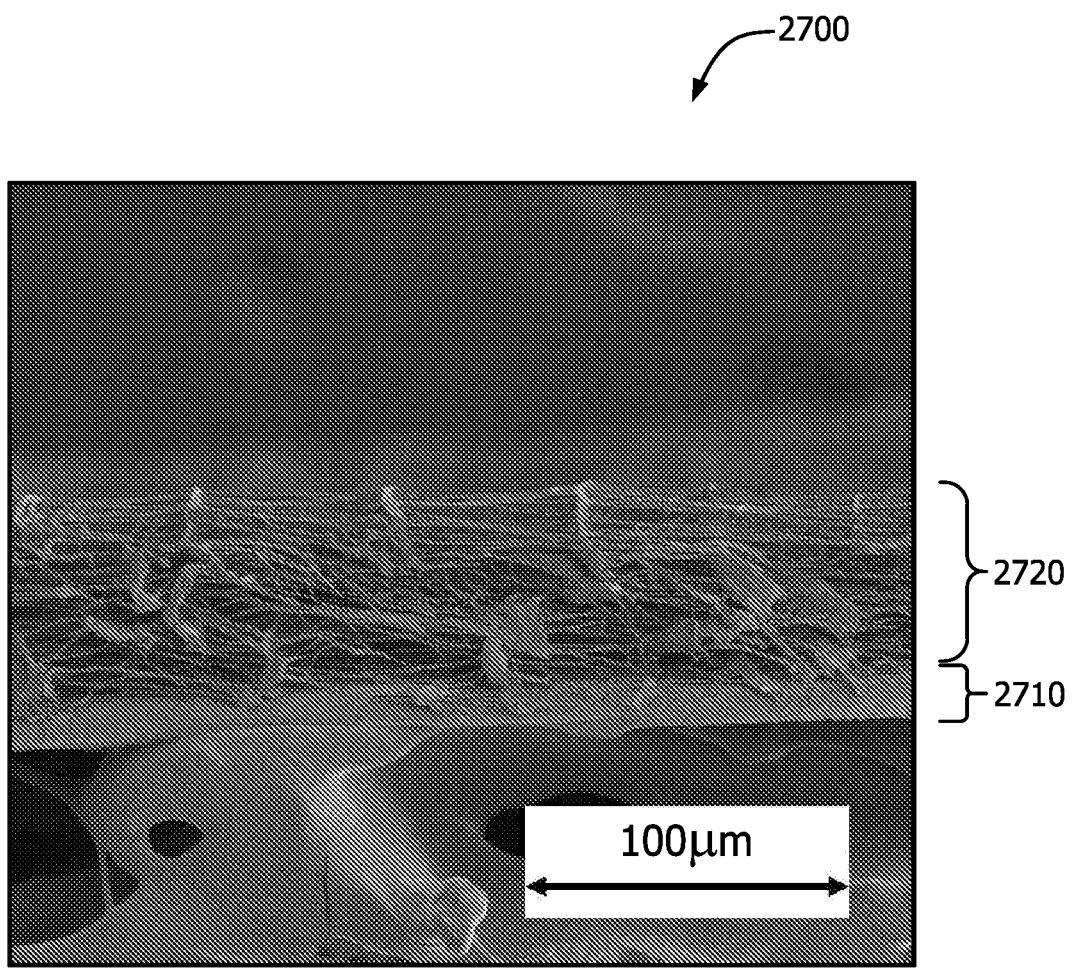
FIG. 27 is an SEM image of the cross-section of the two-layer ePTFE composite of Example 2 in accordance with embodiments described herein.

The second ePTFE layer that included the discontinuous FEP layer was laminated to the first ePTFE layer by bringing the two ePTFE membranes materials into contact (with the FEP positioned between the two ePTFE membranes) at a temperature above the melting point of the FEP. Both ePTFE layers were held under tension to prevent unintentional deformation during this lamination process. The laminate was subsequently rendered hydrophilic per the teachings of U.S. Pat. No. 5,902,745 to Butler, et al. The SEM image shown in FIG. 18 is a representative image of the node and fibril structure of the first ePTFE layer (Cell Impermeable Layer). The SEM image shown in FIG. 26 is a representative image of the node and fibril structure of the second ePTFE membrane (Mitigation Layer). The SEM image shown in FIG. 27 is a representative image of the cross-section structure of the two layer ePTFE laminate 2700 having the first ePTFE membrane 2710 (Cell Impermeable Membrane) and the second ePTFE membrane 2720 (Mitigation Layer).

Characterization of the Biocompatible Membrane Composite

Each layer of the two-layer composite was evaluated and characterized for the relevant parameters necessary for the function of each layer. Parameters for layers are marked as "N/A" if they are not relevant for that layer's specific function. Parameters for layers are marked as "—" if they are practically unobtainable as a result of how the layers of the composite were processed. The methods used for the characterization of the relevant parameters were performed in accordance with the methods described in "Test Methods" section set forth above. The results of Example 2 are summarized in Table 7.

TABLE 7

| Layer Function | Cell Impermeable | FBGC Mitigation |
|---|---|---|
| Description | ePTFE Tight Layer | ePTFE Open Layer |
| MPS (µm) | 0.18 | — |
| Porosity (%) | 78.3 | 96.6 |
| Pore Size (µm) | 0.38 | 2.40 |
| Thickness (µm) | 8.7 | 44.5 |
| Mass (g/m$^2$) | 4.1 | 3.3 |
| Porosity (%) | 78.3 | 96.6 |
| Solid Feature Spacing (µm) | N/A | 12.0 |
| Solid Feature Minor Axis (µm) | N/A | 3.2 |
| Solid Feature Major Axis (µm) | N/A | 32.9 |
| Solid Feature Depth (µm) | N/A | 12.5 |
| Weakest Direction Tensile Strength (N/m) | 867.9 | |
| Geometric Mean Tensile Strength (N/m) | 24.1 | |
| Composite Bond (kPa) | 288.6 | |

Evaluation of the Composite Membrane Performance

The biocompatible membrane composite was thermally welded into a device form in accordance with the Integration of Biocompatible Membrane Composite into a Device Form set forth in the Test Methods section above and evaluated in vivo.

Figure 28:
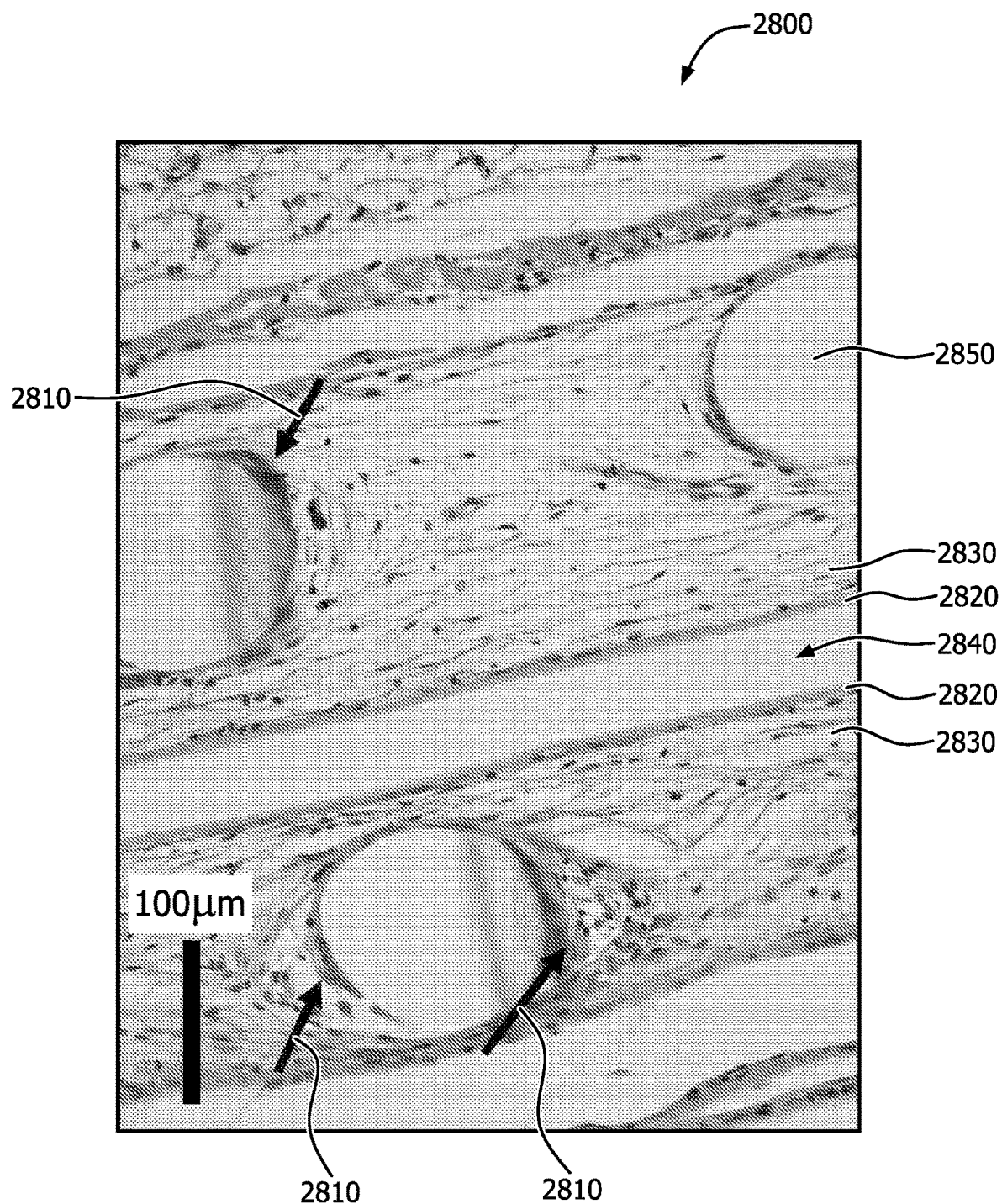
FIG. 28 is a representative histology image showing the absence of the formation of foreign body giant cells on the cell impermeable layer of Example 2 in accordance with embodiments described herein.

The device was evaluated in vivo for host tissue response in the In Vivo Porcine Study set forth in the Method section above The host tissue response at the device interface demonstrated host tissue penetration through the polyester woven mesh reinforcing component and open ePTFE mitigation layer up to the tight ePTFE cell impermeable layer. While foreign body giant cells were present within the polyester woven mesh (reinforcing component), there was no evidence of foreign body giant cells observed lining the tight, ePTFE layer (Cell Impermeable Layer) in comparison to what was observed in Comparable Examples 1-3. The histology image shown in FIG. 28 is a representative image of this observation, with arrows 2810 indicating the location of the foreign body giant cells in relation to each layer and within the biocompatible membrane composite 2800. Additionally, as shown in FIG. 28, foreign body giant cells did not form a layer on the surface of the cell impermeable layer 2820. It was concluded that the biocompatible membrane composite 2800 formed of the cell impermeable layer 2820 and the mitigation layer 2830 described in this Example reduced the formation of foreign body giant cells on the surface of the cell impermeable layer 2820. The lumen 2840 and an external reinforcing component 2850 are also depicted in FIG. 28. Additionally, even though the cell impermeable membrane had low thickness and mass, it was observed that the tensile strength was adequate to maintain the integrity of the lumen since no host cells were observed breaching the lumen.

Example 3

Manufacturing of Biocompatible Membrane Composite

Figure 29:
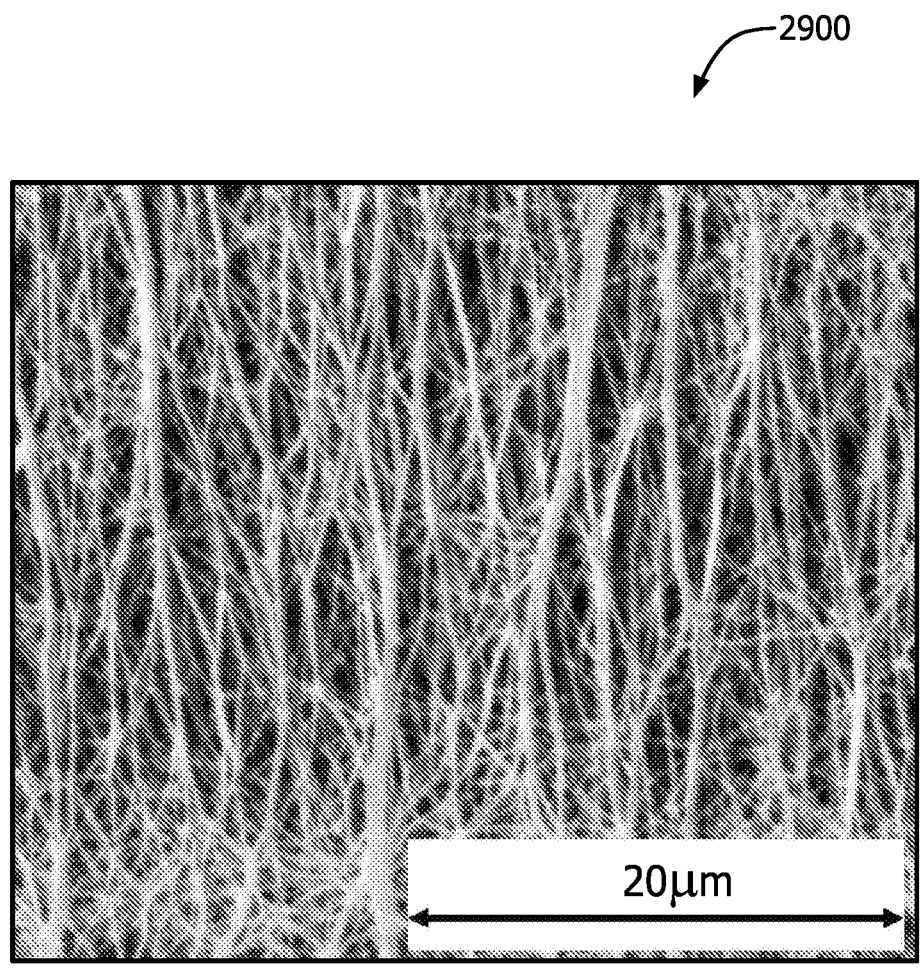
FIG. 29 is an SEM image of the top surface of the ePTFE cell impermeable layer of Example 3 in accordance with embodiments described herein.
Figure 30:
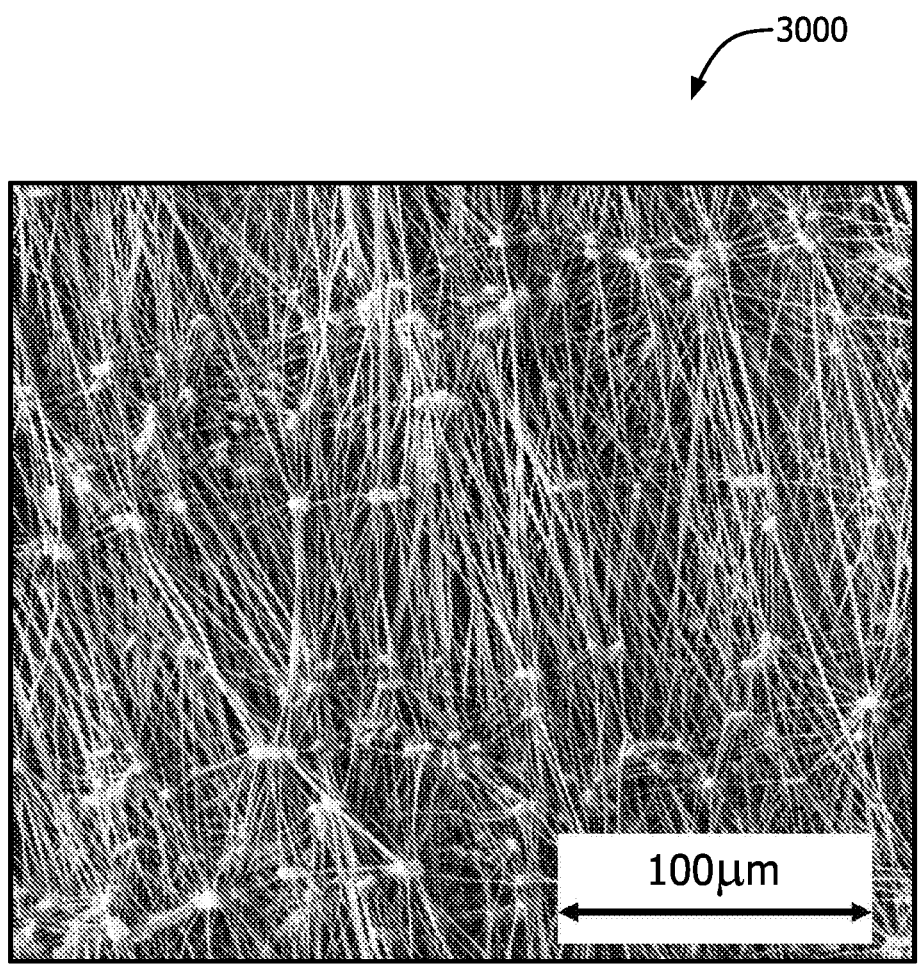
FIG. 30 is an SEM image of the top surface of the ePTFE mitigation layer of Example 3 in accordance with embodiments described herein.
Figure 31:
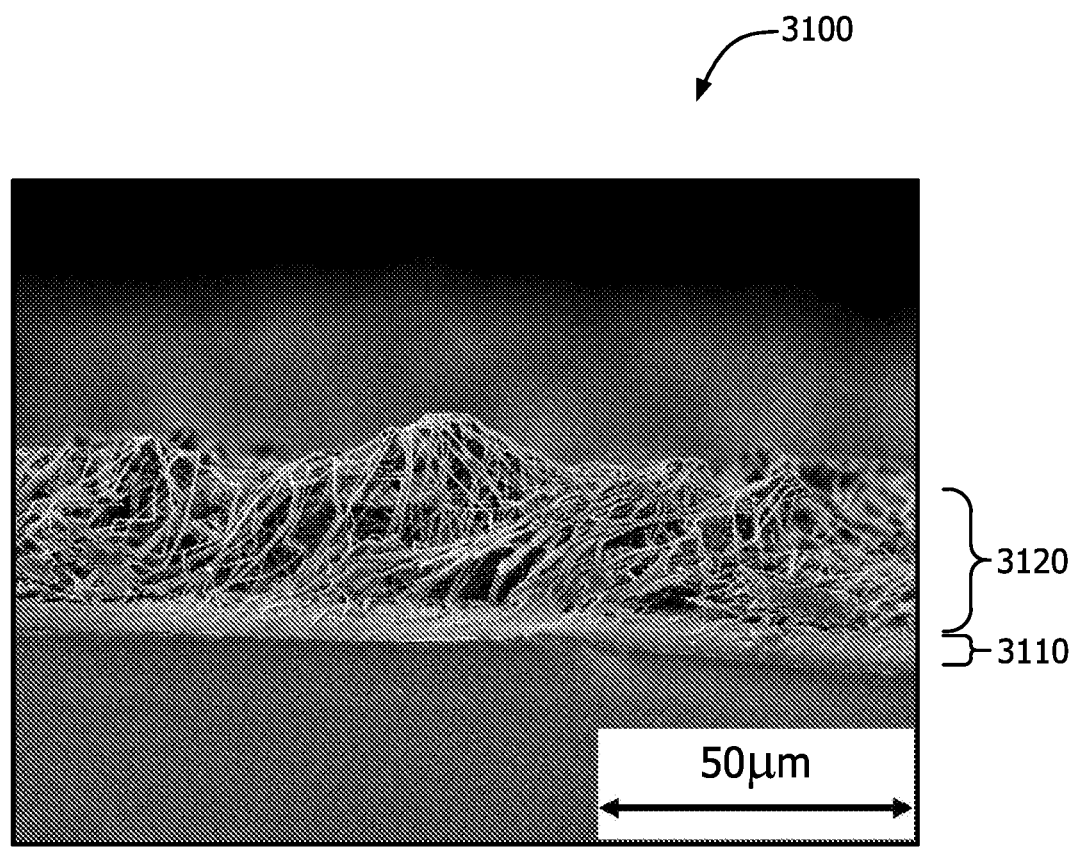
FIG. 31 is an SEM image of the cross-section of a two-layer ePTFE composite formed in Example 3 in accordance with embodiments described herein.

A biocompatible membrane composite having two distinct layers was constructed. First, a two-layer ePTFE composite was prepared by layering and then co-expanding a first ePTFE layer consisting of a dry, biaxially-expanded membrane (Cell Impermeable Layer) prepared according to the teachings of U.S. Pat. No. 3,953,566 to Gore and a second ePTFE layer consisting of a paste extruded calendered tape (Mitigation Layer) prepared according to the teachings of U.S. Pat. No. 3,953,566 to Gore. The two-layer ePTFE composite was biaxially expanded and then rendered hydrophilic according to the teachings of U.S. Pat. No. 5,902,745, to Butler, et al. A representative surface microstructure of the first layer is shown in the SEM image of FIG. 29. A representative surface microstructure of the second ePTFE membrane is shown in FIG. 30. A representative cross section showing the microstructure of the composite 3100 including the first ePTFE membrane 3110 (Cell Impermeable Layer) and the second ePTFE membrane 3120 (Mitigation Layer) is shown in the SEM image of FIG. 31.

Characterization of the Biocompatible Membrane Composite

Each layer of the two-layer composite was evaluated and characterized for the relevant parameters necessary for the function of each layer. Parameters for layers are marked as "N/A" if they are not relevant for that layer's specific function. Parameters for layers are marked as "—" if they are practically unobtainable as a result of how the layers of the composite were processed. The methods used for the characterization of the relevant parameters were performed in accordance with the methods described in "Test Methods" section set forth above. The results of Example 3 are summarized in Table 8.

TABLE 8

| Layer Function | Cell Impermeable | FBGC Mitigation |
|---|---|---|
| Description | ePTFE Tight Layer | ePTFE Open Layer |
| MPS (μm) | 0.35 | — |
| Pore Size (μm) | 0.51 | 4.87 |
| Thickness (μm) | 6.6 | 24.7 |
| Mass (g/m$^2$) | 2.3 | 2.2 |
| Porosity (%) | 83.8 | 95.9 |
| Solid Feature Spacing (μm) | N/A | 24.4 |
| Solid Feature Minor Axis (μm) | N/A | 4.2 |
| Solid Feature Major Axis (μm) | N/A | 7.5 |
| Solid Feature Depth (μm) | N/A | 5.2 |
| Weakest Axis Tensile Strength (N/m) | 210.9 | |
| Geometric Mean Tensile Strength (MPa) | 38.1 | |
| Composite Bond (kPa) | 170.2 | |

Evaluation of the Composite Membrane Performance

The biocompatible membrane composite was thermally welded into a device form in accordance with the Integration of Biocompatible Membrane Composite into a Device Form set forth in the Test Methods section above and evaluated in vivo.

Figure 32:
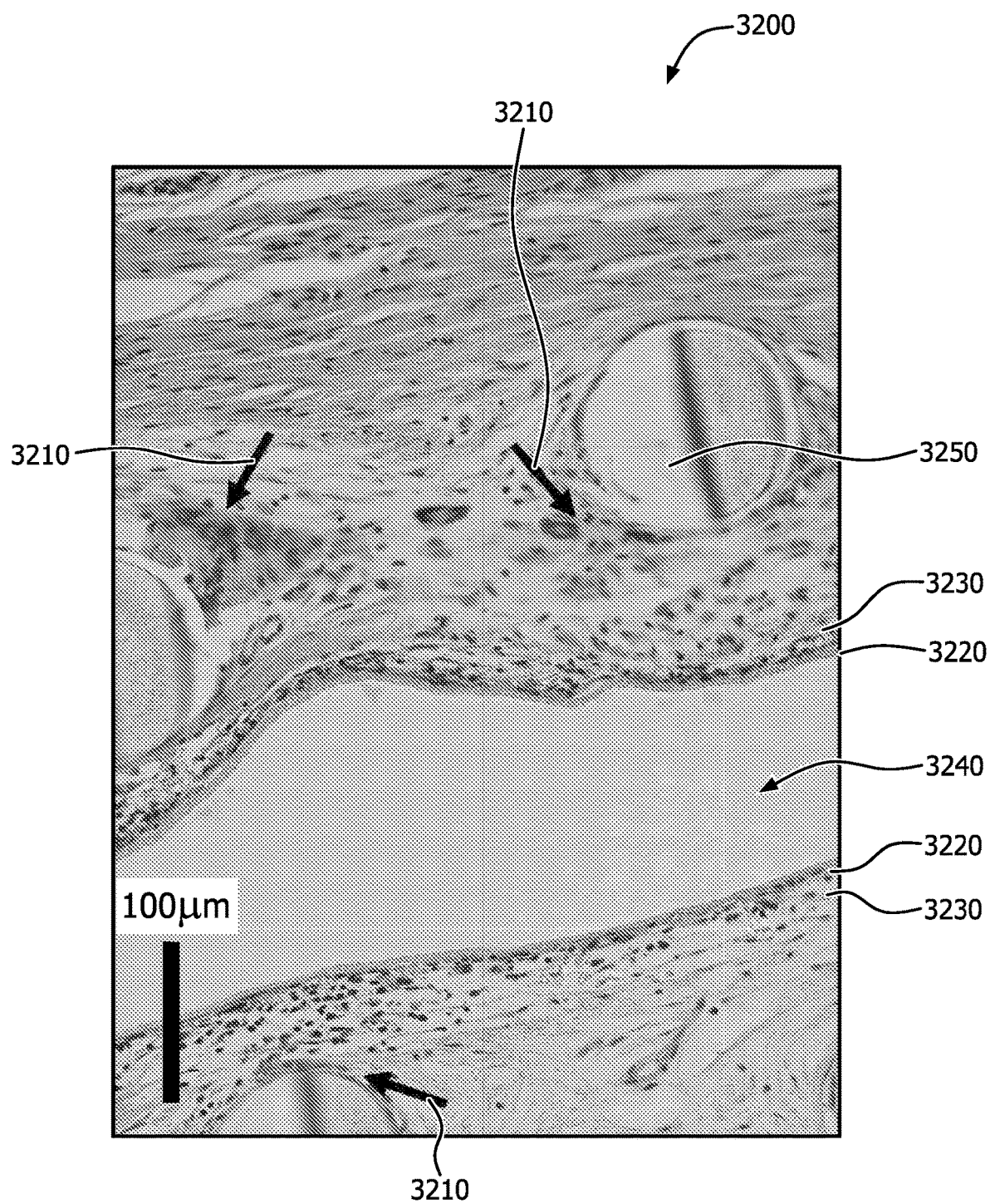
FIG. 32 is a representative histology image depicting the absence of the formation of foreign body giant cells on the cell impermeable layer of Example 3 in accordance with embodiments described herein.

The device was evaluated in vivo for host tissue response in the In Vivo Porcine Study set forth in the Method section above The host tissue response at the device interface demonstrated host tissue penetration through the polyester woven mesh reinforcing component and open ePTFE mitigation layer up to the tight ePTFE cell impermeable layer. While foreign body giant cells were present within the polyester woven mesh (reinforcing component), there was limited evidence of foreign body giant cells observed lining the tight, ePTFE layer (Cell Impermeable Layer) in comparison to what was observed in Comparable Examples 1-3. The histology image shown in FIG. 32 is a representative image of this observation, with arrows 3210 indicating the location of the foreign body giant cells in relation to each layer of the biocompatible membrane composite 3200. Additionally, as shown in FIG. 32, foreign body giant cells did not line the surface of the cell impermeable layer 3220. It was concluded that the biocompatible membrane composite 3200 formed of the cell impermeable layer 3220 and the mitigation layer 3230 described in this Example reduced the formation of foreign body giant cells on the surface of the cell impermeable layer 3220. The lumen 3240 and an external reinforcing component 3250 are also depicted in FIG. 32. Additionally, even though the cell impermeable membrane had low thickness and mass, it was observed that the tensile strength was adequate to maintain the integrity of the lumen since no host cells were observed breaching the lumen.

Example 4

Figure 33:
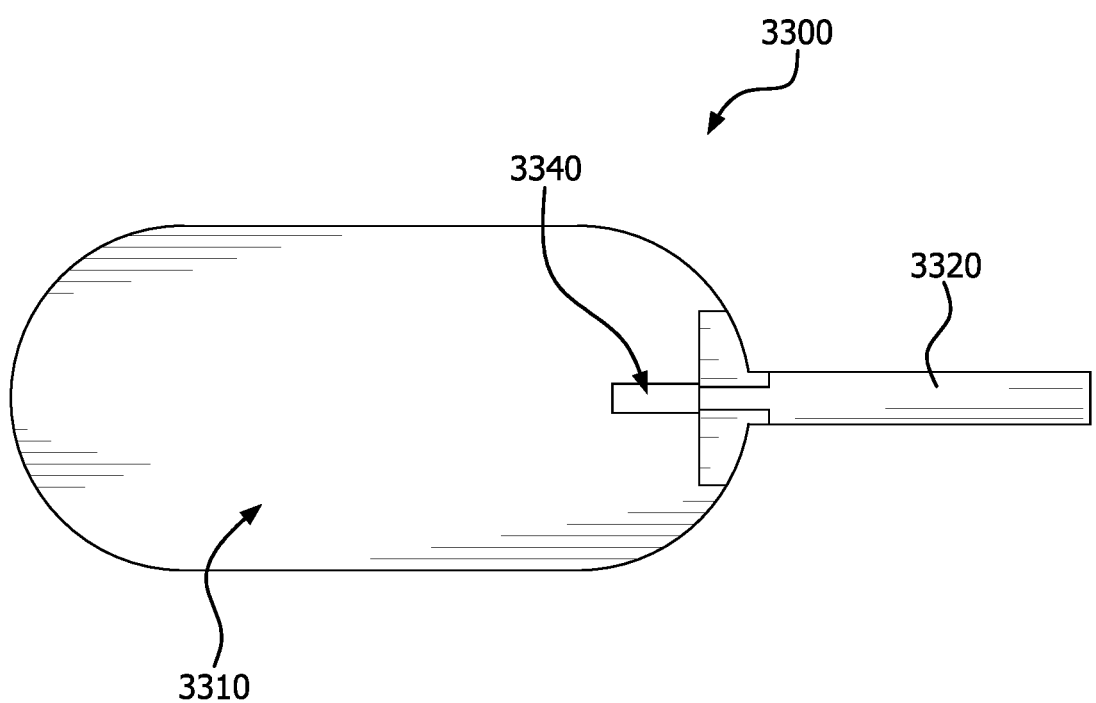
FIG. 33 is a schematic illustration of a top view of a planar reinforcing insert in accordance with embodiments described herein.

The biocompatible membrane composite described in Example 1 was used and integrated into an alternate device form that differs from what was previously described devices (i.e., the devices in Examples 1-3) in that the planar device is based on an internal reinforcing component (depicted in FIG. 33) that is located adjacent to the cell impermeable layers of the biocompatible membrane composites in final device form (e.g., a planar device). The internal reinforcing component is located within the lumen of a planar device (e.g., endoskeleton). The internal reinforcing component 3300 includes a planar insert 3310 and an integrated filling tube 3320 with a flow through hole 3340 to access both sides of the internal reinforcing component 3300.

Figure 34:
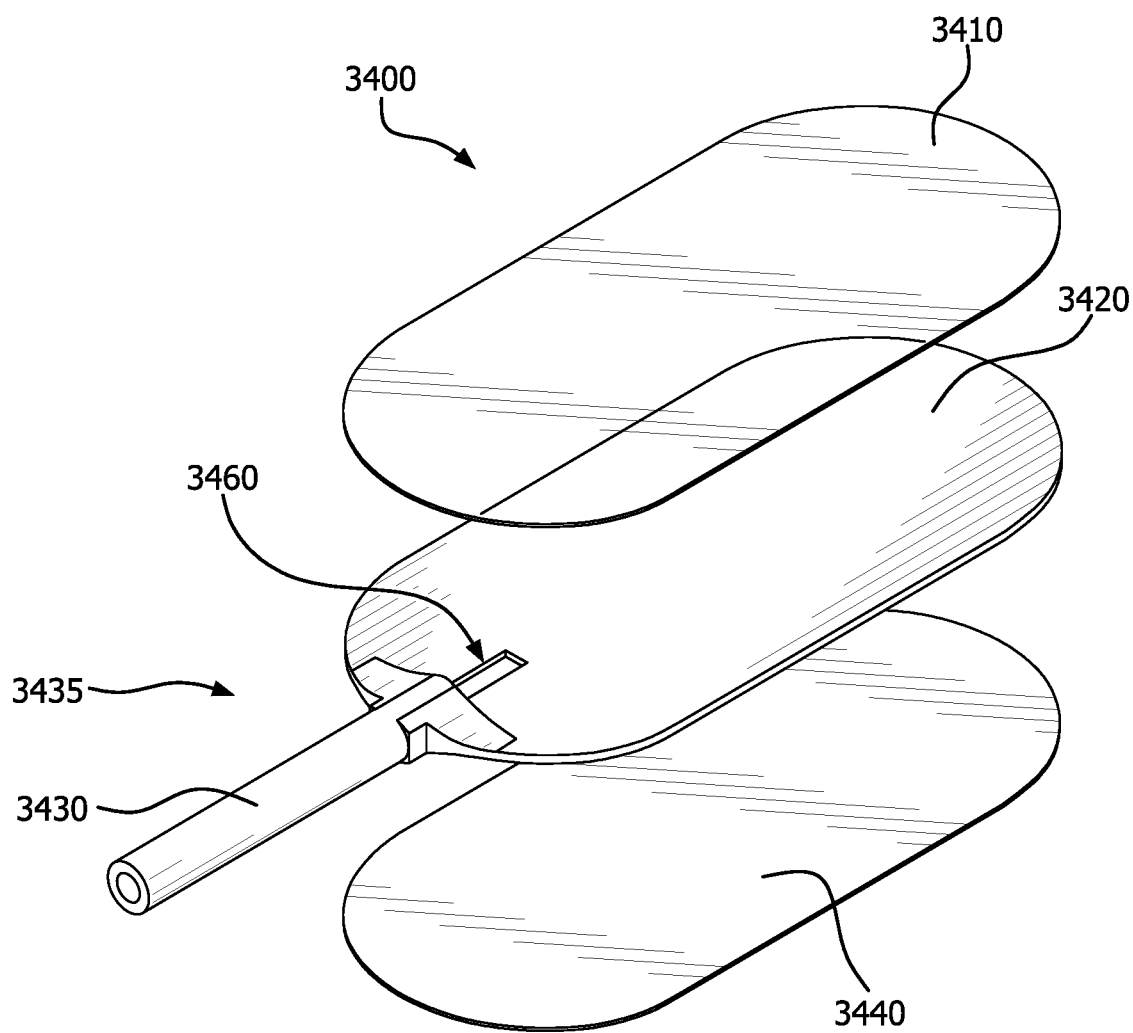
FIG. 34 is a schematic illustration of an exploded view of a molded planar device including the planar reinforcing insert of FIG. 33 in accordance with embodiments described herein.

The planar device 3400 is shown generally in FIG. 34 (in an exploded view). As shown in FIG. 34, the planar device 3400 included a first biocompatible membrane composite 3410, a second biocompatible membrane composite 3440, an internal reinforcing component 3435 that includes a planar insert 3420 and an integrated filling tube 3430 with a flow through hole 3460 to access dual internal lumens (not shown) formed on both sides of the internal reinforcing component 3435 when the biocompatible membranes 3410, 3440 are integrated into a final device form.

The internal reinforcing component was constructed by placing a sheet of a fluorothermoplastic terpolymer of TFE, HFP, and VDF into a mold cavity and compressing in a heated press (Wabash C30H-15-CPX) set at a temperature above the softening temperature of the polymer so that it conforms to the final dimension and shape. The resulting internal reinforcing component had a thickness of approximately 270 microns and a 3 point bend stiffness of 0.7 N.

Two layers of the membrane composite were cut to approximately 1"×2" (2.54 cm×5.08 cm) and arranged on both sides of the internal reinforcing component (planar insert) with the Cell Impermeable Layers facing inwards towards the lumen and the internal reinforcing component. A perimeter seal was formed around the internal reinforcing component after laying up a biocompatible membrane composite 3410, an internal reinforcing component 3435, and another biocompatible membrane composite 3440.

Figure 35:
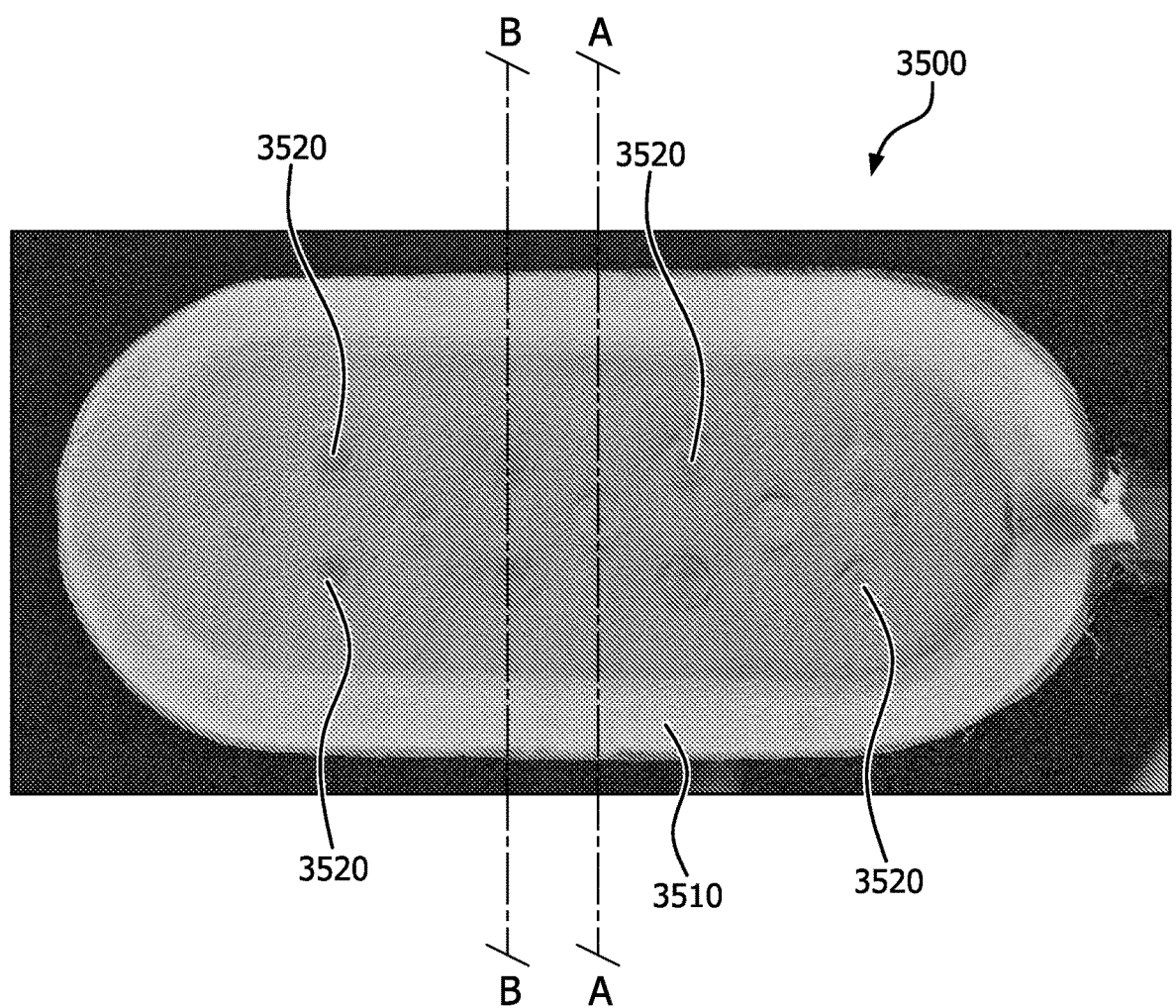
FIG. 35 is an image of a top view of a surface of a planar device in accordance with embodiments described herein.
Figure 36A:
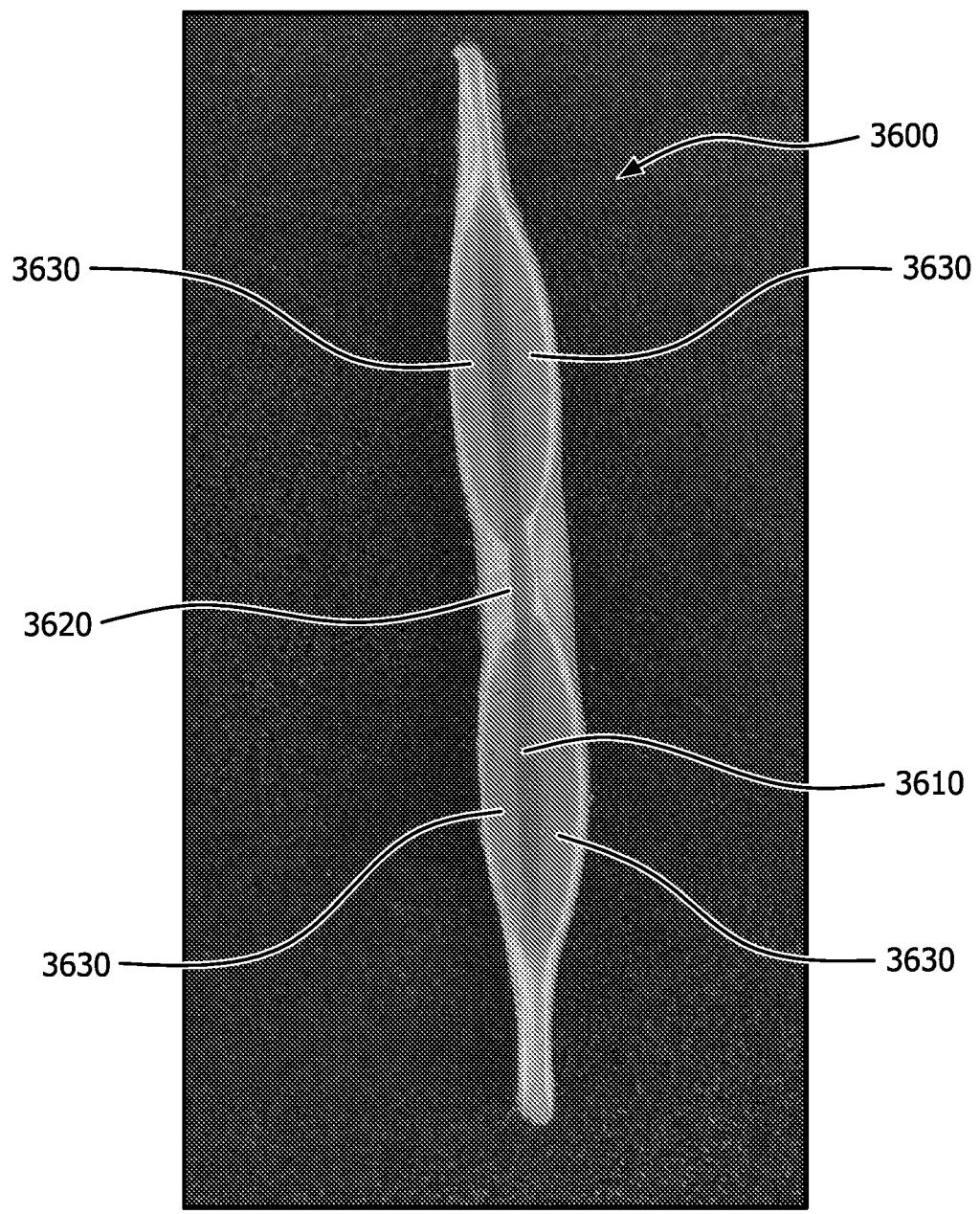
FIG. 36A is an image of a cross-section of the planar device of FIG. 35 taken along line A-A showing a single point bond and the lumen in accordance with embodiments described herein.
Figure 36B:
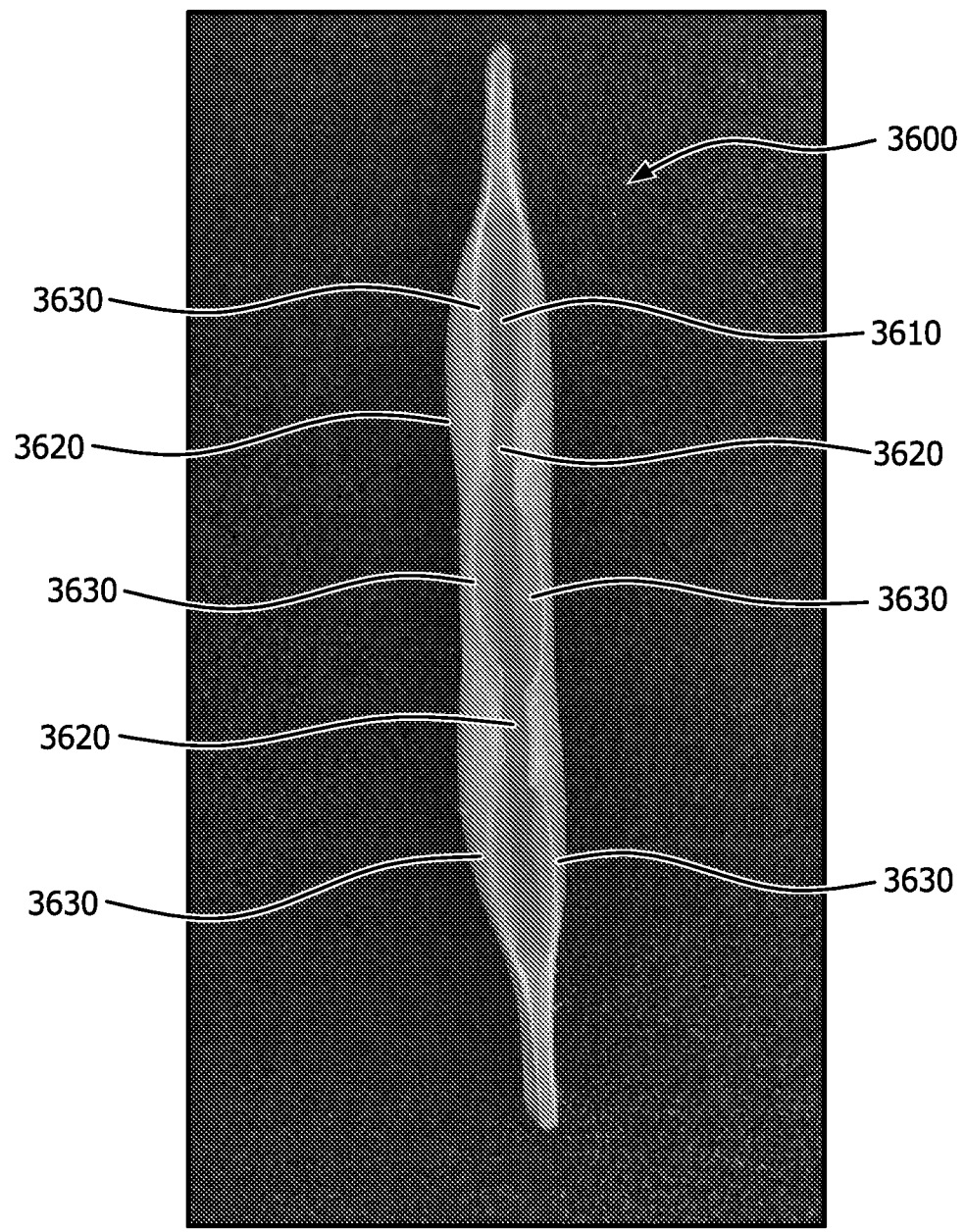
FIG. 36B is an image of a cross-section the planar device of FIG. 35 taken along line B-B showing two point bonds and the lumen in accordance with embodiments described herein.

To create the planar device 3500 shown in FIG. 35, a weld was formed by compressing the stack along the perimeter edge 3510 at 15 PSI and heating simultaneously using impulse heat bands from both sides of the with a steel mandrel in the filling tube to prevent welding in this region. Temperature and pressure were applied such that the internal reinforcing component thermoplastic softened enough to form a bond into each composite membrane. Internal points of the internal reinforcing component were bonded to each membrane composite surface by applying light manual pressure with a thermal head set to create internal point bonds 3520 of approximately 1 mm diameter spaced at least 1.45 mm apart at 12 locations on each side. The integrity of the welds were evaluated for suitability by testing for the presence of leaks visually detected as a stream of bubbles when submerged in isopropyl alcohol at an internal pressure of 5 psi. The internal geometry of the internal reinforcing component 3610 and internal lumen 3630 of the planar device 3600 is shown through cross-section in FIGS. 36A and 36B. FIG. 36A depicts a cross-section of the planar device 3500 taken along line A-A showing a single point bond 3620 and the lumen 3630. FIG. 36B is a cross-section image of the planar device 3500 taken along line B-B showing two point bonds 3620 and the lumen 3630. The finished planar device shown in FIG. 34 was filled with a low viscosity silastic to allow for better visualization and imaging of the internal reinforcing component 3610 shown in FIGS. 36A and 36B.

Figure 40:
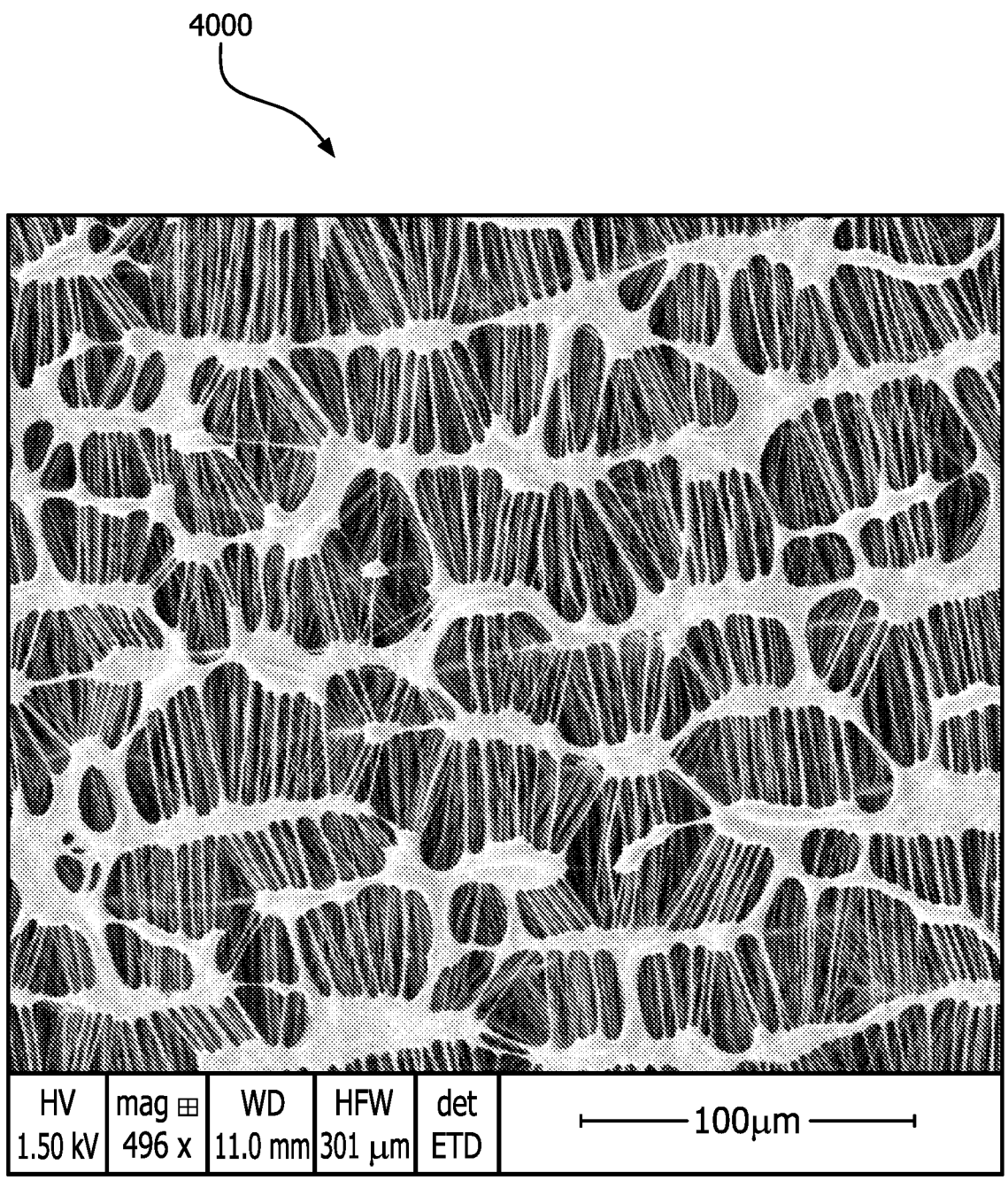
FIG. 40 is a representative histology image of the cross-section of the planar device of Example 4 depicting in vivo cell viability in accordance with embodiments described herein.

The functional performance of planar device 3500 loaded with cells was evaluated in accordance with the Nude Rat Explant Histology set forth above in the Test Methods section. A representative histology image of a cross-section of the planar device 3500 is shown in FIG. 40. From the evaluation of the histology images, it was determined that in the presence of an open mitigation layer and an internal reinforcing component viable cells 4010 were present in the lumen of a cell encapsulation device lumen.

Example 5

Manufacturing of Biocompatible Membrane Composite

A composite was constructed with two distinct layers. A first ePTFE membrane (Cell Impermeable Layer) was formed according to the teachings of U.S. Pat. No. 3,953,566 to Gore.

A second ePTFE membrane (Mitigation Layer) was prepared according to the teachings of U.S. Pat. No. 5,814,405 to Branca, et al. During the initial machine direction (MD) expansion step, a fluorinated ethylene propylene (FEP) film was applied to the second ePTFE membrane. Through subsequent co-processing of the second ePTFE membrane and FEP through machine direction (MD) expansion and transverse direction (TD) expansion, the FEP became discontinuous on the second ePTFE membrane as per the teachings of WO 94/13469 to Bacino.

Figure 41:
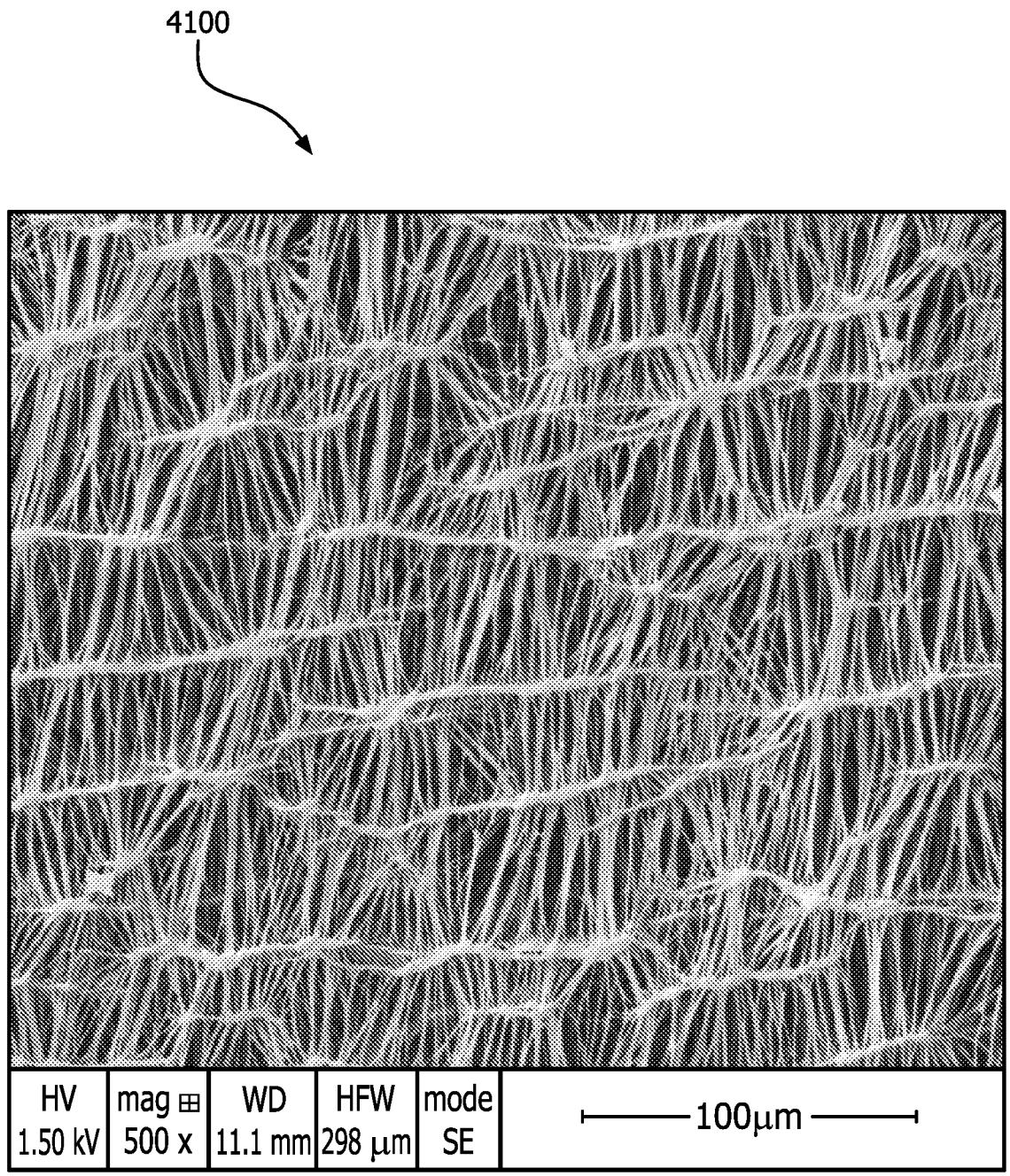
FIG. 41 is an SEM image of the node and fibril structure of the ePTFE mitigation layer of Example 5 in accordance with embodiments described herein.
Figure 42:
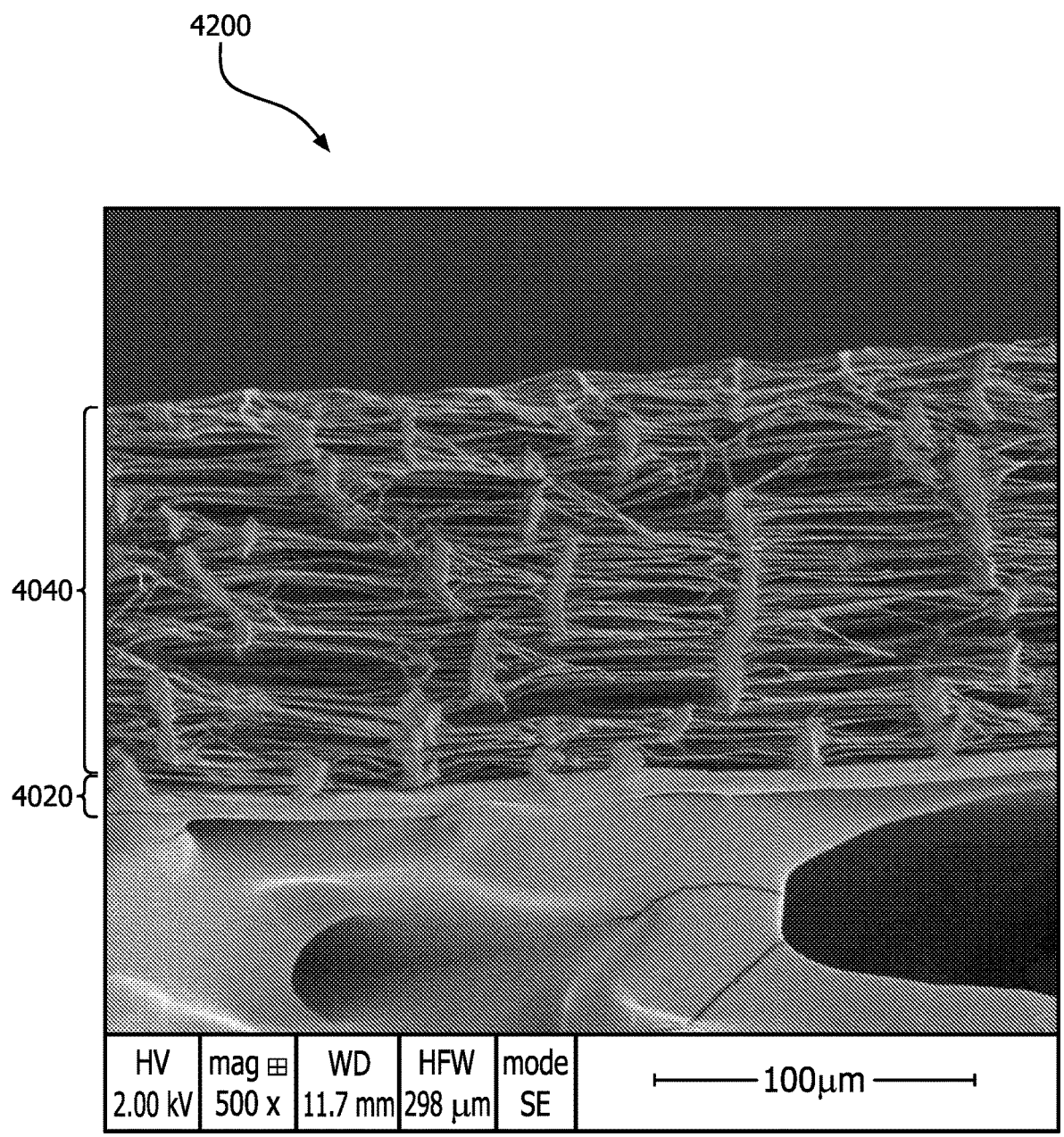
FIG. 42 is SEM image of the cross-section of the two-layer ePTFE composite formed in Example 5 in accordance with embodiments described herein.

The second ePTFE layer including the discontinuous layer of FEP thereon was laminated to the first ePTFE layer by bringing the materials (with the FEP positioned between the two ePTFE membranes) into contact at a temperature above the melting point of the FEP with the layers restrained in the transverse direction. The composite was subsequently rendered hydrophilic per the teachings of U.S. Pat. No. 5,902,745, to Butler, et al. The SEM image shown in FIG. 40 is a representative image of the second ePTFE membrane surface with the discontinuous layer of FEP thereon. The SEM image shown in FIG. 18 is a representative image of the node and fibril structure of the first ePTFE membrane (Cell Impermeable Layer). The SEM image shown in FIG. 41 is a representative image of the node and fibril structure of the second ePTFE membrane (Mitigation Layer). The SEM image shown in FIG. 42 is a representative image of the cross-section structure of the two-layer composite depicting the first ePTFE membrane 4020 (Cell Impermeable Layer) and the second ePTFE membrane 4040 (Mitigation Layer).

Characterization of the Biocompatible Membrane Composite

Each layer of the two-layer composite was evaluated and characterized for the relevant parameters necessary for the function of each layer. Parameters for layers are marked as "N/A" if they are not relevant for that layer's specific function. Parameters for layers are marked as "—" if they are practically unobtainable as a result of how the layers of the composite were processed. The methods used for the characterization of the relevant parameters were performed in accordance with the methods described in "Test Methods" section set forth above. The results of Example 5 are summarized in Table 9.

TABLE 9

| Layer Function | Cell Impermeable | FBGC Mitigation |
|---|---|---|
| Description | ePTFE Tight Layer | ePTFE Open Layer |
| MPS (μm) | 0.23 | — |
| Pore Size (μm) | 0.38 | 7.79 |
| Thickness (μm) | 10.4 | 120.8 |
| Mass (g/m$^2$) | 4.0 | 15.4 |
| Porosity (%) | 82.6 | 94.2 |
| Solid Feature Spacing (μm) | N/A | 22.2 |
| Solid Feature Minor Axis (μm) | N/A | 7.1 |
| Solid Feature Major Axis (μm) | N/A | 37.2 |
| Solid Feature Depth (μm) | N/A | 14.3 |
| Weakest Axis Tensile Strength (N/m) | 945.7 | |
| Geometric Mean Tensile Strength (MPa) | 15.7 | |
| Composite Bond (kPa) | 873.3 | |

Evaluation of the Composite Membrane Performance

Figure 39:
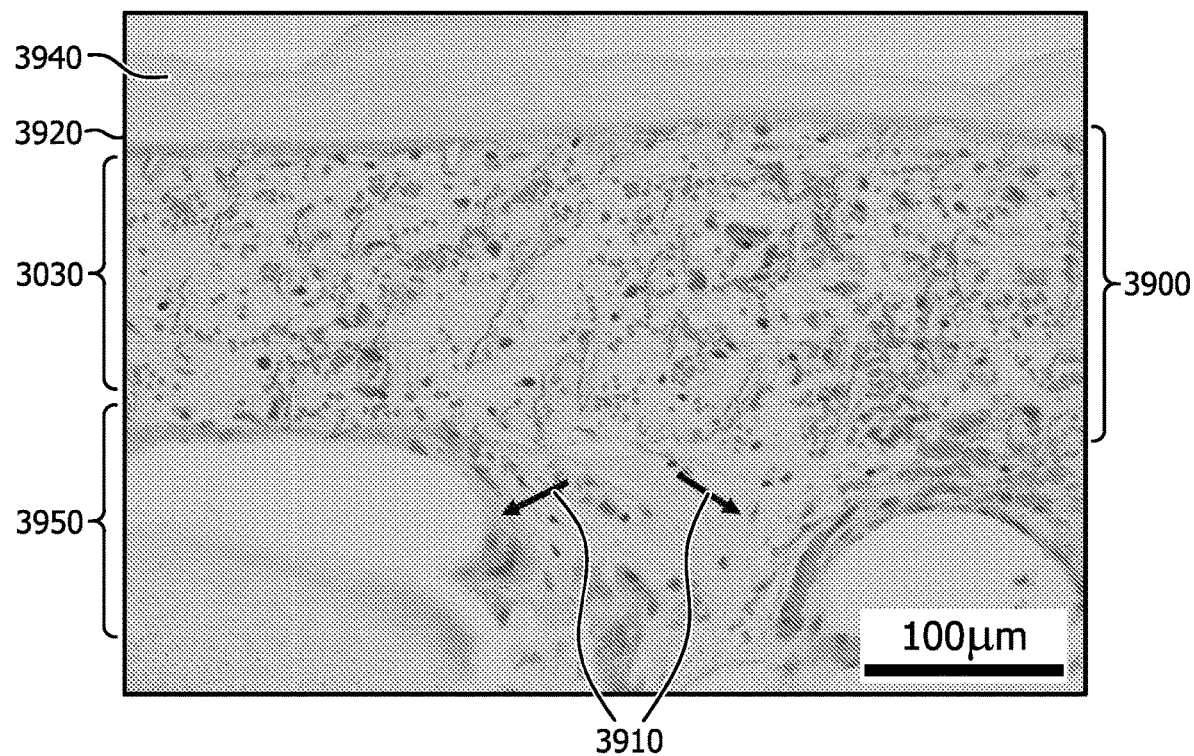
FIG. 39 is a representative histology image showing the absence of the formation of foreign body giant cell on the cell impermeable layer of Example 5 in accordance with embodiments described herein.

The biocompatible membrane composite was thermally welded into a device form in accordance with the Integration of Biocompatible Membrane Composite into a Device Form set forth in the Test Methods section above The device was evaluated for host tissue response in accordance with the In Vivo Porcine Study set forth in the Test Methods section above. The host tissue response at the device interface demonstrated host tissue penetration through the polyester woven mesh reinforcing component and open ePTFE mitigation layer up to the tight ePTFE cell impermeable layer. While foreign body giant cells were present within the polyester woven mesh (external reinforcing component), there was limited evidence of foreign body giant cells observed lining the tight, ePTFE layer (Cell Impermeable Layer) in comparison to what was observed in Comparable Examples 1-3. The histology image shown in FIG. 39 is a representative image of this observation, with arrows 3910 indicating the location of the foreign body giant cells in relation to each layer of the biocompatible membrane composite 3900. Additionally, as shown in FIG. 39, foreign body giant cells did not line the surface of the cell impermeable layer 3920. It was concluded that the biocompatible membrane composite 3900 formed of the cell impermeable layer 3920 and the mitigation layer 3930 described in this Example reduced the formation of foreign body giant cells on the surface of the cell impermeable layer 3920. The lumen 3940 and an external reinforcing component 3950 are also depicted in FIG. 39.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

That which is claimed:

1. A biocompatible membrane composite comprising:
a first layer having pores with a maximum pore size (MPS) less than about 1 micron, wherein the first layer has a first thickness less than 10 microns, and wherein the first layer is cell impermeable; and
a second layer having solid features, wherein the second layer has a second thickness less than 200 microns, and wherein the second layer allows cellular ingrowth,
wherein a majority of the solid features has a solid feature spacing less than about 50 microns,
wherein the solid features each comprise a representative minor axis, a representative major axis, and a solid feature depth, and
wherein a majority of at least two of the representative minor axis, the representative major axis, and the solid feature depth are greater than about 5 microns.

2. The biocompatible membrane composite of claim 1, wherein a majority of the representative minor axis is from about 3 microns to about 20 microns.

3. The biocompatible membrane composite of claim 1, wherein the first layer has a mass per area (MpA) less than about 5 g/m².

4. The biocompatible membrane composite of claim 1, wherein the biocompatible membrane composite has a maximum tensile load in the weakest axis greater than about 40 N/m.

5. The biocompatible membrane composite of claim 1, wherein at least a portion of the solid features in contact with the first layer are bonded solid features.

6. The biocompatible membrane composite of claim 1, wherein the solid features are connected by fibrils and the fibrils are deformable.

7. The biocompatible membrane composite of claim 1, wherein the first layer and the second layer are intimately bonded.

8. The biocompatible membrane composite of claim 1, comprising a reinforcing component.

9. The biocompatible membrane composite of claim 8, wherein the reinforcing component comprises a woven or non-woven textile.

10. The biocompatible membrane composite of claim 1, wherein the solid features of the second layer comprise a member selected from thermoplastic polymers, polyurethanes, silicones, rubbers, epoxies and combinations thereof.

11. The biocompatible membrane composite of claim 1, wherein the biocompatible membrane composite has thereon a surface coating comprising one or more members selected from antimicrobial agents, antibodies, pharmaceuticals and biologically active molecules.

12. The biocompatible membrane composite of claim 1, wherein the biocompatible membrane composite has a hydrophilic coating thereon.

13. A cell encapsulation device comprising the biocompatible membrane composite of claim 1.

14. The cell encapsulation device of claim 13, wherein the device comprises PDX-1 positive pancreatic endoderm cells or endocrine precursor cells or endocrine cells.

15. A biocompatible membrane composite comprising:
a first layer having a maximum pore size (MPS) less than about 1 micron and a first thickness less than about 10 microns, and wherein the first layer is cell impermeable; and
a second layer including solid features, wherein the second layer has a second thickness less than about 200 microns, wherein the second layer facilitates cellular ingrowth, and wherein a majority of the solid features have a solid feature spacing less than about 50 microns;
wherein the solid features each comprise a representative minor axis, a representative major axis, and a solid feature depth, and
wherein a majority of at least two of the representative minor axis, the representative major axis, and the solid feature depth are greater than about 5 microns.

16. The biocompatible membrane composite of claim 15, wherein the biocompatible membrane composite has a maximum tensile load in the weakest axis greater than about 40 N/m.

17. The biocompatible membrane composite of claim 16, wherein the solid features of the second layer comprise a member selected from thermoplastic polymers, polyurethanes, silicones, rubbers, epoxies and combinations thereof.

18. The biocompatible membrane composite of claim 16, wherein the biocompatible membrane composite has thereon a surface coating comprising one or more members selected from antimicrobial agents, antibodies, pharmaceuticals and biologically active molecules.

19. The biocompatible membrane composite of claim 16, wherein the biocompatible membrane composite has a hydrophilic coating thereon.

20. The biocompatible membrane composite of claim 15, wherein the first layer has a mass per area (MpA) less than about 5 g/m².

21. The biocompatible membrane composite of claim 15, wherein the solid feature depth is less than the second thickness of the second layer.

22. The biocompatible membrane composite of claim 15, wherein the solid features are connected by fibrils and said fibrils are deformable.

23. The biocompatible membrane composite of claim 15, wherein at least a portion of the first-solid features in contact with the first layer are bonded solid features.

24. The biocompatible membrane composite of claim 15, wherein the first layer and the second layer are intimately bonded.

25. The biocompatible membrane composite of claim 15, comprising a reinforcing component.

26. The biocompatible membrane composite of claim 25, wherein the reinforcing component is a woven or non-woven textile.

27. A cell encapsulation device comprising the biocompatible membrane composite of claim 15.

28. The cell encapsulation device of claim 27, wherein the device comprises PDX-1 positive pancreatic endoderm cells or endocrine precursor cells or endocrine cells.

* * * * *